United States Patent
Zidan et al.

(10) Patent No.: US 11,612,316 B2
(45) Date of Patent: Mar. 28, 2023

(54) MEDICAL SYSTEM AND METHOD OPERABLE TO CONTROL SENSOR-BASED WEARABLE DEVICES FOR EXAMINING EYES

(71) Applicants: Awss Zidan, New York, NY (US); Ayham Boucher, Skaneateles, NY (US)

(72) Inventors: Awss Zidan, New York, NY (US); Ayham Boucher, Skaneateles, NY (US)

(*) Notice: Subject to any disclaimer, the term of this patent is extended or adjusted under 35 U.S.C. 154(b) by 296 days.

(21) Appl. No.: 16/907,906

(22) Filed: Jun. 22, 2020

(65) Prior Publication Data
US 2020/0397288 A1 Dec. 24, 2020

Related U.S. Application Data

(60) Provisional application No. 62/864,303, filed on Jun. 20, 2019.

(51) Int. Cl.
*A61B 3/12* (2006.01)
*A61B 3/00* (2006.01)
(Continued)

(52) U.S. Cl.
CPC ............. *A61B 3/12* (2013.01); *A61B 3/005* (2013.01); *A61B 3/0058* (2013.01); *A61B 3/112* (2013.01);
(Continued)

(58) Field of Classification Search
CPC ........ G02B 27/0093; G02B 2027/0178; A61B 3/113; A61B 3/005; A61B 3/0058; A61B 3/112
(Continued)

(56) References Cited

U.S. PATENT DOCUMENTS 5,555,895 A * 9/1996 Ulmer .................... A61B 3/113
600/595
5,583,795 A * 12/1996 Smyth .................. A61B 3/0025
702/92

(Continued)

FOREIGN PATENT DOCUMENTS

WO 2018174507 A1 9/2018

OTHER PUBLICATIONS

Medgadget Editors; "How Stanford Uses Eye-Tracking Virtual Reality Headset to Detect Concussions in Athletes"; retrieved from the Internet <https://www.medgadget.com/2016/10/stanford-uses-eye-tracking-virtual-reality-headset-detect-concussions-athletes.html>; Oct. 3, 2016 (6 pages).

(Continued)

*Primary Examiner* — Zachary W Wilkes
(74) *Attorney, Agent, or Firm* — Barclay Damon LLP

(57) ABSTRACT

A medical system and method are disclosed herein. The medical system, in an embodiment, has computer-readable instructions configured to be executed by one or more processors to cause at least one display device of a wearable device to generate a plurality of graphics. The graphics are configured to stimulate a voluntary eye function of at least one eye of a subject, to stimulate an involuntary eye function of the at least one eye, and to block a vision of the at least one eye. The instructions are also configured to cause at least one sensor of the wearable device to sense eye movement, head movement, and pupillary resizing. The instructions are also configured to cause processing of a plurality of sensed eye parameters and any sensed head movement parameters and to generate an examination output that at least indicates a plurality of the sensed eye parameters.

20 Claims, 67 Drawing Sheets

(51) Int. Cl.
    *A61B 3/11*     (2006.01)
    *A61B 3/113*     (2006.01)
    *A61B 5/11*     (2006.01)
    *A61B 5/00*     (2006.01)
    *G02B 27/00*     (2006.01)
    *G02B 27/01*     (2006.01)

(52) U.S. Cl.
    CPC ............... *A61B 3/113* (2013.01); *A61B 5/11* (2013.01); *A61B 5/4023* (2013.01); *G02B 27/0093* (2013.01); *G02B 27/0172* (2013.01)

(58) Field of Classification Search
    USPC .......................................................... 351/209
    See application file for complete search history.

(56) References Cited

U.S. PATENT DOCUMENTS

| | | | |
|---|---|---|---|
| 7,575,321 B2 | 8/2009 | Newman et al. | |
| 7,708,403 B2 | 5/2010 | Newman | |
| 8,568,311 B2* | 10/2013 | LaPlaca | A61B 5/4076 |
| | | | 128/920 |
| 8,702,234 B2 | 4/2014 | Newman et al. | |
| 8,931,905 B2* | 1/2015 | Lewis | A61B 3/032 |
| | | | 351/209 |
| 9,004,687 B2* | 4/2015 | Stack | A61B 5/6803 |
| | | | 351/209 |
| 9,039,632 B2 | 5/2015 | Kiderman et al. | |
| 9,788,714 B2* | 10/2017 | Krueger | G06T 19/006 |
| 10,136,810 B2* | 11/2018 | Migliaccio | A61B 5/742 |
| 10,209,773 B2* | 2/2019 | Khaderi | A61B 5/369 |
| 10,463,248 B2 | 11/2019 | Cornsweet et al. | |
| 10,488,920 B2 | 11/2019 | Lin et al. | |
| 10,915,166 B2* | 2/2021 | Ishii | A63F 13/212 |
| 10,973,409 B2* | 4/2021 | Kiderman | G02B 27/017 |
| 11,334,213 B2* | 5/2022 | Panse | G06F 3/017 |
| 2002/0099305 A1* | 7/2002 | Fukushima | A61B 3/113 |
| | | | 600/300 |
| 2006/0005846 A1* | 1/2006 | Krueger | A61H 5/00 |
| | | | 128/898 |
| 2006/0197832 A1* | 9/2006 | Yamada | G02B 27/017 |
| | | | 348/E5.145 |
| 2016/0007921 A1* | 1/2016 | Galea | A61B 5/6803 |
| | | | 600/301 |
| 2016/0262608 A1* | 9/2016 | Krueger | G16H 50/20 |
| 2016/0270711 A1* | 9/2016 | Ashmore | A61B 5/398 |
| 2017/0000329 A1 | 1/2017 | Samec et al. | |
| 2017/0042462 A1 | 2/2017 | Kiderman et al. | |
| 2018/0227630 A1* | 8/2018 | Schmidt | H04N 21/4728 |
| 2019/0150727 A1* | 5/2019 | Blaha | A61B 3/0091 |
| 2019/0333361 A1 | 10/2019 | Gullander | |
| 2020/0085298 A1 | 3/2020 | Cornsweet et al. | |
| 2020/0113501 A1 | 4/2020 | Kiderman et al. | |
| 2021/0258354 A1* | 8/2021 | Kim | H04N 7/14 |
| 2022/0133212 A1* | 5/2022 | Krueger | A61B 5/163 |
| | | | 600/301 |

OTHER PUBLICATIONS

Dr. Awss Zidan; "Dancing Eye Mobile App"; Presentation at ANN Conference; May 4, 2019 (8 pages).

Wikipedia; "Virtual Reality Headset"; Jun. 3, 2020; retrieved from the Internet <https://en.wikipedia.org/wiki/Virtual_reality_headset> (8 pages).

HTC Corporation;"Professional-Grade VR Systems, VIVE Pro Eye Office";; On or before Jun. 3, 2020 (8 pages).

VB; "SyncThink's eye-tracking helps monitor brain health and concussion risk"; Dean Takahashi; Dec. 9, 2019 (4 pages).

* cited by examiner

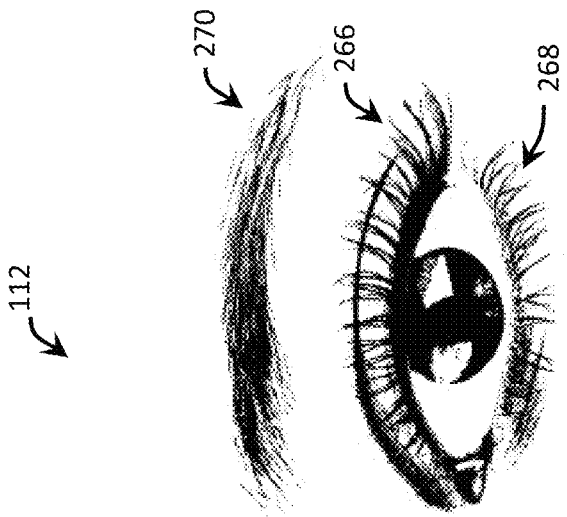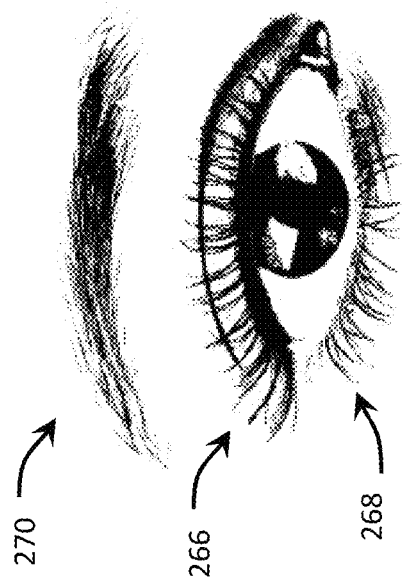
FIG. 25

FIG. 58

| Eye Characteristic Category 368 | Eye Abnormality 370 | Benchmark Parameter 372 | Sensed Parameter 366 | Percentile 374 | Deviation 376 | Severity Indicator 378 |
|---|---|---|---|---|---|---|
| Category C1 | A1 | 23 mm | 19 mm | 82nd | 17.4% | #3 |
| Category C2 | A2 | 42 mm | 2 mm | <5th | 95.2% | #1 |
| Category C3 | A3 | 15 degrees | 21 degrees | 60th | 40% | #2 |
| Category C4 | A5 | Yes (1) | No (0) | --- | 1 | #1 |
| Category C5 | A6 | 4 | 2 | --- | 50% | #3 |

FIG. 59

| Possible Diagnosis | Medical Analysis Factors | | | Certainty Indicator |
|---|---|---|---|---|
| Disorder D1 | A2 Deviation > 95% | --- | --- | #2 |
| Disorder D2 | A1 Deviation > 10% | A2 Deviation > 30% | --- | #3 |
| Disorder D3 | A3 Deviation > 30% | A5 Deviation | A6 Deviation > 40% | #1 |

FIG. 62

EXAMINATION OUTPUT (PAGE 1 OF 3)

EYE MOTILITY REPORT

Ductions

Right: __ Full / X Limited in: X abduction/X adduction/ __ elevation/__ depression.

Left: X Full

Version: __ Full / X Limited in: X abduction/__ adduction/ __ elevation/__ depression.

Vergence: X Intact / __ Insufficient

Pursuit: X smooth/__ saccadic

Saccades: X Normal / __ Hypometric / __ Hypermetric

Nystagmus: X Absent / __ Present (If so, then description such as jerk/pendular nystagmus that is more prominent in left/right gaze.etc)

Internuclear ophthalmoplegia: X Absent /__ Present
Saccadic Intrusions/Oscillations: X Absent/__ Present Ocular alignment measured using cover-uncover testing reveals X right/__ left: __ exo/X iso X tropia/__ phoria Head tilt in primary gaze : __ absent / X present by 5 degrees

EXAMINATION OUTPUT (PAGE 2 OF 3)

Pupils

Size in dark: 3.5 mm

Size in light: 2.5 mm

Reaction to light grading system 1 to 4: 3

Relative Afferent Pupillary Reflex: X absent / ___ present

Maneuver Testing

Nystagmus     X Absent/ ___ Present

Head Thrust     X Absent/ ___ Present

Head shaking     X Absent/ ___ Present

Head turning     X Absent/ ___ Present

Valsalva     X Absent/ ___ Present

Dix-Hallpike     X Absent/ ___ Present

McClure-Pagnini     X Absent/ ___ Present

Other tests:     X Absent/ ___ Present

External Eye Appearance

Palpebral fissure: 11 mm

Eyelid fatigue (measured during upward gaze): ___ Present/ X Absent

Lid twitch sign: ___ Present/ X Absent

FIG. 64

EXAMINATION OUTPUT (PAGE 3 OF 3)

Severity Resource
1. Limited abduction or right eye (<5th percentile)
2. Nonspecific limited adduction of right eye (35th percentile)
3. Esotropia of X degree, equivalent to Y diopter (<5th percentile).

Diagnostic Resource
1. Right 6th nerve palsy (Diagnostic certainty of X%)
2. Myasthenia gravis (Diagnostic certainty of Y%)
3. Incomplete right 3rd nerve palsy (Diagnostic certainty of Z%)

FIG. 65

Diagnostic Certainty Scale

| Certainty Indicator | | | | |
|---|---|---|---|---|
| Percentages | >95% | >75% | <50% | <25% |
| Textual Descriptions | High Certainty | Substantial Certainty | Questionable Certainty | Low Certainty |
| Symbols | ☆ | ○ | ◇ | △ |

MEDICAL SYSTEM AND METHOD OPERABLE TO CONTROL SENSOR-BASED WEARABLE DEVICES FOR EXAMINING EYES

CROSS-REFERENCE TO RELATED APPLICATION

This application is a non-provisional of, and claims the benefit and priority of, U.S. Provisional Patent Application No. 62/864,303 filed on Jun. 20, 2019. The entire contents of such application are hereby incorporated by reference.

BACKGROUND

There are different types of examinations for eyes. An optometrist may examine a patient's eyes primarily to test vision. In this type of examination, the optometrist may detect myopia, hyperopia, astigmatism or other signs of an abnormality of the eyeball, such as the eyeball being physically too long, too small or irregularly-shaped. The optometrist may prescribe eyeglasses to correct the patient's vision.

In addition to testing for vision, an ophthalmologist may perform ophthalmological examinations of patients' eyes. The purpose of this type of examination is to diagnose a variety of disorders within and outside of the visual system, including disorders of the visual system's nerves, the nervous system and the cardiovascular system. After diagnosis, the ophthalmologist may treat these disorders through medication or surgery, or the ophthalmologist may refer the patient to another physician for treatment.

The scope and complexity of an ophthalmological examination depends on the equipment available to the ophthalmologist. For example, a bedside examination may involve the use of one or more of the following: a Snellen Chart sheet for far vision, pen torch for pupil reaction, occlude for cover testing, red probe or red mydriatic bottle top for color desaturation testing, ophthalmoscope, ruler for lid function and pupil diameter, cotton wool and office pin for sensation testing, and pseudo-isochromatic plates for color vision. A more comprehensive ophthalmological examination may involve the use of complex eye examination machines, including perimetry equipment, phoropters and retinal cameras. The known perimetry equipment has a chin rest fixture, a display screen and a device generating an infrared beam to track eye movement.

There are a number of disadvantages with relying on the foregoing assortment of equipment to perform eye examinations. In many cases, health care facilities do not have this equipment assortment because of the financial cost to purchase and maintain the equipment assortment. Also, patients' insurance policies may not cover charges billed by health care facilities for using certain parts of the equipment assortment.

In addition, it can be relatively highly time consuming to properly use the equipment assortment in examinations. This is because the equipment assortment is relatively complex. Each part of the assortment requires special training and a unique set of skills for proper use. Consequently, some health care providers lack the skills and experience to properly use various parts of the equipment assortment. Furthermore, some parts of the equipment assortment, such as perimetry equipment, are relatively large and heavy, and are designed to be installed in a health care facility. Patients are not always able to travel to a health care facility for an examination.

In addition, the operation of much of the equipment assortment requires the health care provider to perform manual steps and manual record-keeping. This manual activity creates inefficiencies, risks of erroneously setting-up tests, the inability to accurately repeat certain testing steps, and risks of erroneously recording the test results. Furthermore, the equipment assortment is not designed to effectively, reliably, accurately and efficiently detect a variety of eye abnormalities, including eye misalignment and low-amplitude nystagmus. In addition, the equipment assortment results in an array of different types of examination reports. It can be difficult for health care providers to interpret the data in these reports. This creates the risk of misdiagnoses and undiagnosed disorders. This can also delay the provision of health care to patients.

The foregoing background describes some, but not necessarily all, of the problems, disadvantages, challenges and shortcomings related to the known equipment and methods used to examine eyes.

SUMMARY

The medical system, in an embodiment, includes one or more data storage devices storing a plurality of computer-readable instructions. The instructions are executable by one or more processors operatively coupled to a wearable device. The wearable device is configured to be worn on a head of a subject during an ophthalmological examination. The wearable device includes at least one display device and at least one sensor, and the wearable device is operable to cause a 3D visual effect. The instructions are configured to cause the one or more processors and the wearable device to cooperate to perform a plurality of steps. The steps include causing the at least one display device to generate a plurality of different graphics configured to stimulate a voluntary eye function of at least one eye of the subject, to stimulate an involuntary eye function of the at least one eye, and to block a vision of the at least one eye. Each of the graphics is generated within a viewing space in front of the at least one eye. The steps also include causing the at least one sensor to sense a plurality of eye positions of the at least one eye relative to an environment in which the ophthalmological examination occurs. The eye positions vary during an eye movement occurring while at least one of the graphics is generated during the ophthalmological examination. Also, the steps include causing the at least one sensor to sense a plurality of head positions of the head relative to the environment. The head positions can vary during any head movement that occurs during the ophthalmological examination. In addition, the steps include causing the at least one sensor to sense a plurality of pupil sizes of a pupil of the at least one eye. The pupil sizes can vary during a pupillary resizing that occurs during the ophthalmological examination. Furthermore, the instructions are executable by the one or more processors to process a plurality of sensed eye parameters. The sensed eye parameters include at least one sensed eye movement parameter related to the eye movement and at least one sensed pupil size parameter related to the pupillary resizing. The instructions are also executable to process at least one sensed head movement parameter related to the head movement, if any, and the instructions are executable to process medical analysis data. The medical analysis data includes a plurality of benchmark parameters associated with a plurality of eye characteristic categories. Each of the eye characteristic categories is associated with a parameter set. The parameter set includes one of the sensed eye parameters and one of the benchmark parameters that is related to such sensed eye parameter. The medical analysis data also includes a plurality of parameter deviation thresholds associated with a plurality of the eye characteristic categories. The instructions are also executable to determine, with respect to each of the parameter sets, any deviation of the sensed eye parameter of the parameter set relative to the benchmark parameter of the parameter set, and the instructions are executable to determine whether any of the deviations associated with one of the eye characteristic categories is greater than the parameter deviation threshold associated with the eye characteristic category. Furthermore, the instructions are executable to generate an examination output that indicates a plurality of the sensed eye parameters. The examination output also includes an abnormality resource if at least one of deviations associated with one of the eye characteristic categories is greater than the parameter deviation threshold associated with the eye characteristic category. Also, the examination output includes a diagnostic resource. The diagnostic resource includes a plurality of possible diagnoses indicative of a plurality of disorders associated with one or more of the eye characteristic categories.

In another embodiment, the medical system includes one or more data storage devices storing a plurality of computer-readable instructions. The instructions are configured to be executed by one or more processors to perform a plurality of steps. The steps include causing at least one display device of a wearable device to generate a plurality of graphics configured to stimulate a voluntary eye function of at least one eye of a subject, to stimulate an involuntary eye function of the at least one eye, and to block a vision of the at least one eye. The steps also include causing at least one sensor of the wearable device to sense an eye movement of the at least one eye relative to an environment, to sense any head movement of a head of the subject relative to the environment; and to sense a pupillary resizing of the at least on eye. Also, the steps include causing a processing of: (a) a plurality of sensed eye parameters related to the eye movement and the pupillary resizing; and (b) at least one sensed head movement parameter related to the head movement, if any. Furthermore, the steps include causing the generation of an examination output that indicates a plurality of the sensed eye parameters.

In yet another embodiment, the medical method includes executing a plurality of computer-readable instructions that are stored in one or more data storage devices. The execution causes at least one display device of a wearable device to generate a plurality of graphics configured to stimulate a voluntary eye function of at least one eye of a subject, to stimulate an involuntary eye function of the at least one eye, and to block a vision of the at least one eye. The execution also causes at least one sensor of the wearable device to sense an eye movement of the at least one eye relative to an environment, to sense any head movement of a head of the subject relative to the environment; and to sense a pupillary resizing of the at least on eye. Also, the execution causes a processing of a plurality of sensed eye parameters related to the eye movement and the pupillary resizing, and the execution causes a processing of at least one sensed head movement parameter related to the head movement, if any. In addition, the execution causes a generating of an examination output that indicates a plurality of the sensed eye parameters.

Additional features and advantages of the present disclosure are described in, and will be apparent from, the following Brief Description of the Drawings and Detailed Description.

BRIEF DESCRIPTION OF THE DRAWINGS

FIG. 25 is a front view of plurality of eyes a subject, illustrating anatomical parts of the eyes.

FIG. 58 is a table displaying an example of eye test results, illustrating, with respect to each eye characteristic category, the eye abnormality, benchmark parameter, sensed parameter, percentile, deviation, and severity indicator.

FIG. 59 is a table displaying an example of eye test results, illustrating, with respect to each possible diagnosis, the associated medical analysis factors and associated certainty indicator.

FIG. 62 is a front view of an example of the first page of an examination output, illustrating the first page of an example motility report.

FIG. 63 is a front view of the example of the second page of the examination output of FIG. 62, illustrating the second page of the example motility report of FIG. 62.

FIG. 64 is a front view of the example of the third page of the examination output of FIG. 62, illustrating the third page of the example motility report of FIG. 61, wherein such third page displays an example of an abnormality resource and a diagnostic resource.

FIG. 65 is a table displaying examples of different embodiments of certainty indicators and the associated diagnostic certainty scales.

DETAILED DESCRIPTION

Figure 1:
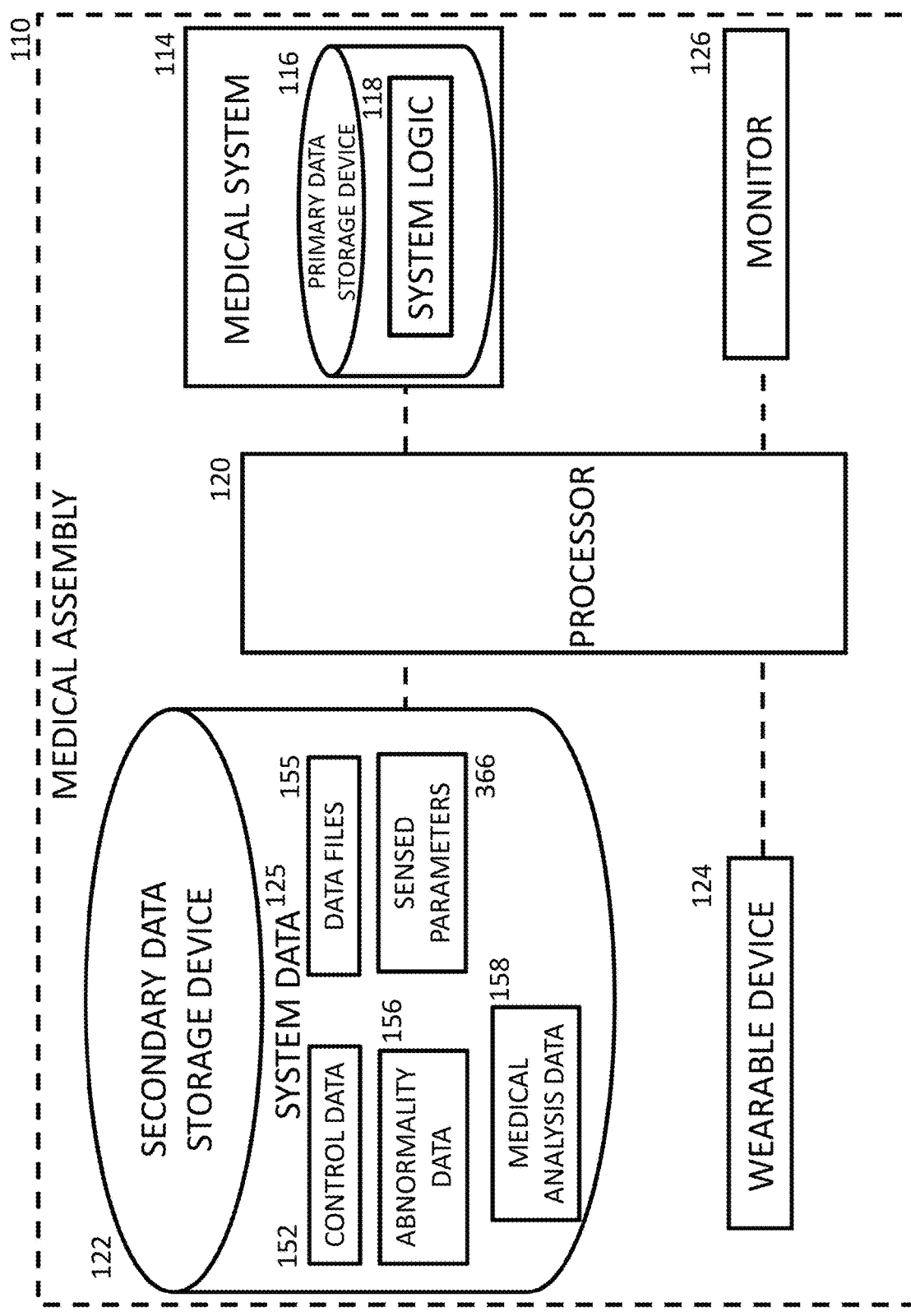
FIG. 1 is a schematic diagram illustrating an embodiment of the medical assembly.
Figure 2:
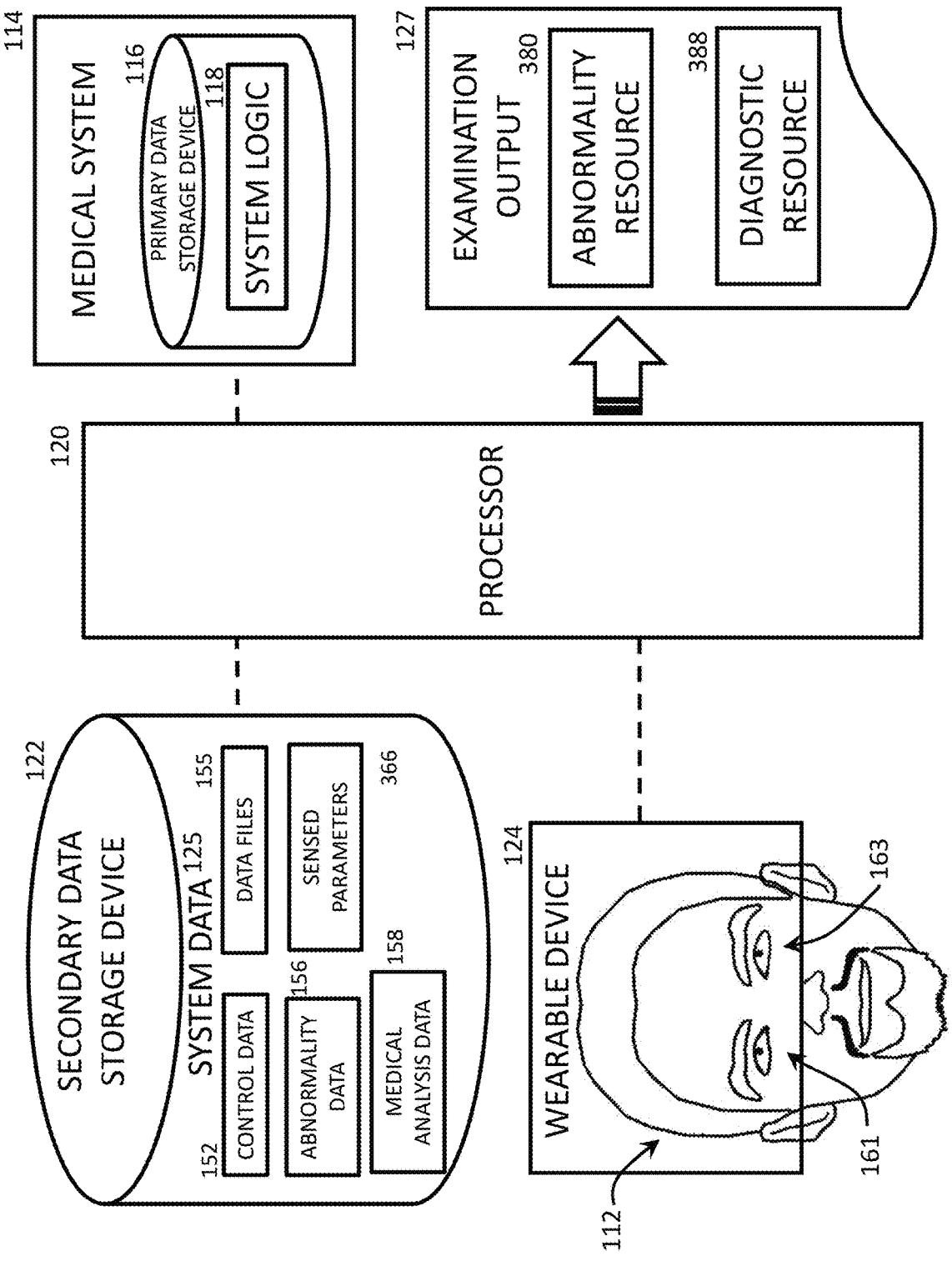
FIG. 2 is a schematic diagram illustrating the generation of an examination output by the medical assembly of FIG. 1.

Referring to FIGS. 1-2, in an embodiment, the medical assembly 110 is usable to examine the right and left eyes 161, 163 of a subject 112 through an eye examination. In this embodiment, the medical assembly 110 includes: (a) a medical system 114 having a primary data storage device 116, which stores or records system logic 118; (b) a processor 120; (c) a secondary data storage device 122 operatively coupled to the processor 120; (d) a wearable device 124 operatively coupled to the processor 120; and (e) a display device or monitor 126 operatively coupled to the processor 120. The processor 120, by executing the system logic 118, is operable to automatically generate at least one examination output 127 for each eye examination.

The medical assembly 110 (and each portion thereof) is operable for purposes of practical applications that involve the provision of health care. The medical assembly 110 is configured to be integrated into such practical applications. As described below, each examination output 127 depends on sensor-based data collection and analysis. Accordingly, the medical assembly 110 enables, and provides the basis for, several advantages and improvements, including: (a) systematic eye testing based on repeatable testing steps; (b) the elimination or reduction in testing errors, data recording errors and analysis errors; (c) enhanced effectiveness, reliability, accuracy and efficiency in detecting eye abnormalities and identifying possible diagnoses of disorders related to such abnormalities; (d) the enablement of remote examination and remote diagnosis; (e) facilitating the interpretation of examination results; and (f) reducing the risks of misdiagnoses and undiagnosed disorders.

The subject 112 can include any patient or person seeking health care or medical treatment. There can be different types of users of the medical assembly 110, including subjects 112 and health care providers. The health care providers can include examiners, eye care providers and other service providers in the health care industry. The eye care providers can include ophthalmologists, optometrists, opticians and their assistants.

The medical assembly 110 can be used in a variety of scenarios. In one scenario, the medical assembly 110 is located in a health care facility, and the subject 112 uses the wearable device 124 to examine the subject's eyes at the facility with assistance from the health care provider who is physically present at the facility. In another scenario, the health care provider travels to the subject's residence and uses the medical assembly 110 at the residence to examine the subject's eyes. In yet another scenario, the subject 112 already possesses a wearable device 124, which the subject 112 uses for personal or entertainment purposes. In still another scenario, the subject 112 purchases or leases the wearable device 124 from an online or offline supplier. The supplier ships the wearable device 124 to the subject 112 for an examination, and the subject 112 returns the wearable device 124 after the examination is complete.

In either scenario in which the subject 112 possesses the wearable device 124 at the subject's home or other place away from a health care facility, the subject 112 can remotely perform or remotely undergo an eye examination with or without the participation of the health care provider. If the subject 112 uses the wearable device 124 to remotely perform the examination without the health care provider, the subject 112 can, after the examination, send or electronically transmit the examination output 127 to the health care provider. The health care provider can then use the examination output 127 to perform a diagnosis. Alternatively, the subject 112 can contact the health care provider to initiate a remote, telehealth or telemedicine session with the health care provider. During the session, the subject 112 uses or wears the wearable device 124, and the health care provider uses the medical assembly 110 to assist and remotely examine the subject's eyes.

1. Terminology, Conventions and Examples

The term "abnormality," as used herein in various forms, encompasses, and is not limited to, an abnormality, dysfunction, pathology or impairment in any part, activity or condition of any anatomical part or system of the body.

The term "symptom," as used herein in various forms, encompasses, and is not limited to, subjective evidence of an abnormality observed by a subject.

The term "sign," as used herein in various forms, encompasses, and is not limited to, objective evidence of an abnormality observed by a health care provider.

The term "disorder," as used herein in various forms, encompasses, and is not limited to, an abnormal physical or mental condition of a subject, such as a disease or syndrome.

It should be understood that symptoms and signs are associated with disorders. It should also be understood that a health care provider can diagnose a disorder by evaluating, detecting or recognizing symptoms and signs.

The terms "right" and "left," as used herein to describe a subject or an anatomical part, will refer to the side or position based on the perspective of the subject, not the viewer of the subject. For example, if a subject's eyes are illustrated in a drawing sheet, the right eye would be the eye on the left side of the drawing sheet.

The terms "including," "having," "comprising," "such as," "e.g.," similar terms, and the different forms of such terms are non-limiting terms for purposes of this disclosure. For example, "including" indicates "including, but not limited to," and "includes" indicates "includes, but is not limited to."

At times, the medical assembly 110 or parts thereof (e.g., the wearable device 124) may be described herein as performing certain functions, steps or activities. It should be understood that such performance depends, at least in part, on the medical system 114, the system data 125 or a combination thereof.

This disclosure includes examples of various embodiments, medical tests, medical analysis procedures, medical data, and inputs and outputs involving or related to the operation of the medical assembly 110. It should be understood that these are non-limiting examples. In some cases, these examples include dummy data used to explain a concept or principle of operation of the medical assembly 110. None of the examples in this disclosure should be construed to limit this disclosure to the details, particularities or scope of such examples.

2. Anatomical Parts and Anatomical Functions

The description provided in this section (Anatomical Parts and Anatomical Functions) includes a description of anatomical parts and anatomical functions that relate to the use, operation or implementation of the medical assembly 110 or examination output 127.

Extraocular Muscles. Extraocular muscles are the extrinsic eye muscles control the position of the eyes. Three pairs of extraocular muscles move each eye in three directions: vertically (superior and inferior), horizontally (medial and lateral), and torsionally (intorsion when the eye rotates toward the patient's nose and extorsion when the eye rotates toward the patient's shoulder).

Ocular Nerves. Extraocular muscles are innervated by three nerves: cranial nerve III (i.e., oculomotor nerve), cranial nerve IV (i.e., trochlear nerve) and cranial nerve VI (i.e., abducens nerve). Abducens nerve innervates lateral rectus muscle, which is responsible for abduction of the eye. Trochlear nerve innervates superior oblique muscle, which is responsible for adduction, depression and intorsion of the eye. Oculomotor nerve innervates all other extrinsic eye muscles. In addition, the oculomotor nerve innervates the muscle that raises the eyelid, and the intrinsic eye muscles that enable pupillary constriction and accommodation (ability to focus on near objects as in reading). All of these nerves originate from nuclei in the cephalad part of the brain known as the brainstem. These nuclei receive input from higher brain centers and from the inner ear balance center. These nuclei provide output through the ocular nerves to the muscles identified above.

Ductions. A duction is an eye movement involving only one eye. Movement of the eye nasally is adduction, and temporal movement is abduction. The eye can undergo elevation, known as supraduction, and the eye can undergo depression, known as infraduction. Incycloduction (intorsion) is nasal rotation of the vertical meridian, and excycloduction (extorsion) is temporal rotation of the vertical meridian.

Versions. Versions are movements of both eyes in the same direction, such as, for example, a right gaze in which both eyes move to the right. To test versions, a subject is asked to fixate on a target which is then slowly moved laterally. Once in lateral position, the target is moved superiorly and then inferiorly. The same is then repeated in contralateral gaze.

Vergence. A vergence is the simultaneous movement of both eyes in opposite directions to obtain or maintain single binocular vision. Convergence and divergence may be tested by the slow movement of the fixation target in toward the nose and outward, respectively.

Accommodation Reflex. Accommodation reflex (e.g., accommodation-convergence reflex) is a reflex action of the eye in response to focusing on a near object, then looking at a distant object (and vice versa). This reflex includes coordinated changes in vergence, lens shape (accommodation) and pupil size.

Pupillary Light Reflex (PLR). Pupillary light reflex (e.g., photopupillary reflex) is a reflex that controls the diameter of the pupil, in response to the intensity (luminance) of light that falls on the retina in the back of the eye. This reflex assists with the adaptation of vision to various levels of lightness and darkness. Light shone into one eye will cause both pupils to constrict due to the direct (ipsilateral pupils) and consensual (contralateral) effect of the light reflex.

Vestibulo-Ocular Reflex. The vestibulo-ocular reflex (VOR) causes involuntary eye movement in response to movement of the head. This allows visual images to remain stable despite head movement. The function of the VOR depends on the integrity of the connection of the vestibular system and the eye movement centers. The VOR serves to maintain foveation during head acceleration. The VOR is essential for clear vision during many common activities, such as walking or riding in a car.

Saccades. Saccades are the primary eye movements used in the visual exploration of the environment, including rapid movement of the eyes in a conjugate fashion to foveate targets of interest (i.e., the area that is the target of the fovea of the retina, which is the area responsible for sharp central vision). Saccades may be volitional, triggered involuntarily by the head (e.g., fast phases of vestibulo-ocular reflex), or triggered involuntarily by environmental movement (e.g., fast phases of optokinetic response). Saccades are of short duration.

Pursuit. The pursuit system functions to maintain foveation of a moving object. The primary stimulus for smooth pursuit is target motion across the retina. In other words, smooth pursuit movements are tracking movements of the eye conducted to keep a moving object or stimulus on the fovea of the retina. Such movements are under the voluntary control of the subject in the sense that the subject can choose whether or not to track a moving stimulus. As described below, pursuit abnormalities can include lack of pursuit and interrupted chopped pursuit known as saccadic pursuit.

3. Symptoms

The description provided in this section (Symptoms) includes a description of a non-limiting list of symptoms related to or applicable to the use, operation or implementation of the medical assembly 110 or examination output 127.

Vertigo. Vertigo is a symptom based on an illusion of movement or disequilibrium (tilting), either of the external world revolving around the subject or of the subject revolving in space. Vertigo is the primary symptom associated with nystagmus. Vertigo is a symptom of illusory movement. Vertigo is a symptom, not a diagnosis. Almost everyone has experienced vertigo as the transient spinning dizziness immediately after turning around rapidly several times. Vertigo can also be a sense of swaying or tilting. Some perceive self-motion, and others perceive motion of the environment. The most common motion illusion is a spinning sensation. Vertigo arises because of abnormal asymmetry in the vestibular system due to damage to or dysfunction of the labyrinth, vestibular nerve, or central vestibular structures in the brainstem. A physical examination should evaluate for vestibular dysfunction and distinguish central causes from peripheral causes of vertigo. The differentiation is critical because peripheral cases can be benign and self-remitting, while central causes may include life-threatening conditions, such as stroke. Peripheral disorders that cause vertigo include, but are not limited to, benign paroxysmal positional vertigo, vestibular neuritis, herpes zoster oticus (Ramsay Hunt syndrome), Meniere disease, labyrinthine concussion, perilymphatic fistula, semicircular canal dehiscence syndrome, Cogan's syndrome, recurrent vestibulopathy, acoustic neuroma, aminoglycoside toxicity and otitis media. Central disorders that cause vertigo include, but are not limited to, vestibular migraine, brainstem ischemia, cerebellar infarction and hemorrhage, Chiari malformation, multiple sclerosis and episodic ataxia type 2.

Other Nystagmus-Related Symptoms. In addition to vertigo, which is associated with associated with nystagmus, there are a variety of other symptoms associated with nystagmus, including, but limited to, the following:

(a) Oscillopsia. Oscillopsia is a to-and-fro illusion of environmental motion. Depending upon the nystagmus, this may be continuous, intermittent, or gaze-evoked.

(b) Blurred Vision. Blurred vision is a symptom that occurs because the retinal image is smeared by stimulus motion.

(c) Abnormal Head Positions. Subjects may assume abnormal head positions to compensate for their oscillopsia or blurred vision. The abnormal head positions can make the impaired vision less troublesome in certain gaze positions that minimize nystagmus.

Diplopia. Diplopia (i.e., double vision) is a visual symptom in which a single object is perceived by the visual cortex as two objects rather than one. Diplopia is a common visual concern that may be the first warning of vision-threatening or life-threatening neurologic disease. Diplopia may be binocular or monocular. Monocular diplopia is present if the diplopia occurs when either eye is closed. This is typically caused by local eye disease or refractive error, and not the result of disorder in eye motility. Binocular diplopia is present with both eyes open and absent when either eye is closed. Binocular diplopia reflects conditions in which the visual axes are misaligned. Binocular diplopia is usually the result of impaired function of the extraocular muscles, where both eyes are still functional, but they cannot turn to target the desired object. Problems with these muscles may be due to mechanical problems, disorders of the neuromuscular junction, disorders of the cranial nerves (III, IV, and VI) that innervate the muscles, and occasionally disorders involving the supranuclear oculomotor pathways (the central brain centers responsible for controlling or coordinating eye movements). In some cases, diplopia occurs in patients with full or near-full motility of both eyes but whose eyes are nevertheless misaligned. This suggests congenital strabismus but can be seen also if the limitations in motility are subtle and the health care provider is unable to detect a difference in between both eyes.

4. Disorders

The description provided in this section (Disorders) includes a description of a non-limiting list of disorders related to or applicable to the use, operation or implementation of the medical assembly 110 or examination output 127.

Nervous System Disorders. Eye abnormalities can be caused by nervous system disorders, including eye muscle disease, lesions, vestibular disease or syndrome, optic nerve damage or disease, pseudotumor cerebri (PTC) or elevated cranial pressure, optic neuritis or inflammation of the optic nerve, trauma, cerebrovascular disease, stroke, tumors, idiopathic intracranial hypertension (IIH) and giant cell arteritis.

Disorders that Result in Strabismus and/or Diplopia.

(a) Supranuclear Disorders. Supranuclear disorders involve brain centers above the nuclei of ocular nerves. These brain centers may be affected by a plurality of pathologies including demyelinating (such as multiple sclerosis), cerebrovascular (stroke), inflammatory, toxic (such as alcohol), nutritional deficiencies, neoplastic (i.e. cancer-related) and others. Some of these pathologies produce a certain type of eye misalignment, including the following:
  (i) Asymmetric Input to Ocular Motor. Eye misalignment can be caused by asymmetric input from the otolithic pathways (inner ear balance center) to the ocular motor neurons in the midbrain. This pathology can be caused by a central pathology, such as cerebrovascular disease (stroke).
  (ii) Internuclear Ophthalmoplegia. Internuclear ophthalmoplegia (INO), the disruption of horizontal gaze, causes horizontal or oblique diplopia, difficulty tracking moving objects, or transient blurred vision with sudden shifts in lateral gaze. Extraocular motility demonstrates slowed or impaired adduction of the affected eye, while the contralateral eye may show nystagmus in abduction and ocular dysmetria. It occurs due to disruption of the connection between the ocular nuclei, and results in the subject's inability to coordinate eye movements in certain gazes.
  (iii) Vertical One-and-a-Half Syndrome. Vertical one-and-a-half syndrome is the disruption of vertical gaze.
  (iv) Divergence Insufficiency and Paralysis. Divergence insufficiency and paralysis is an ocular motor anomaly characterized by horizontal diplopia in the distance, and is due to insufficient outward movement of the eyes during divergence.
  (v) Convergence Insufficiency and Paralysis. Convergence insufficiency and paralysis is a relatively common cause of diplopia at near sight in children and adults. Its findings include outward deviation greater at near than at a distance, and its findings also include a remote near point of convergence of greater than 6 to 8 cm.
  (vi) Other Disorders. Other disorders can cause eye misalignment, such as paroxysmal superior rectus and levator palpebrae spasm with multiple sclerosis, spasms of the near reflex, motor fusion deficiency, cyclic or periodic esotropia, thalamic esotropia, supranuclear monocular elevation paresis and other supranuclear disorders.

(b) Ocular Motor Nerve Dysfunction. Ocular nerves may be damaged at their level of origination (at the nuclei), or distally during their course. Third, fourth and sixth nerves palsies are relatively common, and they cause misalignment and diplopia that vary based on the affected nerves. These nerves may be affected by a plurality of pathological conditions such as trauma, ischemia, migraine, acute neuropathies (such as Fisher's syndrome and Guillain-Barré syndrome), congenital (such as Duane retraction syndrome), Wernicke's syndrome (caused by vitamin B1 deficiency and typically associated with alcohol abuse, which can result in diplopia and nystagmus) and others. Cover tests, described below, helps reveal subtle conditions where ocular misalignment is not manifest. Tests that evaluate pupillary light reflex and the eyelid drooping (ptosis) is helpful in delineating and differentiating some of these conditions.

(c) Neuromuscular Junction Diseases. Myasthenia gravis and botulism may affect the transmission between the nerves and extrinsic ocular muscles resulting in eye misalignment and diplopia.

(d) Diseases of Eye Muscle. There are six extrinsic muscles surrounding each eye, and plurality of conditions can affect these muscles individually or collectively leading to ocular misalignment, which can be non-specific or specific to a certain condition. These muscular-related disorders include congenital strabismus syndromes, thyroid eye disease (Grave's disease), chronic progressive external ophthalmoplegia syndromes, ocular myositis (i.e. inflammation of muscles), ocular myopathies, congenital or acquired isolated muscle weaknesses, decompensation of a long-standing phoria, post-surgical complications and others.

(e) Mechanical Processes Causing Eye Misalignment. Mechanical processes that cause eye misalignment are pathological conditions that mechanically restrict eye movements, causing eye misalignment. These conditions can include thickening of the muscle tendon's sheath (Brown's superior oblique tendon sheath syndrome), orbital floor fracture, post-surgical sequela, fibrosis of the muscles, orbital inflammation (orbital pseudotumor), orbital tumors, fallen eye syndrome (hypodeviation of the non-paretic eye caused by contracture of the contralateral inferior rectus muscle experienced by a subject with long-standing superior oblique muscle paresis who habitually fixates with the paretic eye), rising eye syndrome (contracture and fibrosis of the contralateral superior rectus muscle experienced by a subject having long-standing inferior oblique muscle palsy), and others.

Other Disorders. Eye abnormalities can be caused by other disorders, including hypertension, diabetes, cardiac atherosclerotic disease, cardiovascular disease, multiple sclerosis, autoimmune disease, infection, inflammation, toxicity, and habits such as smoking, alcohol and substance abuse.

5. Eye Abnormalities

The description provided in this section (Eye Abnormalities) includes a description of eye abnormalities (including ophthalmological abnormalities) related to or applicable to the use, operation or implementation of the medical assembly 110 or examination output 127.

Nystagmus.

(a) Nystagmus, involuntary movements of the eye, is an eye abnormality. There are various types of nystagmus. Nystagmus is a rhythmic regular oscillation of the eyes. It may consist of alternating phases of a slow drift in one direction with a corrective quick "jerk" in the opposite direction, or of slow, sinusoidal, "pendular" oscillations to and fro. Nystagmus can be continuous or paroxysmal, or evoked by certain maneuvers such as specific gaze or head positions. Nystagmus can be vertical, horizontal, torsional, convergence-divergence or a mix of these.

(b) A mixed horizontal-torsional jerk nystagmus results if a peripheral lesion affects all three semicircular canals or the vestibular nerves on one side. The horizontal fast phases beat toward the normal ear, as do the upper poles of the eyes for the torsional fast phases. The jerk nystagmus from peripheral disease occasionally appears purely horizontal, but it is has not been observed to occur purely torsional or vertical. Also, pendular nystagmus has not been observed to occur due to peripheral vestibular disease. The jerk nystagmus with central lesions may have any trajectory.

(c) Visual fixation tends to suppress nystagmus that is due to a peripheral lesion, but it does not usually suppress nystagmus from a central lesion. It may be useful to inhibit visual fixation to test whether the nystagmus is central or peripheral in origin. This is done in clinical practice by shining light in the examined eye to render the eye "blind."

(d) Testing nystagmus in different gaze positions can provide other localizing clues. In peripheral lesions, the predominant direction of nystagmus remains the same in all directions of gaze. Nystagmus that reverses direction when the subject looks right then left suggests a central abnormality. However, the absence of this characteristic does not rule out a central cause of vertigo. Nystagmus that reverses direction with convergence also suggests a central lesion.

(e) Some subjects with nystagmus are asymptomatic. Nystagmus may occur in a plurality of medical conditions, both congenital and acquired. Certain types of nystagmus can be specific to certain conditions, yet the majority are non-specific and may occur in a plethora of conditions. Detection of nystagmus is a part of standardized field sobriety test (FST) by police to gauge whether a driving-under-influence suspect is showing the typically-horizontal nystagmus that may be associated with alcohol consumption.

Saccadic Dysfunction. Dysfunctional saccadic intrusions and saccadic oscillations are involuntary spontaneous eye movements that begin with a rapid eye movement (saccade), taking the eyes away from the visual target. The amplitude can range from asymptomatic, small saccadic intrusions to large, saccadic oscillations causing severe oscillopsia. Saccadic dysfunctions or abnormalities can be divided into abnormalities of initiation (long latency), speed (slow saccades), absent or unwanted saccades, and accuracy (hypometric or hypermetric saccades).

Abnormal Vestibulo-Ocular Reflex. As described below, tests can be conducted to determine whether the VOR is abnormal.

Skew Deviation. Skew deviation, an eye abnormality, is a vertical misalignment of the two eyes resulting from a supranuclear (relative to the ocular motor nuclei) pathology. Skew deviation is associated with a vertical and occasionally torsional binocular diplopia. This pathology is usually located in the brainstem. However, skew deviation can be caused by a vestibular lesion because of imbalance in input from inner ears. It carries special importance as it is used with other findings to indicate a central pathology, such as cerebrovascular disease (stroke). As described below, tests can be conducted to detect skew deviation.

Abnormal Tilting. As a result of a stroke or other disorder, a subject may have an abnormal torsional tilt of the eyes with the upper poles tilted toward the eye that is lower. The subject may also have an abnormal tilting of the head toward the eye that is lower.

Strabismus. Strabismus is an eye abnormality in which the eyes do not properly align with each other when looking at an object. The eye that is focused on an object can alternate. The abnormality may be present occasionally or constantly. If present during a large part of childhood, it may result in amblyopia (decreased vision in the lazy eye), or loss of depth perception. If the onset is during adulthood, it is more likely to result in double vision. Strabismus can be manifest (-tropia) or latent (-phoria). A manifest deviation or heterotropia is present while the subject views a target binocularly with no occlusion of either eye. The subject is unable to align the gaze of each eye to achieve fusion. A latent deviation or heterophoria is only present after binocular vision has been interrupted, typically by covering one eye. A subject with this type of eye abnormality can typically maintain fusion despite the misalignment that occurs when the positioning system is relaxed. Intermittent strabismus is a combination of both of these types abnormalities, where the subject can achieve fusion, but occasionally or frequently falters to the point of a manifest deviation.

6. Tests for Eye Abnormalities

The description provided in this section (Tests for Eye Abnormalities) includes a description of eye tests related to or applicable to the use, operation or implementation of the medical assembly 110 or examination output 127.

Hearing Tests. Inner ear pathologies can commonly cause both vertigo and hearing impairment. Thus, detecting hearing loss may help point toward an eye dysfunction or peripheral etiology.

Head Impulse Test. A head impulse test evaluates the integrity of the connection of the vestibular system and the eye movement centers for evaluating the VOR. The VOR requires precise control, such that a 10-degree head movement induces an exactly 10-degree conjugate eye movement in order to maintain clear vision. Any error in this reflex results in significant blur with head acceleration. The examination hallmark of the VOR hypofunction is an abnormal result of a head impulse test. To perform the head impulse test, the health care provider can move the subject's head rapidly (but only in small amplitude) while the subject is viewing a stationary target. The health care provider can then assess the ocular response. If the VOR is intact, the subject's eyes will remain on the target. If the VOR is abnormal, the subject's eyes will have moved off the target, and the subject would have attempted a catch-up saccade to refoveate the target.

Skew Deviation Test. Different tests can be conducted to detect skew deviation, including have the subject fixate on a central target, cover one eye, and then rapidly uncover the eye and assess whether the eye moves to re-align. This test can be repeated with the other eye.

Cover Tests. Cover tests can be used to indicate tropia (manifest strabismus) or phoria (latent strabismus).

Cover-Uncover Test. The cover-uncover test differentiates a tropia from a phoria. First, one eye is occluded (i.e., covered or blocked) while the subject is fixating on a target. If the fellow eye shifts to pick-up fixation, it must have been deviated prior to occlusion of the other eye, and one can conclude that a tropia is present. If, however, the fellow eye does not shift, but instead the occluded eye moves in the direction of weakness while covered (noted as the eye returns to fixation after the occluder is removed), a phoria is present. In either case, the type of tropia or phoria can be determined by noting the direction of refixation of the deviated eye.

Alternate Cover Test. By alternating which eye is covered, the health care provider can bring out phorias and tropias, and can quickly determine the direction of deviation. For this test, the health care provider occludes one eye and then the other, switching the occluder back and forth to occlude the eyes without allowing the subject to fuse in between occlusion. The alternate cover test is a relatively extensive dissociative cover test. This test measures a total deviation, including the tropic plus the phoric/latent component. When performing this alternate cover test, it is important to hold the occluder over each eye for at least a few seconds, in order to allow the non-occluded eye enough time to pick-up fixation. In general, the faster the eyes are able to recover when the occluder is switched, the better the control of the deviation. Even when misalignment is the result of unilateral eye weakness, both eyes will move when uncovered during the alternate cover test. This results from the Hering law of equal innervation, which states that an equal force must be supplied to both eyes. The health care provider can perform the alternate cover test in the nine cardinal fields of gaze to look for changes in the degree of refixation. When the subject is gazing in the direction of an eye's weakness, the movements will be greater.

Dissociating Tests. A dissociating test is a test that presents dissimilar objects for each eye to view, so that the images cannot be fused. A commonly used dissociating test is the Maddox rod test. A Maddox rod is a red lens with multiple aligned prisms that will convert a white light into a red line. During testing, the lens is held over the right eye (by convention), while a light is shined at the subject. The left eye will see the white light, but the right eye will see a red line, which can be horizontal (to test vertical alignment) or vertical (to test horizontal alignment). Thus, akin to covering one eye, stereo fusion is disrupted, and phorias will emerge. Phoria or tropia will result in the red line being separate from the white light, by a degree that is proportional to the degree of the phore or tropia. Thus, the Maddox rod test can quantify the degree of the diplopia and dictate the prism diopter required in the subject's glasses for correction of the diplopia.

Head-Impulse-Nystagmus-Test of Skew Test. A composite, three-part test entitled Head-Impulse-Nystagmus-Test of Skew (HINTS) is an examination that includes the head impulse test, evaluation for direction-changing (gaze-evoked) nystagmus, and the presence of skew deviation. The presence of any one of three clinical signs (a normal head impulse test, direction-changing nystagmus, or a skew deviation) suggests cerebrovascular disease (e.g., stroke) rather than peripheral vertigo in subjects with an acute sustained vestibular syndrome. When properly conducted, this test can have higher sensitivity than the use of magnetic resonance imaging (MRI) of the brain for detecting stroke.

Ocular Tilt Reaction Test. The ocular tilt reaction test (OTR) is an examination for a triad of the following eye abnormalities: skew deviation, torsional tilt of the eyes with the upper poles tilted toward the eye that is lower, and head tilt toward the eye that is lower. This triad of abnormalities is typically caused by a stroke.

Head-Shaking Test. To test for and attempt to elicit nystagmus, the subject can shake the head from side to side for 15 to 40 seconds while the eyes are closed. When the shaking stops, the subject then opens the eyes and attempts to look straight ahead. In normal individuals, no nystagmus will be observed. If nystagmus occurs, it indicates a peripheral or central etiology for the vertigo, and it helps pointing to the left or right side.

Caloric Test. To test for and attempt to elicit nystagmus, the health care provider can infuse warm or cold water into the external ear canal. For normal individuals, this would result in nystagmus. The direction of the nystagmus depends on whether cold or warm water was used. Lack of nystagmus is a sign of an abnormality in the vestibular system.

Specialized Postural Maneuver Tests. Specialized postural maneuvers, such as the Dix-Hallpike maneuver and head-roll maneuver, can be conducted to reproduce vertigo and elicit nystagmus in subjects with a history of positional dizziness. In subjects with otolithic formation (i.e., inner ear debris or particles), the sudden movement can move the debris into inner ear structures responsible for rotatory movement detection, called semicircular canals. This will result in vertigo and nystagmus. This condition or symptom is known as benign paroxysmal positional vertigo (BPPV). Dix-Hallpike or head-roll maneuvers aim to reproduce the nystagmus. The characteristics of the nystagmus are observed (direction of the nystagmus, latency to begin after the maneuver, transience to remit and fatigability of nystagmus if repeated), and used to determine if BPPV is present based on certain criteria.

Other Specialized Maneuver Tests. Other maneuvers, such as hyperventilation and Valsava maneuver (i.e., forceful exhalation against closed airways), can elicit certain types of vertigo or nystagmus, such as Chiari-related nystagmus or endolymph fistula-related nystagmus.

7. Electronic Architecture

Referring to FIGS. 1-2, in an embodiment, the primary and secondary data storage devices 116, 122 each include a memory device or other physical medium configured to store data, including one or more disks, memory chips, integrated circuits and semiconductor cells. The processor 120 includes a data processor, microprocessor, central processing unit (CPU), graphical processing unit (GPU) or electronic circuitry configured for executing instructions of a computer program or software.

Figure 3:
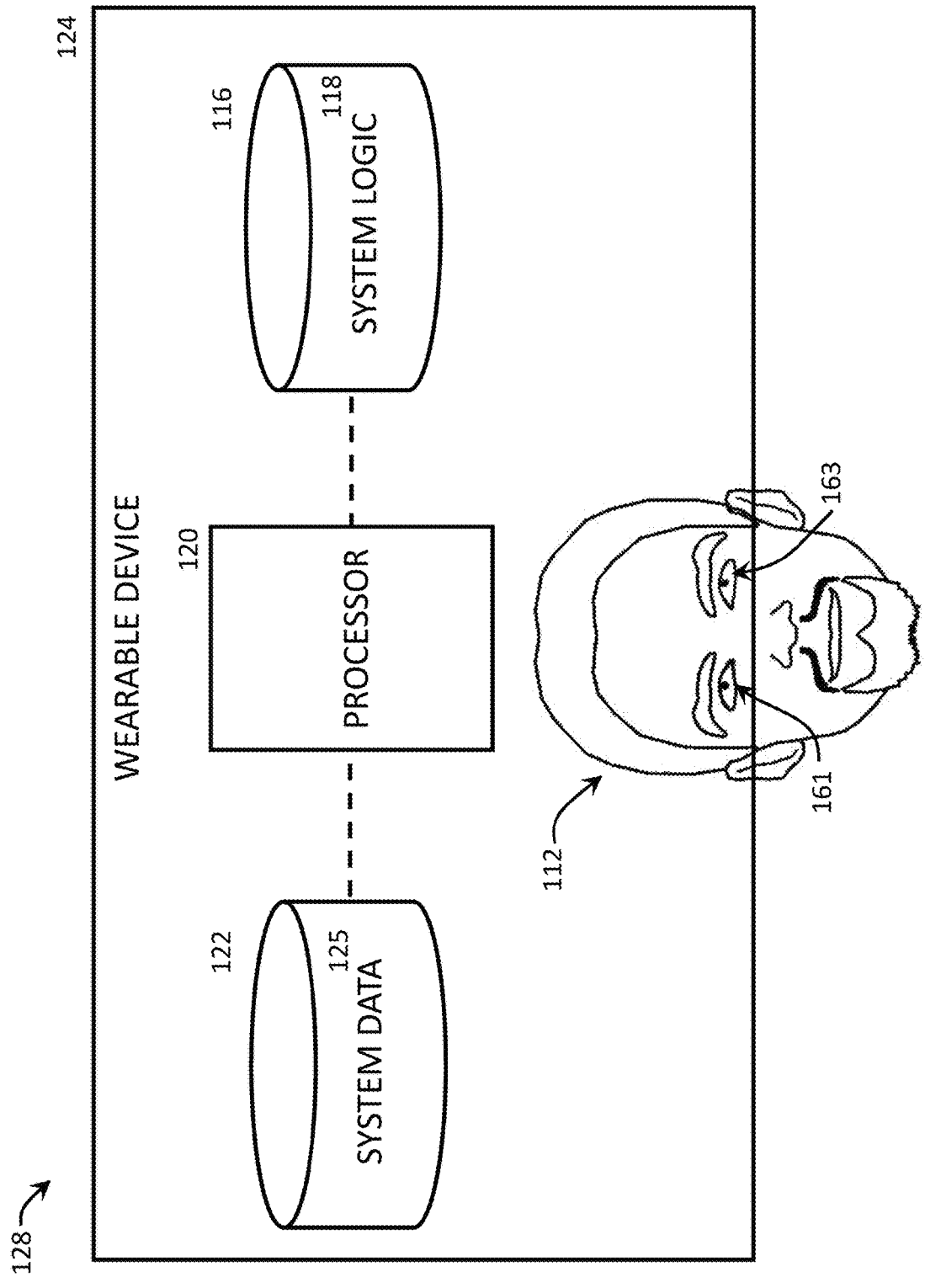
FIG. 3 is a schematic diagram illustrating a device-centric architecture of the medical assembly of FIG. 1.
Figure 4:
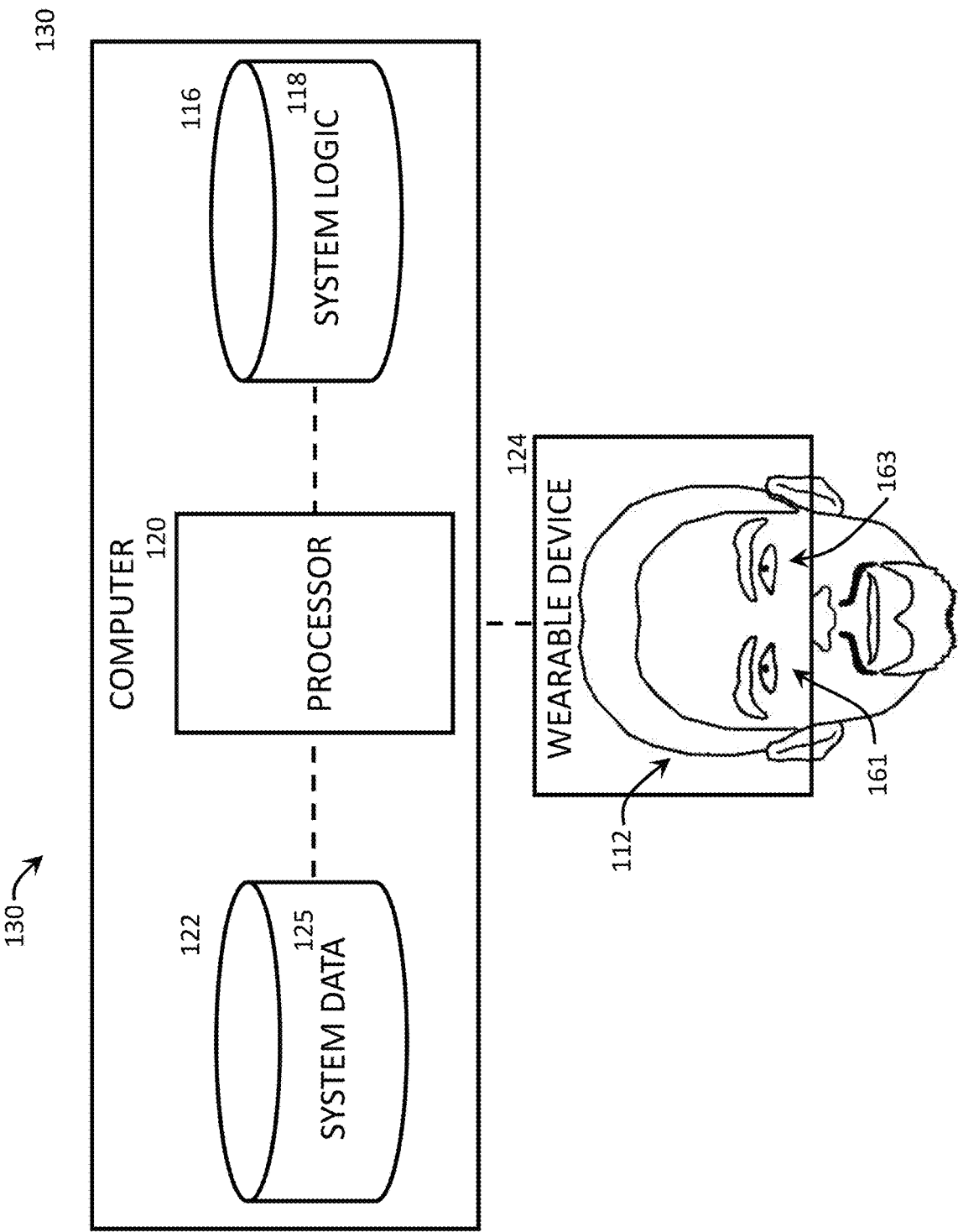
FIG. 4 is a schematic diagram illustrating a computer-centric architecture of the medical assembly of FIG. 1.

Depending on the embodiment, the medical assembly 110 can be arranged and configured in a plurality of different electronic architectures. In the device-centric architecture 128 shown in FIG. 3, the wearable device 124 incorporates the processor 120 and the primary and secondary data storage devices 116, 122. In the computer-centric architecture 130 shown in FIG. 4, a computer 130 incorporates the processor 120 and the primary and secondary data storage devices 116, 122. In such embodiment, the processor 120 is operatively coupled to the wearable device 124 through a wire-based or wireless electronic connection. The computer 130 can include a desktop computer, laptop, tablet, workstation or any other type of suitable computing hardware. In the server-centric architecture 132 shown in FIG. 5, a server 134 incorporates the processor 120 and the primary and secondary data storage devices 116, 122. The server 134 can include a webserver or any other device that is accessible over a data network 136, such as the Internet or another type of data communication pathway, as described below. According to the server-centric architecture 132, the wearable device 124 is operatively coupled to the server 134 through the network 136.

Figure 6:
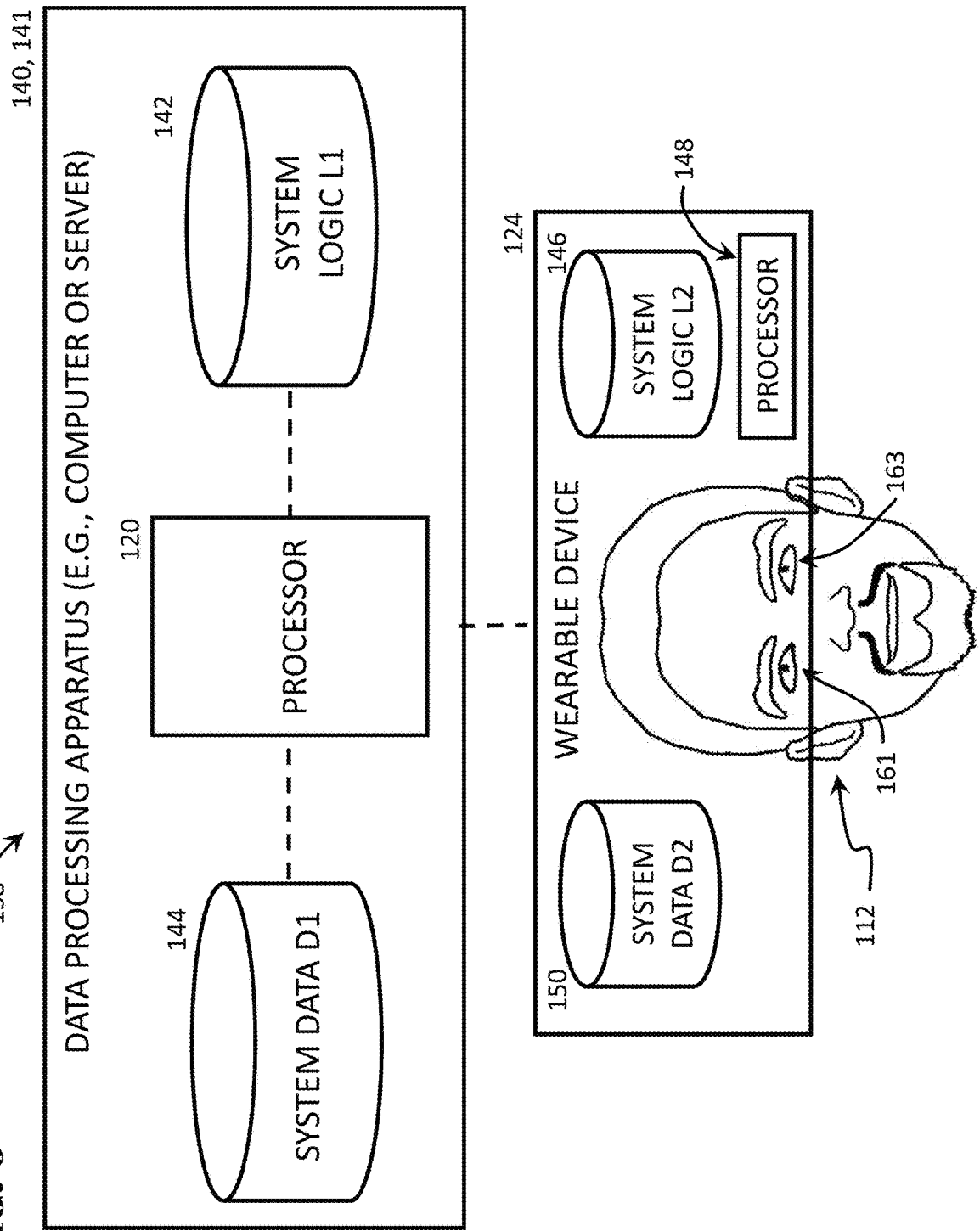
FIG. 6 is a schematic diagram illustrating a hybrid architecture of the medical assembly of FIG. 1.

In the hybrid architecture 138 shown in FIG. 6, a data processing apparatus 140 incorporates an L1 storage device 142, the processor 120, and a D1 storage device 144. In this embodiment, the wearable device 124 incorporates an L2 storage device 146, a device processor 148, and a D2 storage device 150. Depending on the embodiment, the data processing apparatus 140 can include the computer 130, the server 134 or a combination thereof. The wearable device 124 is configured to be operatively coupled to the data processing apparatus 140. Depending on the embodiment, the wearable device 124 can be operatively coupled to the data processing apparatus 140 through a wire-based, electronic connection or through a wireless, electronic connection. Also, the data processing apparatus 140 and the wearable device 124 can each be operatively coupled to the network 136. In that case, the wearable device 124 is operatively coupled to the data processing apparatus 140 through the network 136.

It should be appreciated that, depending on the embodiment, it is not necessary or mandatory for the medical assembly 110 to have multiple storage devices 116, 122, 142, 144, 146, 150. For example, a single data storage device could be used to store all of the data, logic and software of the medical assembly 110. In such embodiment, such single data storage device can have different memory registries for separately storing different types of data and software.

Figure 7:
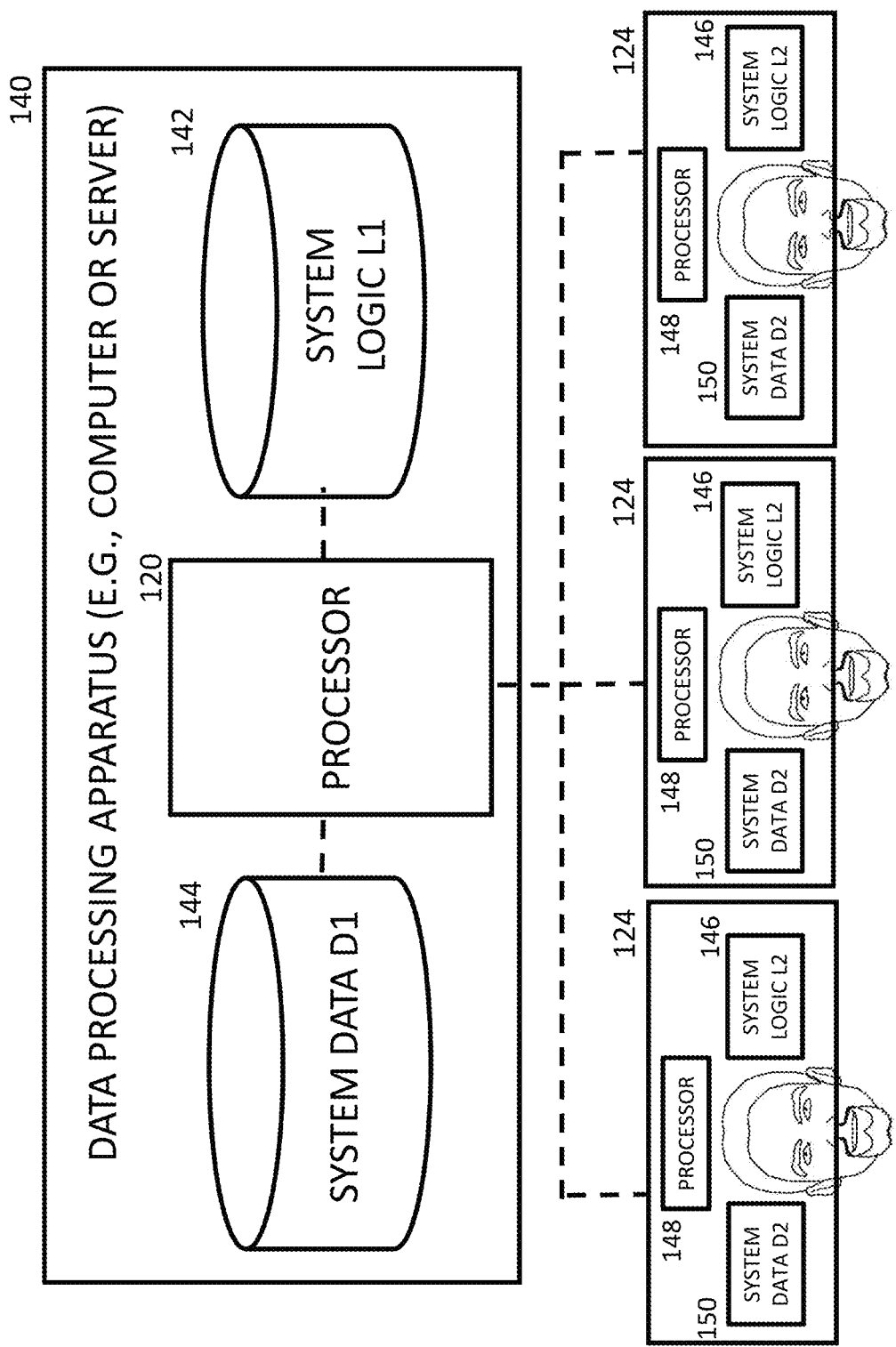
FIG. 7 is a schematic diagram illustrating an array of distributed units of wearable devices operatively coupled to the data processing apparatus of the medical assembly of FIG. 1.

As shown in FIG. 7, in an embodiment, the data processing apparatus 140 is operatively coupled to an array of wearable devices 124. Each of the wearable devices 124 can be owned by, leased to or otherwise used by a different subject. Accordingly, as wearable devices 124 are distributed throughout health care facilities and residences, a relatively high number of subjects can use the wearable devices 124 for eye examinations. The D1 storage device 144 can collect and store data based on the results of such eye examinations. As the D1 storage device 144 gains greater amounts of such data, the performance of the medical assembly 110 can be automatically optimized through artificial intelligence (AI), as described below.

Figure 8:
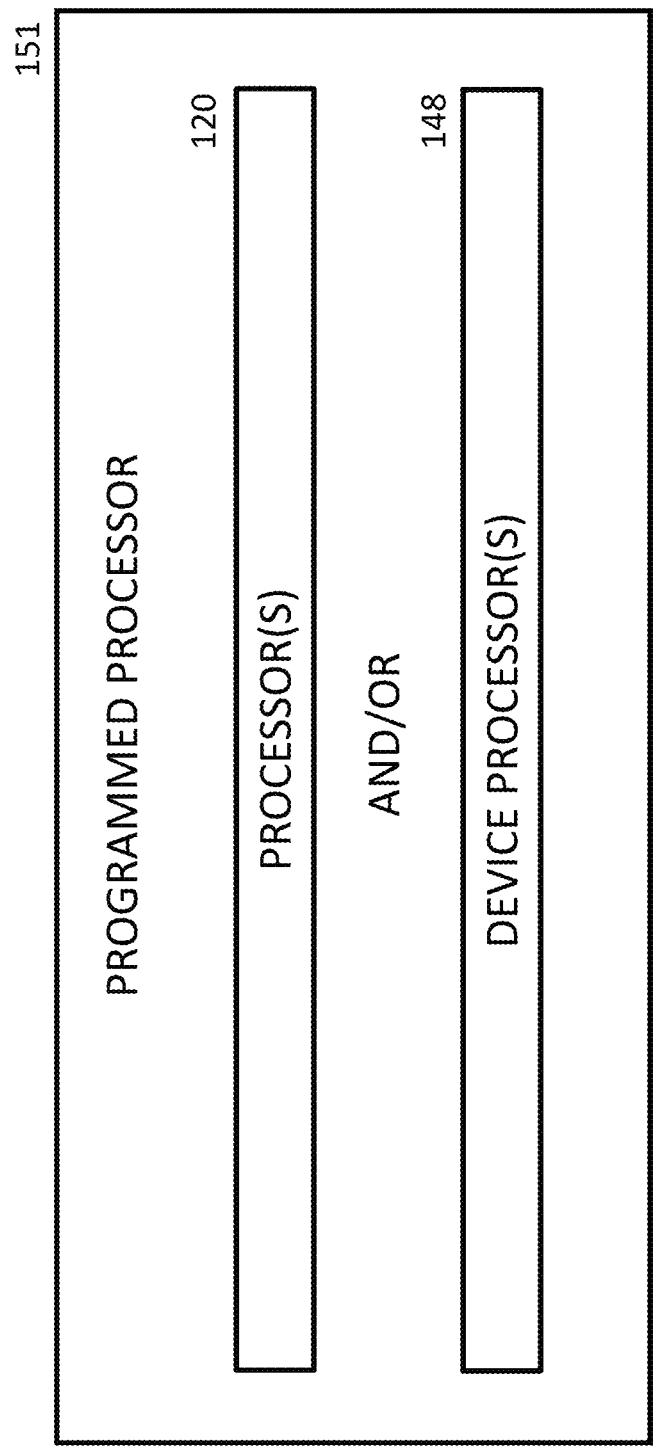
FIG. 8 is a schematic diagram illustrating an embodiment of a programmed processor of the medical assembly of FIG. 1.

As shown in FIG. 8, depending on the embodiment, the medical assembly 110 can be controlled or operated by one or more processors 120, by one or more device processors 148, or by a combination of one or more processors 120 and device processors 148. In either such embodiment, the one or more processors 120, 148, is operable in accordance with, and as programmed, the system logic 118. Such one or more processors 120, 148, referred to as a programmed processor 151, are configured to manage, control and process and input and output signals transmitting throughout the medical assembly 110.

Referring back to FIGS. 1-2, in an embodiment, the secondary data storage device 122 records or stores system data 125. In this embodiment, the system data 125 includes: (a) control data 152 formatted and structured for processing by the programmed processor 151, shown in FIG. 8, to control the inputs and outputs of the medical assembly 110, including the processing of input/output signals and the generation of audio, visual, audiovisual, vibratory, tactile and other outputs; (b) a plurality of sensed parameters 366 that are at least partially associated with, related to or derived from sensor signals generated by the wearable device 124; (c) a plurality of data files 155; (d) abnormality data 156 that specifies, corresponds to or is associated with different severities of eye abnormalities, as described below; and (e) medical analysis data 158 including diagnostic data, patient-specific historical data files and other health data that specifies, corresponds to or is associated with different possible diagnoses of disorders, as further described below and illustrated in FIG. 57.

The system logic 118, in an embodiment, includes a plurality of computer-readable instructions, software, computer code, object code, machine-readable code, computer programs, logic, data, data libraries, data files, graphical data and commands that are collectively formatted and structured to be executed by the programmed processor 151.

In the hybrid architecture 138, shown in FIG. 6, the system logic 118 is divisible into an L1 portion and an L2 portion, and the system data 125 is divisible into a D1 portion and a D2 portion. In an embodiment, the data processing apparatus 140 is a webserver 141, such as the App Store managed by Apple Inc., the Play Store managed by Google LLC, the Amazon App Store managed by Amazon.com, Inc., or another online platform managed by the manufacturer of the medical assembly 110 or another entity. In this embodiment, the webserver 141 originally stores the L1, L2, D1 and D2 portions. When setting-up the medical assembly 110, the user can download the L2 and D2 portions from the webserver 141 to the wearable device 124, establishing the arrangement shown in FIG. 6. In operation, the wearable device 124 functionally cooperates with the webserver 141 through: (a) the execution of the L1 and D1 portions by the processor 120; and (b) the execution of the L2 and D2 portions by the device processor 148.

8. Wearable Device

Figure 9:
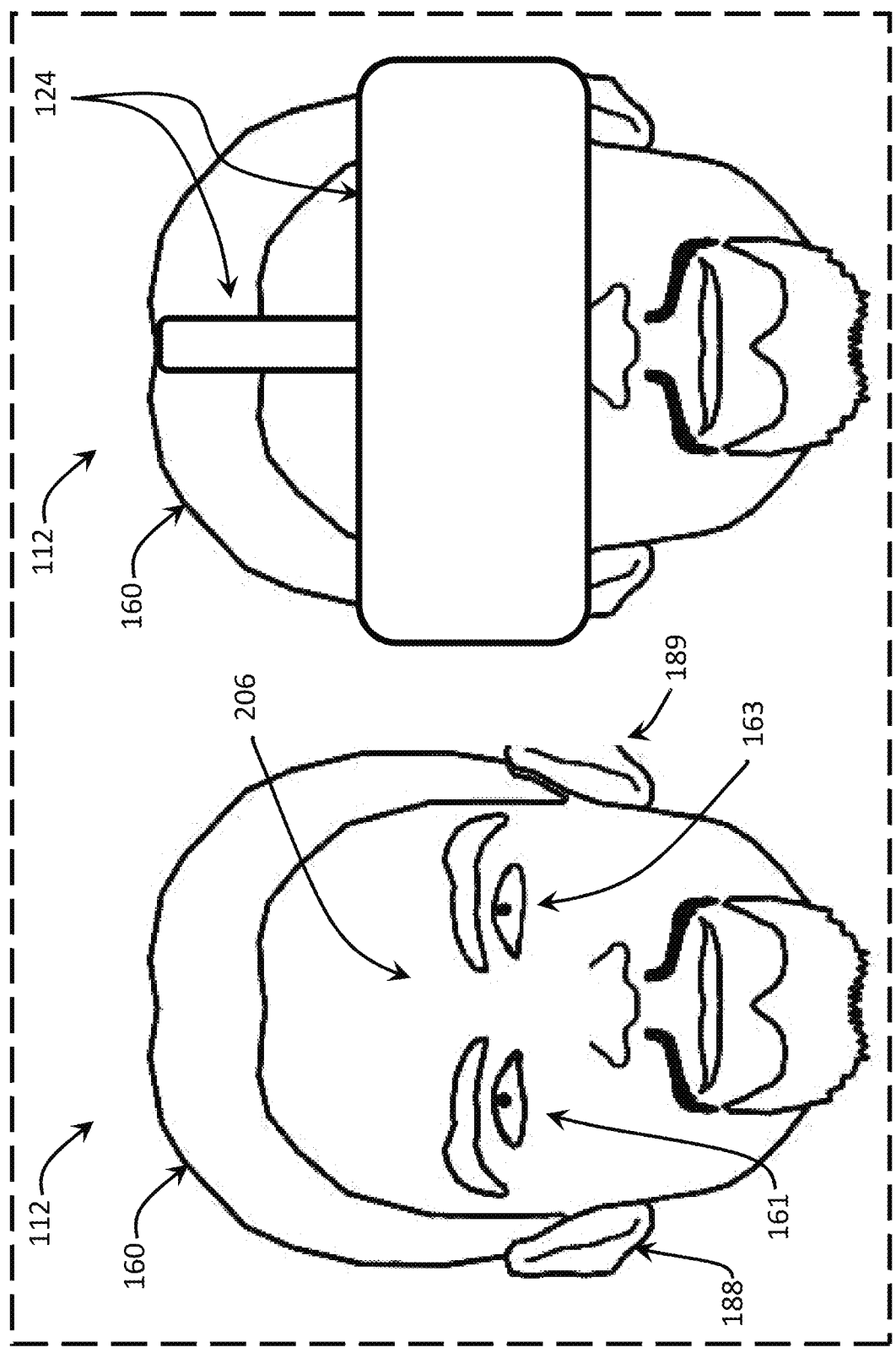
FIG. 9 is a front view of a subject with and without an embodiment of the wearable device worn on the subject's head.

Referring to FIG. 9, in an embodiment, the wearable device 124 includes a headset or headgear configuration that is shaped and sized to be worn on the head 160 of the subject 112. The wearable device 124 is configured to cover the right eye 161 and left eye 163 of the subject 112. When worn on the head 160, the wearable device 124, like a cap or helmet, is carried by the head 160 and moves corresponding to the movement of the subject's head 160. The mobility and wearability of the wearable device 124 provides a substantial improvement over conventional, stationary eye examination equipment placed on a floor or table. Such conventional equipment requires the patient to visit the facility where such stationary equipment is placed. In contrast, users can readily procure, transport and distribute units of the wearable device 124 with relative ease. The subject 112 can conveniently carry the wearable device 124 to any desired location for an eye examination.

Figure 10:
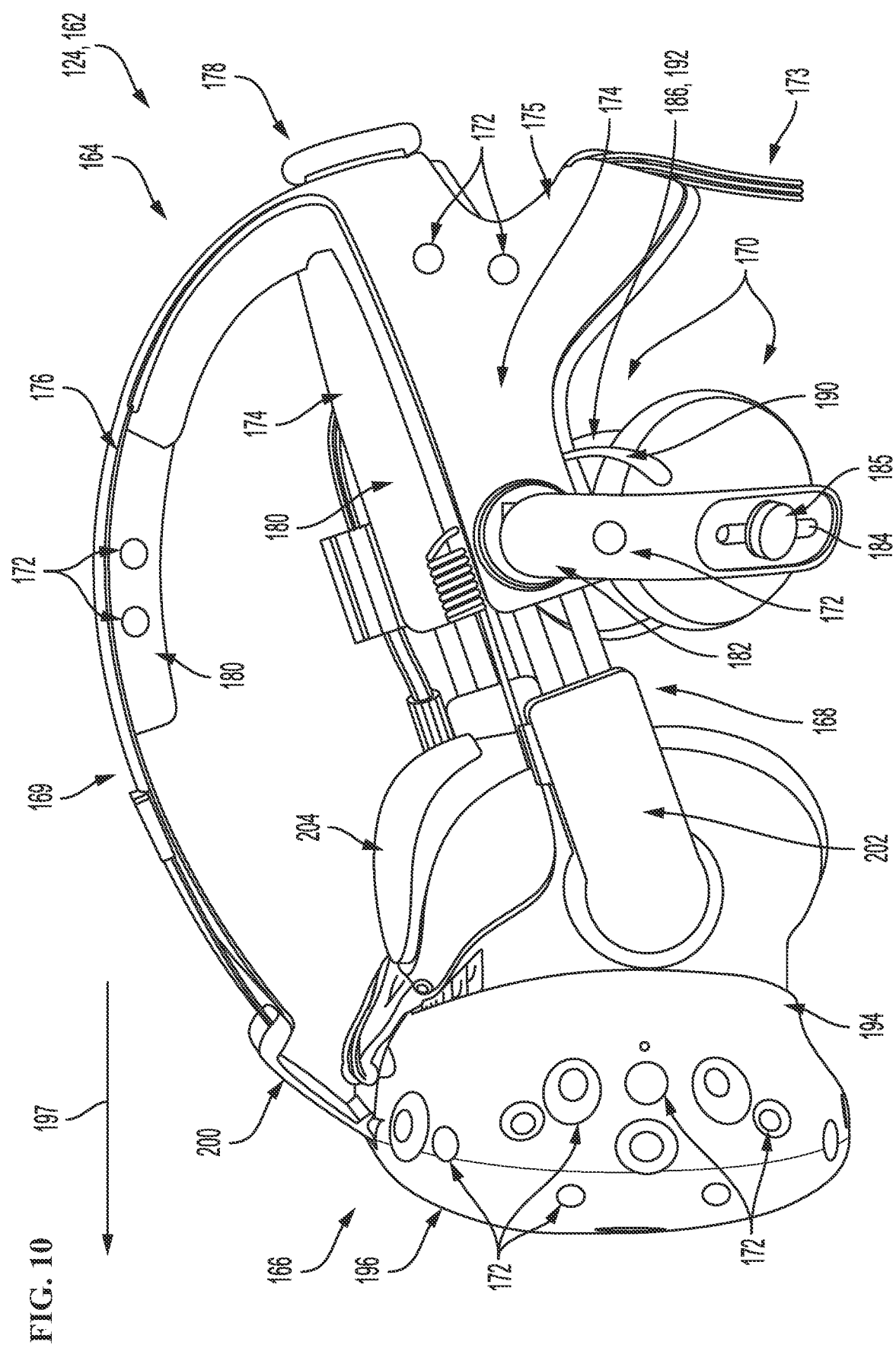
FIG. 10 is a side isometric view of an embodiment of a medical headset, which is an embodiment of the wearable device of the medical assembly of FIG. 1.

Referring to FIG. 10, in an embodiment, the wearable device 124 includes a medical headset 162 wearable on the head 160 of the subject 112. The medical headset 162 includes: (a) a head mount 164 having a concave shape configured to conform to the shape of the head 160 and couple to the rear of the head 160; (b) a face assembly 166; (c) an adjustable lower coupler 168 and an adjustable upper coupler 169, which collectively couple the face assembly 166 to the head mount 164; (d) a plurality of ear assemblies 170 adjustably coupled to the head mount 164; (e) a plurality of electrical or electronic sensors 172 coupled to, mounted to or positioned within the face assembly 166, the head mount 164, the ear assemblies 170 or a combination thereof; and (f) a cord assembly 173 electrically or electronically coupled to the face assembly 166, ear assemblies 170 and sensors 172.

In an embodiment, the head mount 164 includes: (a) a lower head support 175 extending downward to engage the base of the skull and part of the neck of the subject 112; (b) a plurality of side straps or side extensions 174, each of which is configured to extend at least partially around one side of the head 160; (c) a top strap or top extension 176 configured to extend at least partially around the top of the head 160; and (d) an adjustable securement device 178 moveably coupled to the rear of the head mount 164.

Each of the extensions 174, 176 is at least partially flexible having a semi-rigid or elastic characteristic. Each of the side extensions 174 defines an interior channel or passageway (not shown), which is configured to receive a segment of the lower coupler 168, enabling the lower coupler 168 to engage with the securement device 178. Also, each of the extensions 174, 176 has a comfort enhancer 180 configured to engage with the head 160. The comfort enhancer 180 includes a pliable or elastic member or layer, such as a suitable padding, foam, rubber or polymeric material.

In an embodiment, each of the ear assemblies 170 includes: (a) an ear extension 182 rotatably or pivotally coupled to one of the side extensions 174, which defines an ear adjustment slot 184; (b) an ear engager 186 configured to at least partially surround or partially insert into an ear of the subject 112 so that the right ear 188 and left ear 189 are each engaged with one of the ear engagers 186; (c) an ear coupler 185 configured to fit through the adjustment slot 184 and screw into the ear engager 186; (d) an ear phone or ear speaker (not shown) positioned at least partially within the ear engager 186; and (e) an electrical or electronic ear cord 190 operatively coupled to the ear speaker. The ear cord 190 is electrically coupled to the face assembly 166. By pivoting or adjusting the ear coupler 185 and by rotating the ear extension 182, the user can reposition the desired ear engager 186 to fit over the desired ear 188 or 189. The ear engager 186 has an ear comfort enhancer 192 configured to engage with the desired ear 188 or 189. The ear comfort enhancer 192 includes a pliable or elastic member or layer, such as a suitable padding, foam, rubber or polymeric material.

Referring to FIGS. 10-14, in an embodiment, the face assembly 166 includes: (a) a housing, cover or body 194, which includes a display unit holder 195 and a front surface 196 configured to face at least partially in a forward direction 197 away from the eyes 161, 163 of the subject 112; (b) a display unit 198 permanently, adjustably or removably held by the display unit holder 195; (c) a top harness 200 adjustably coupled to the upper coupler 169; (d) a plurality of side arms 202 (left and right), each of which is rotatably or pivotally coupled to the body 194; and (e) a face engager 204 configured to engage the face 206 of the subject 112 so as to cover both eyes 161, 163 of the subject 112.

Figure 11:
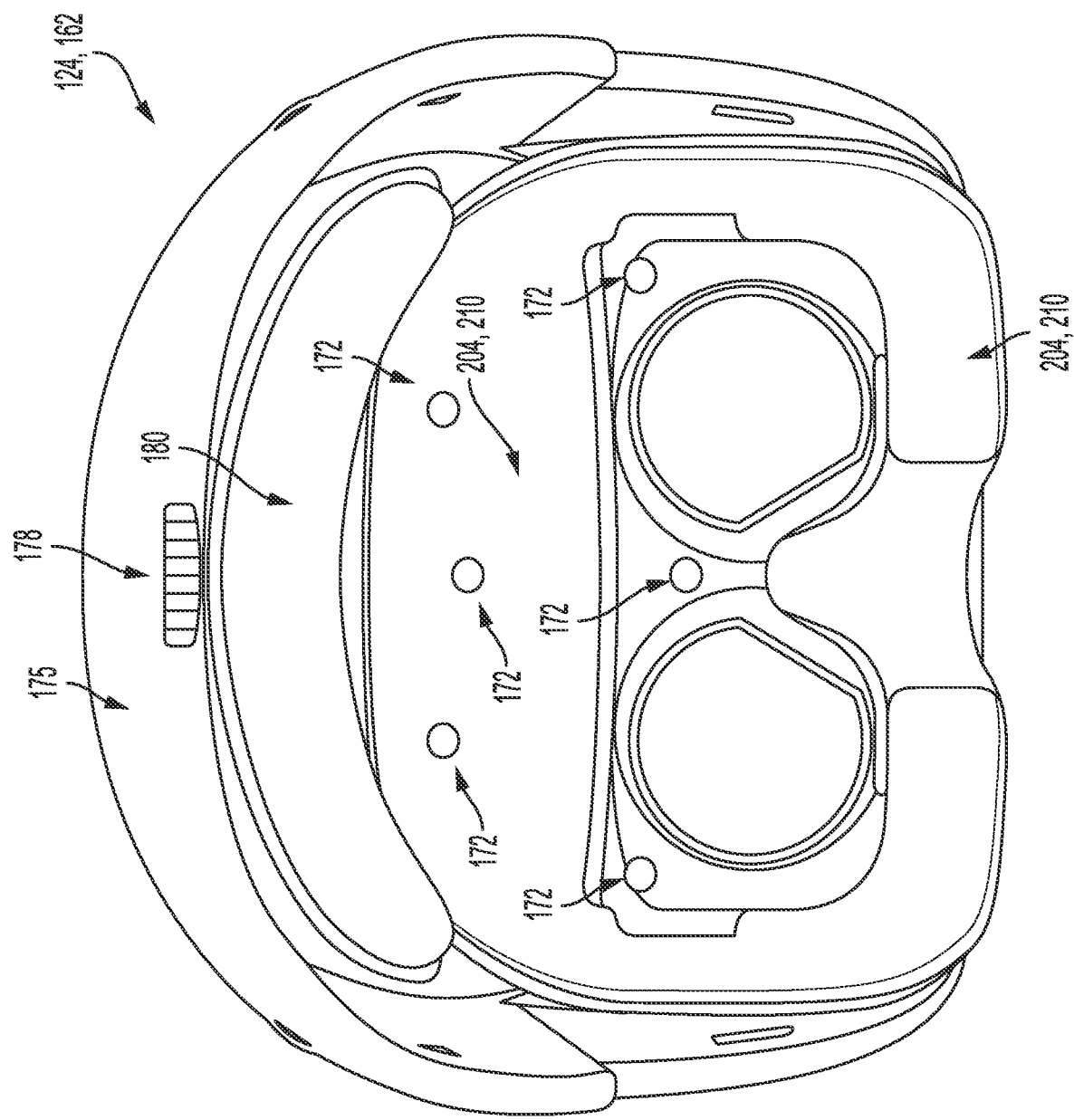
FIG. 11 is a rear view of the medical headset of FIG. 10.
Figure 12:
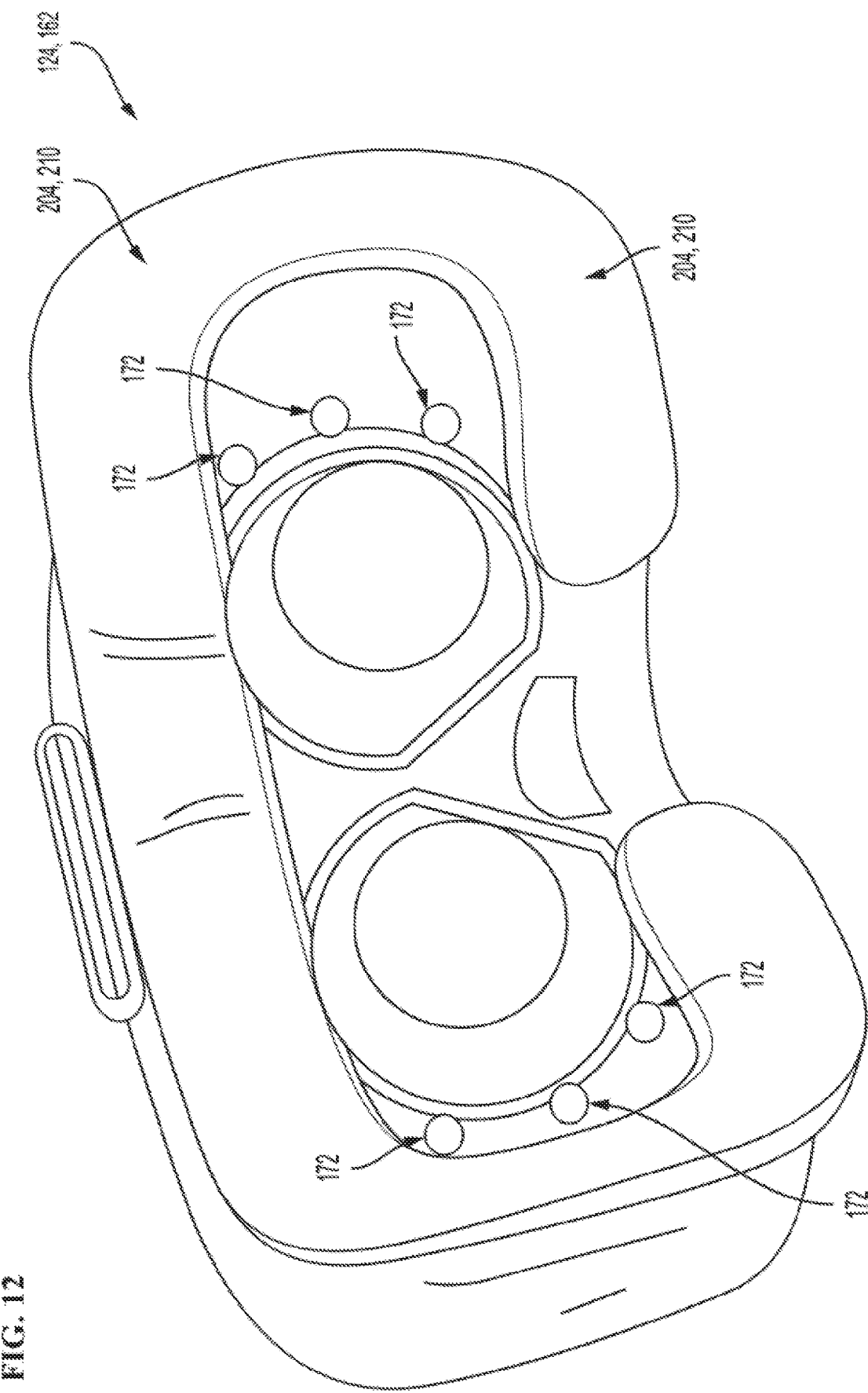
FIG. 12 is a rear isometric view of the medical headset of FIG. 10, illustrating a plurality of rearward-facing sensors and other sensors.
Figure 13:
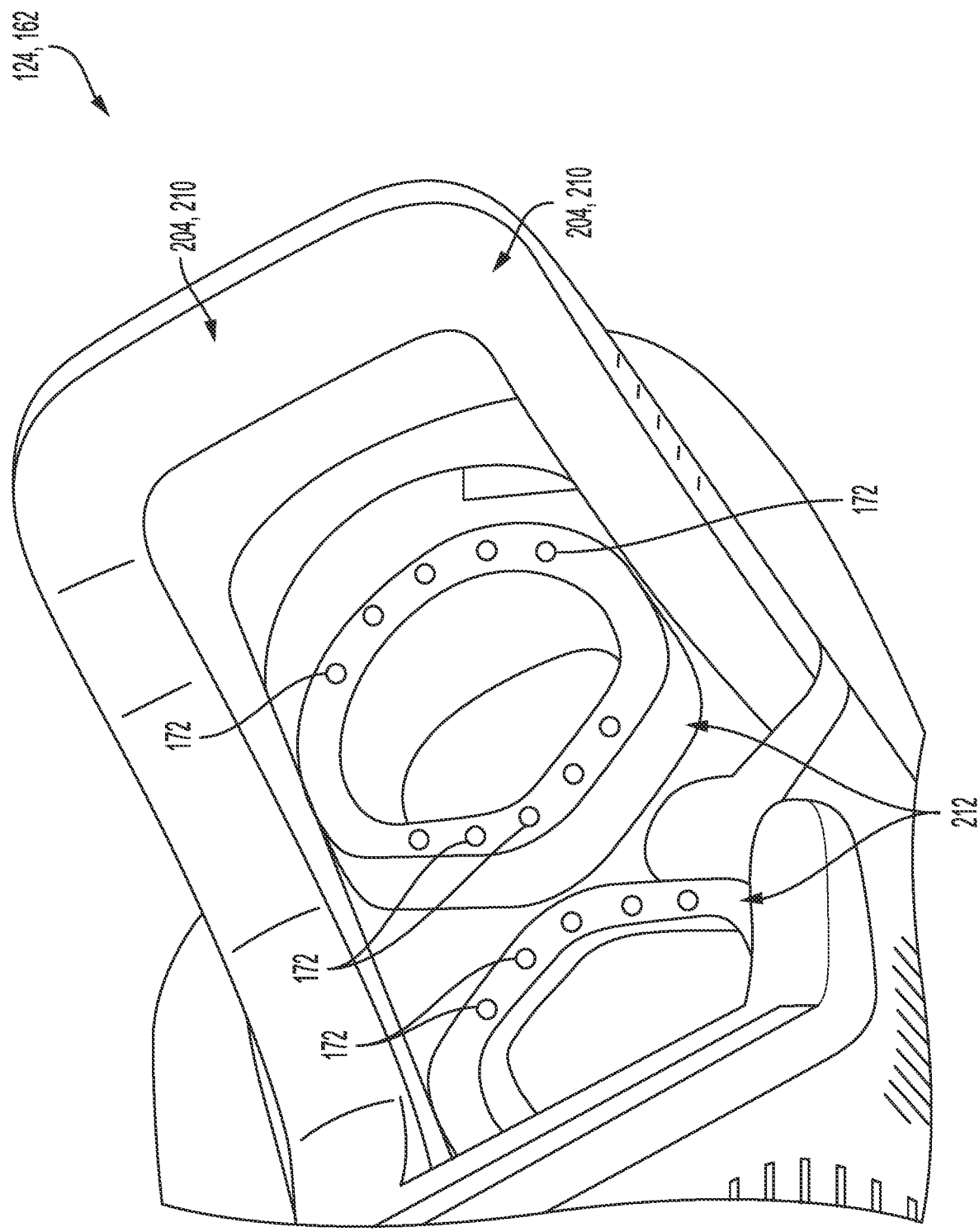
FIG. 13 is another rear isometric view of the medical headset of FIG. 10, illustrating a plurality of rearward-facing sensors and other sensors.
Figure 14:
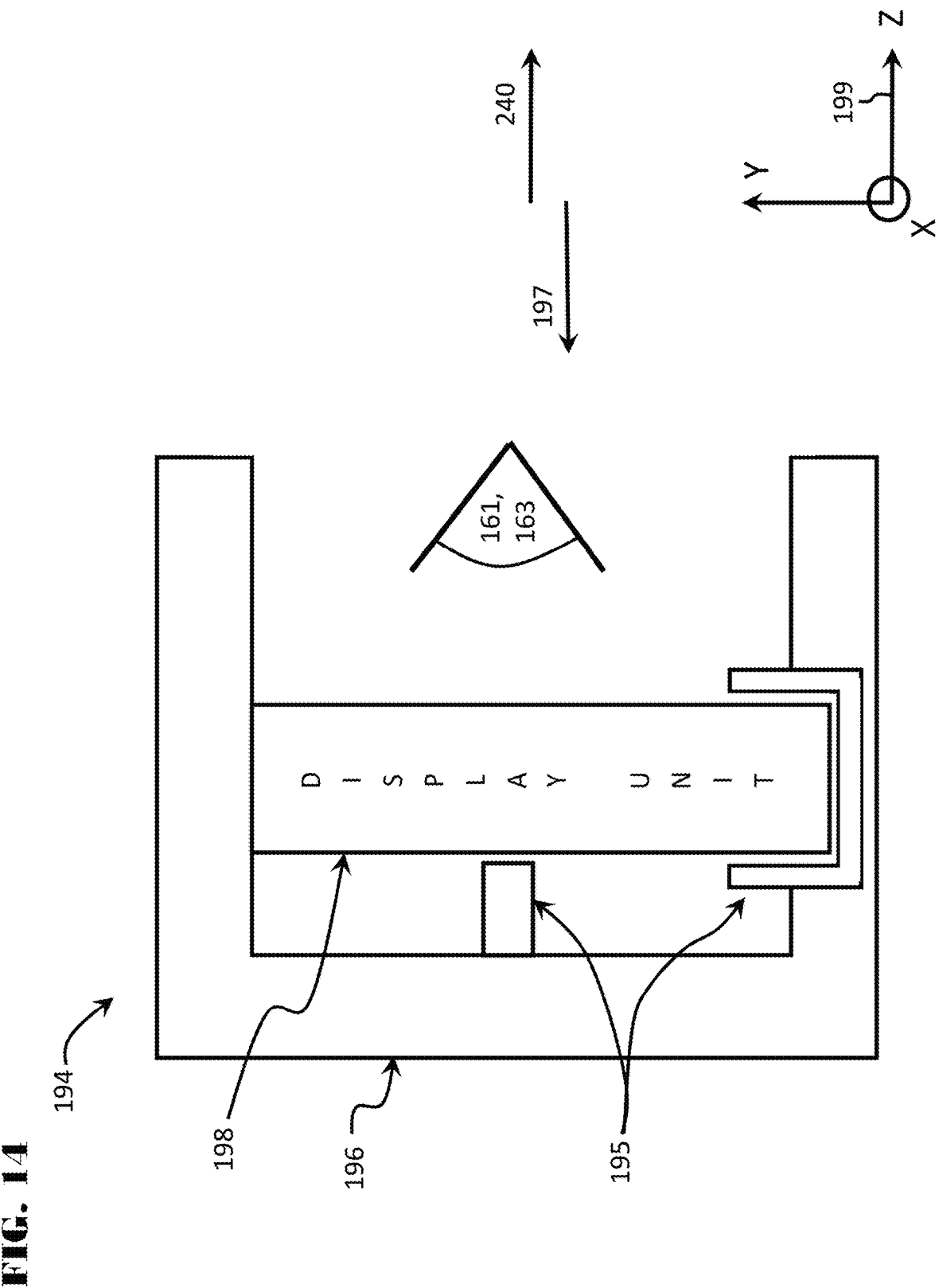
FIG. 14 is a schematic diagram illustrating an embodiment of the body of the medical headset of FIG. 10.
Figure 15:
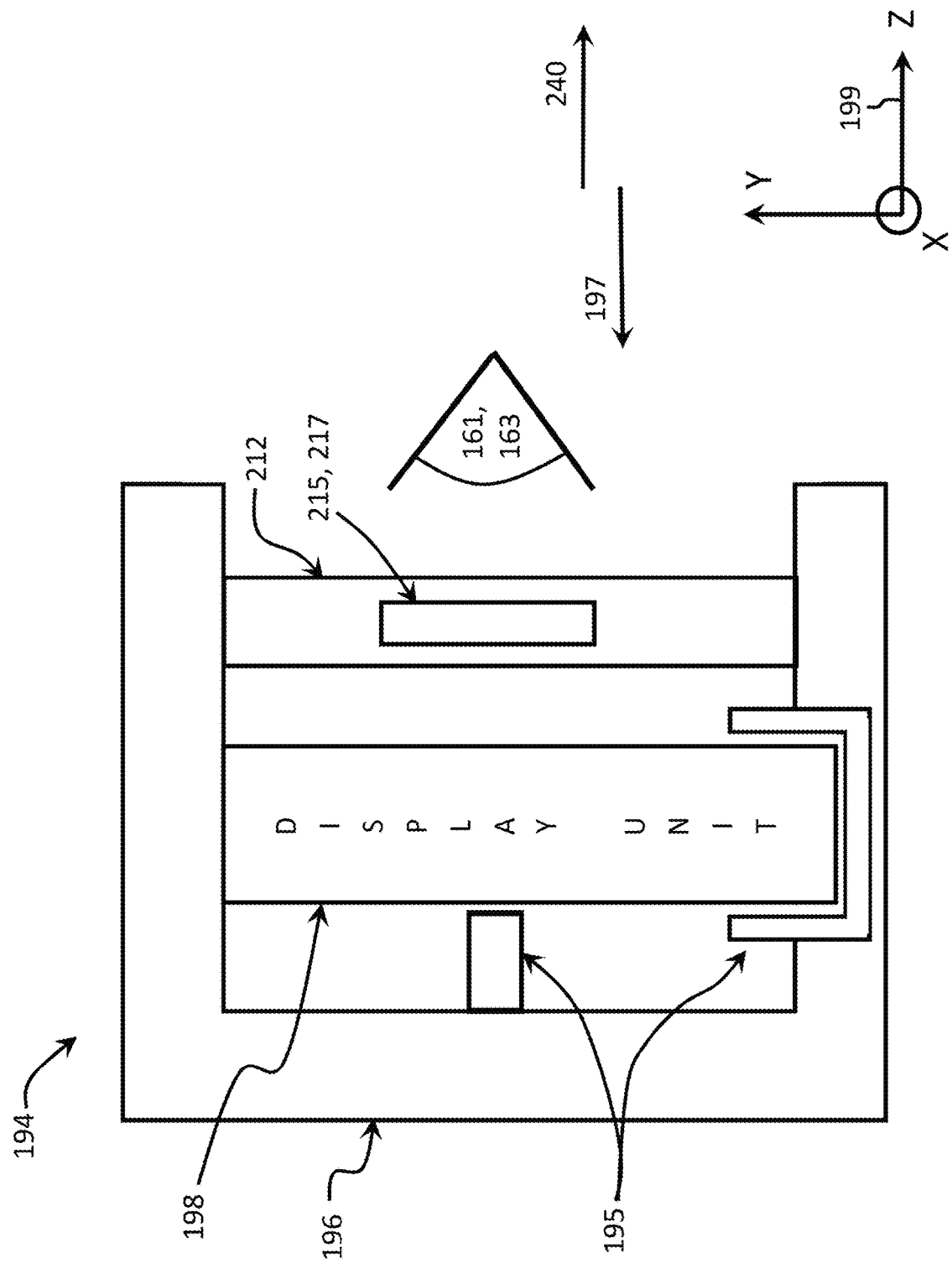
FIG. 15 is a schematic diagram illustrating another embodiment of the body of the medical headset of FIG. 10, illustrating an embodiment of the view splitter.
Figure 16:
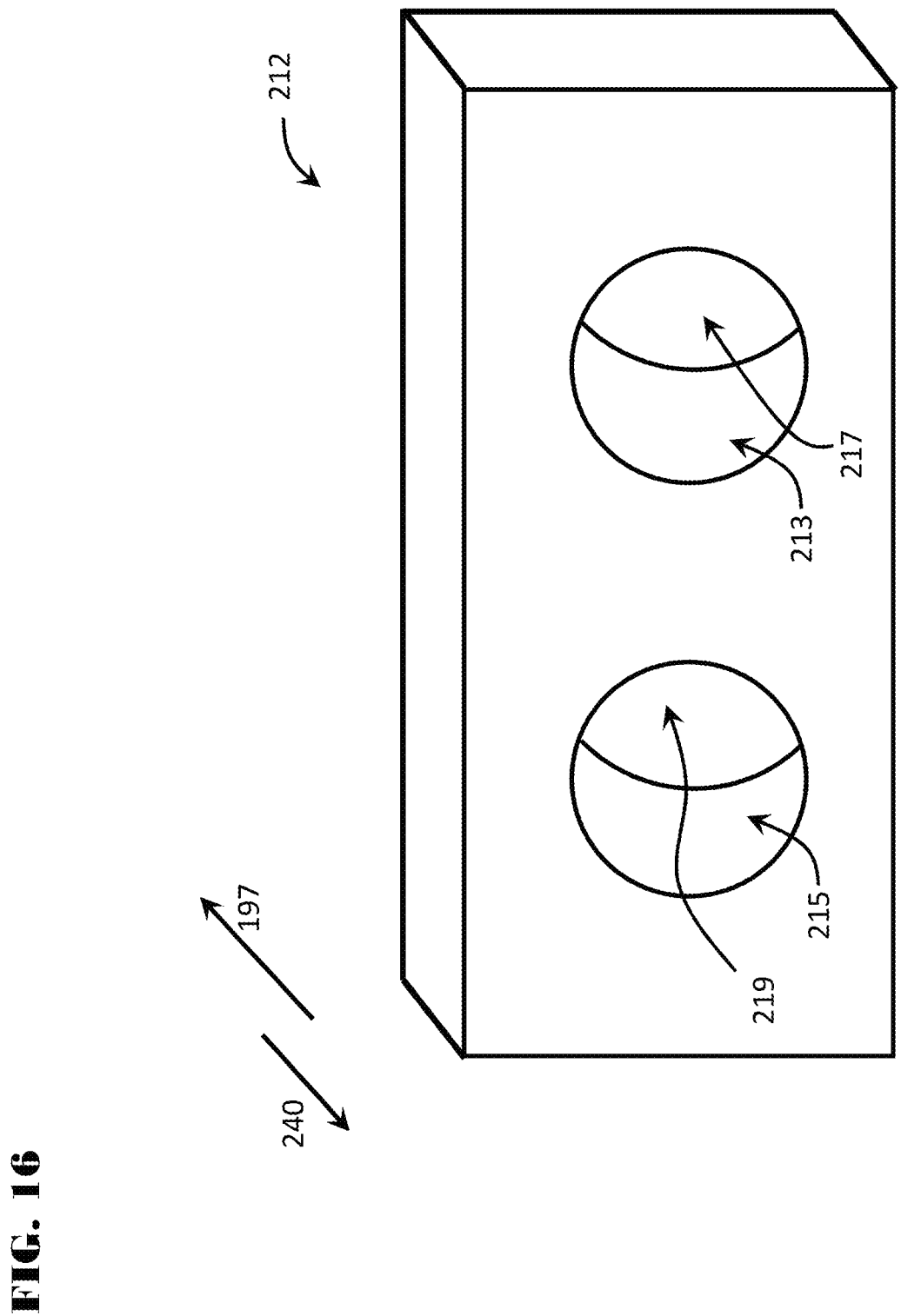
FIG. 16 is a rear isometric view of the view splitter of FIG. 15.

As shown in FIG. 10, each of the side arms 202 defines an interior channel or passageway (not shown) that receives a segment of the lower coupler 168. Such segment is anchored to an inside portion of such side arm 202. As shown in FIGS. 11-12, the face engager 204 has a face comfort enhancer 210 configured to engage with the face 206 of the subject 112. The face comfort enhancer 210 includes a pliable or elastic member or layer, such as a suitable padding, foam, rubber or polymeric material. Furthermore, when the medical headset 162 is properly secured to the head 160, different portions of the face comfort enhancer 210 compress and expand to conform to the unique geometry of the face 206 of the subject 112. As a result, the face comfort enhancer 210 functions as a light shield or light blocker, eliminating or minimizing the entrance of environmental light (e.g., sunlight and facility lighting) from reaching the eyes 161, 163.

In an embodiment shown in FIGS. 11-12 and 14-16, the face assembly 166 includes an eye isolator, vision splitter or view splitter 212. The view splitter 212 is configured to inhibit or prevent the right eye 161 from seeing the graphics intended for the left eye 163 while simultaneously inhibiting or preventing the left eye 163 from seeing the graphics intended for the right eye 161. Depending on the embodiment, the view splitter 212 can include a view divider, stereoscope, stereogram generator, stereo imager, eye isolator, vision splitter, binocular assembly or other device that enables or directs the viewing of a stereoscopic pair of separate images, depicting right-eye and left-eye views of the same scene. The view splitter 212 can cause the brain to perceive a three-dimensional (3D) visual effect 286, as described below.

In the illustrated embodiment, the view splitter 212 has a right tunnel or tube 213 and a left tunnel or tube 215 defining right and left channels or light passageways 217, 219, respectively. The display unit 198 generates light that radiates in the rearward direction 240 toward the subject 212. The view splitter 212 receives the light from the display unit 198 and directs part of the received light through the right tube 213 while directing another part of the received light through the left tube 215. The tubes 213, 215 are spaced apart and, therefore, split the received light that passes through the light passageways 217, 219. When the medical headset 162 is worn, the right light passageway 217 will align with the right eye 161, and the left light passageway 219 will align with the left eye 163. Accordingly, the view splitter 212, by separately controlling the light visible to the right and left eyes 161, 163, facilitates the generation of the 3D visual effect 286, as described below.

Figure 17:
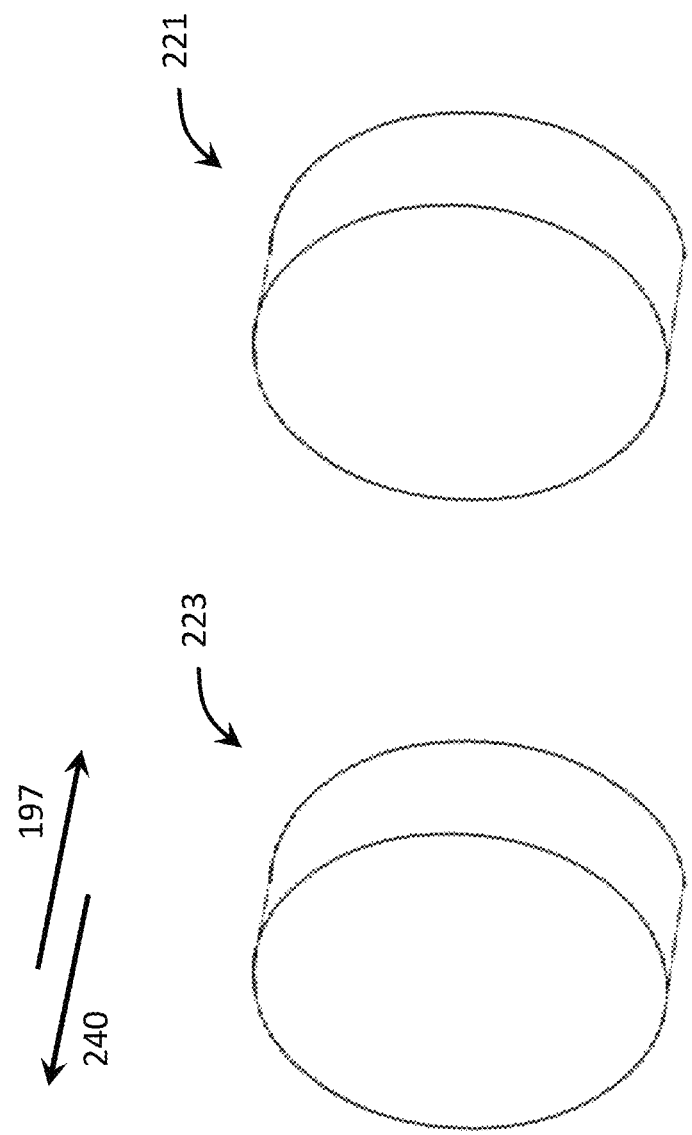
FIG. 17 is a rear isometric view of an embodiment of a plurality of lenses attachable to the view splitter of FIG. 15.

Referring to FIG. 17, in an embodiment, the view splitter 212 also has right and left lenses 221, 223. The right lens 221 is configured to mount or couple to the right tube 213 when placed over the right light passageway 217. The left lens 223 is configured to mount or couple to the left tube 215 when placed over the left light passageway 219. Depending on the embodiment, the lenses 221, 223 can be fully transparent, translucent or colorized.

Either of the lenses 221, 223 can be non-optically altering, serving solely as a see-through barrier or window. Alternatively, either of the lenses 221, 223 can have an optical alteration characteristic, including a refractive index or a designated curvature or shape associated with an optical alteration or vision corrective power. In an embodiment, the images visible through the right and left light passageways 217, 219 are shrunk due to a barrel distortion that causes a loss of field of view. To address this shrinkage effect, the lenses 221, 223 correct this loss by applying a pincushion distortion. It should be appreciated that the face assembly 166 can be fully operation for purposes of the medical assembly 110 with or without the lenses 221, 223. For example, the face assembly 166 can include the lenses 221, 223 for certain types of eye examinations. For other types of eye examinations, the face assembly 166 can exclude the lenses 221, 223.

Figure 18:
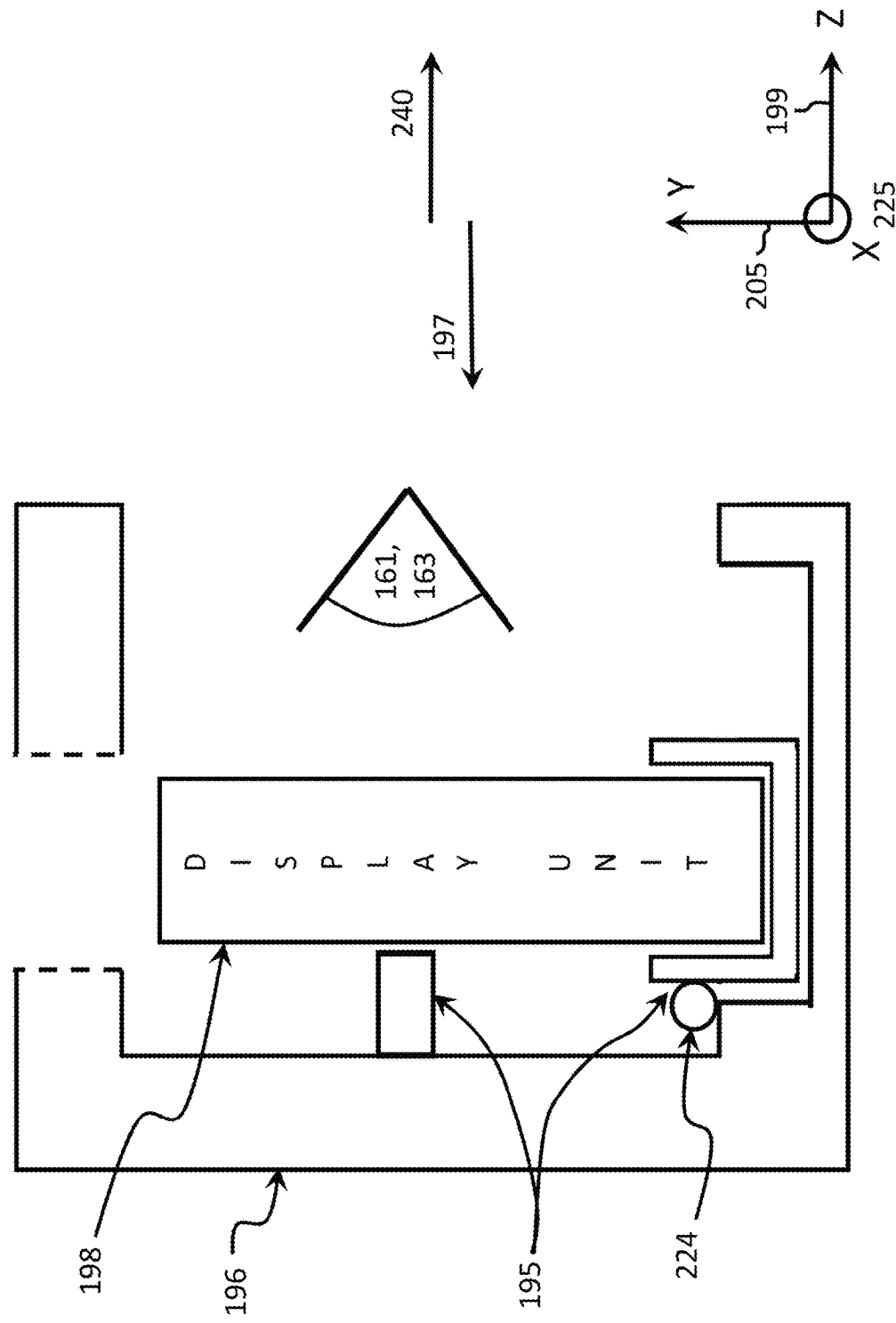
FIG. 18 is a schematic diagram illustrating an embodiment of the body of the medical headset of FIG. 10, illustrating the driver operable to reposition the display unit holder.

In an embodiment shown in FIG. 18, the display unit holder 195 is moveably coupled to the body 194. For example, the display unit holder 195 can mate with the body 194 through a slot and groove arrangement, enabling the display unit holder 195 to be slid relative to the body 194. In this embodiment, the face assembly 166 includes a driver 224 moveably coupled to the body 194. Depending on the embodiment, the driver 224 can include a knob or grasp configured to be rotated, pushed or pulled by the user, or the driver 224 can include a motor, solenoid or other electromechanical device operable to receive an adjustment input and apply a force to the display unit holder 195. In either such embodiment, the driver 224 is operable to move or reposition the display unit holder 195 relative to the body 194. Consequently, the driver 224 can change or vary, along the Z-axis 199, the distance of the display unit 198 relative to the subject's eyes 161, 163. Also, the driver 224 can change or vary, along the Y-axis 205, the vertical position of the display unit 198 relative to the subject's eyes 161, 163. In addition, the driver 224 can change or vary, along the X-axis 225, the horizontal position of the display unit 198 relative to the subject's eyes 161, 163. In an embodiment, the driver 224 adjusts the position of the display unit holder 195 along the X-axis 225, Y-axis 205, Z-axis 199 or a combination thereof to center the eyes 161, 163 relative to the display unit 198 or sensors 172 as part of a pre-examination setup or calibration process.

Figure 19:
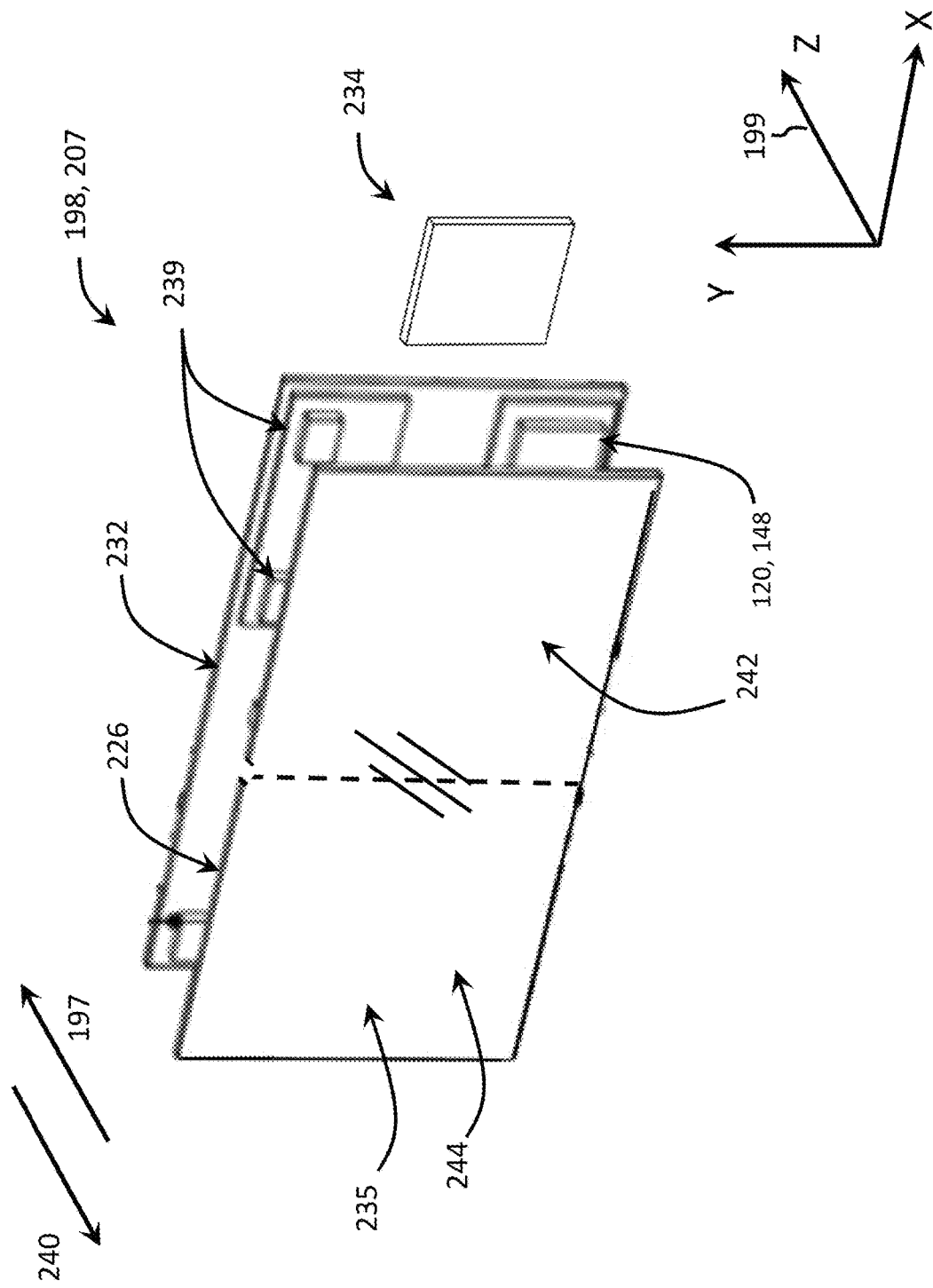
FIG. 19 is a rear isometric view of an embodiment of a display unit of the medical headset of FIG. 10, illustrating a single display device.
Figure 20:
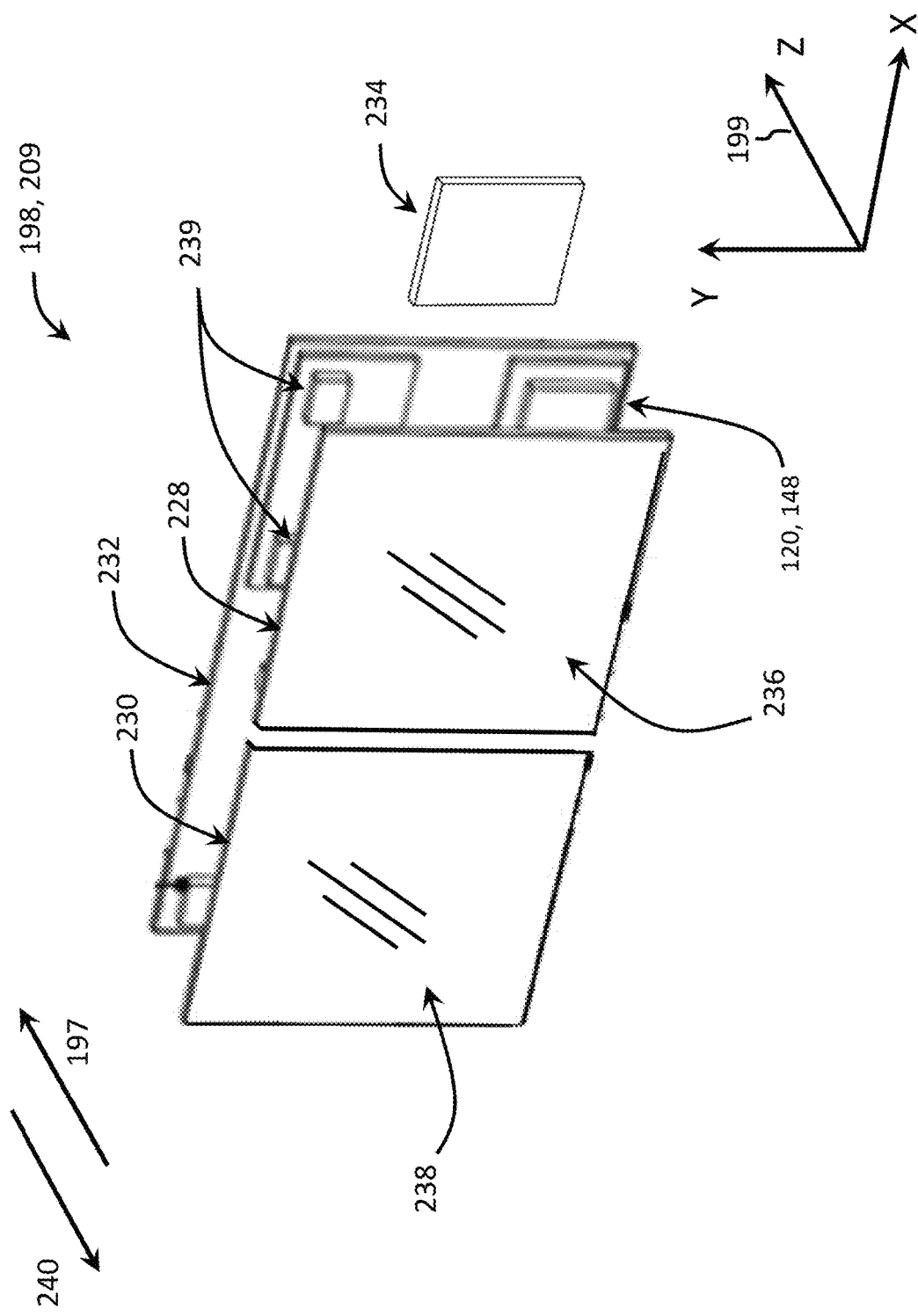
FIG. 20 is a rear isometric view of an embodiment of a display unit of the medical headset of FIG. 10, illustrating a plurality of display devices.

Referring to FIGS. 19-20, in an embodiment, the display unit 198 includes: (a) (i) a display unit 207 having a single display device 226, as shown in FIG. 19 or (ii) a display unit 209 having a plurality of cooperating right and left display devices 228, 230, as shown in FIG. 20; (b) one or more control boards, such as circuit board 232; and (c) a battery device 234 operatively coupled to the circuit board 232 and the cord assembly 173 shown in FIG. 10. In the embodiments shown, the single display device 226 has a single screen 235, the right display device 228 has a right screen 236, and the left display device 230 has a left screen 238. When the medical headset 162 is worn on the head 160, each of the screens 235, 236, 238 faces in a rearward direction 240 toward the subject 112.

In the embodiments shown, each of the display devices 226, 228, 230 can have any suitable image generator, including a liquid crystal display (LCD) device, an organic liquid crystal display (OLED) device, or any other suitable image generator. Depending on the embodiment, such LCD and OLED devices can include a layered structure having one or more polarizers, color filters, glass layers and liquid crystal layers. In another embodiment, neither of the display devices 226, 228, 230 has a screen. In such embodiment, each of the display devices 226, 228, 230 includes an image projector. The image projector is configured to beam or transmit photons onto the retinas of the eyes 161, 163 of the subject 112. In this case, each retina acts as a projection screen. Such image projector can provide shorter image response times than LCDs and OLEDs.

In the embodiment shown in FIG. 19, the single screen 235 of the display unit 207 has a right display area 242 and a left display area 244. The single screen 235 is configured and operable to independently generate images on the right and left display areas 242, 244. Accordingly, the right display area 242 is operable to generate an image A, for example, to the right eye 161 while the left display area 244 simultaneously generates an image B, for example, to the left eye 163. In the embodiment shown in FIG. 20, the right screen 236 is operable to generate an image A, for example, to the right eye 161 while the left screen 238 simultaneously generates an image B, for example, to the left eye 163. In the image projector embodiment described above, the image projectors are operable to transmit an image A, for example, onto the retina of the right eye 161 while simultaneously transmitting an image B, for example, onto the retina of the left eye 163. Accordingly, in either such embodiment, the display unit 198 produces a 3D visual effect 286, as described below.

Figure 21:
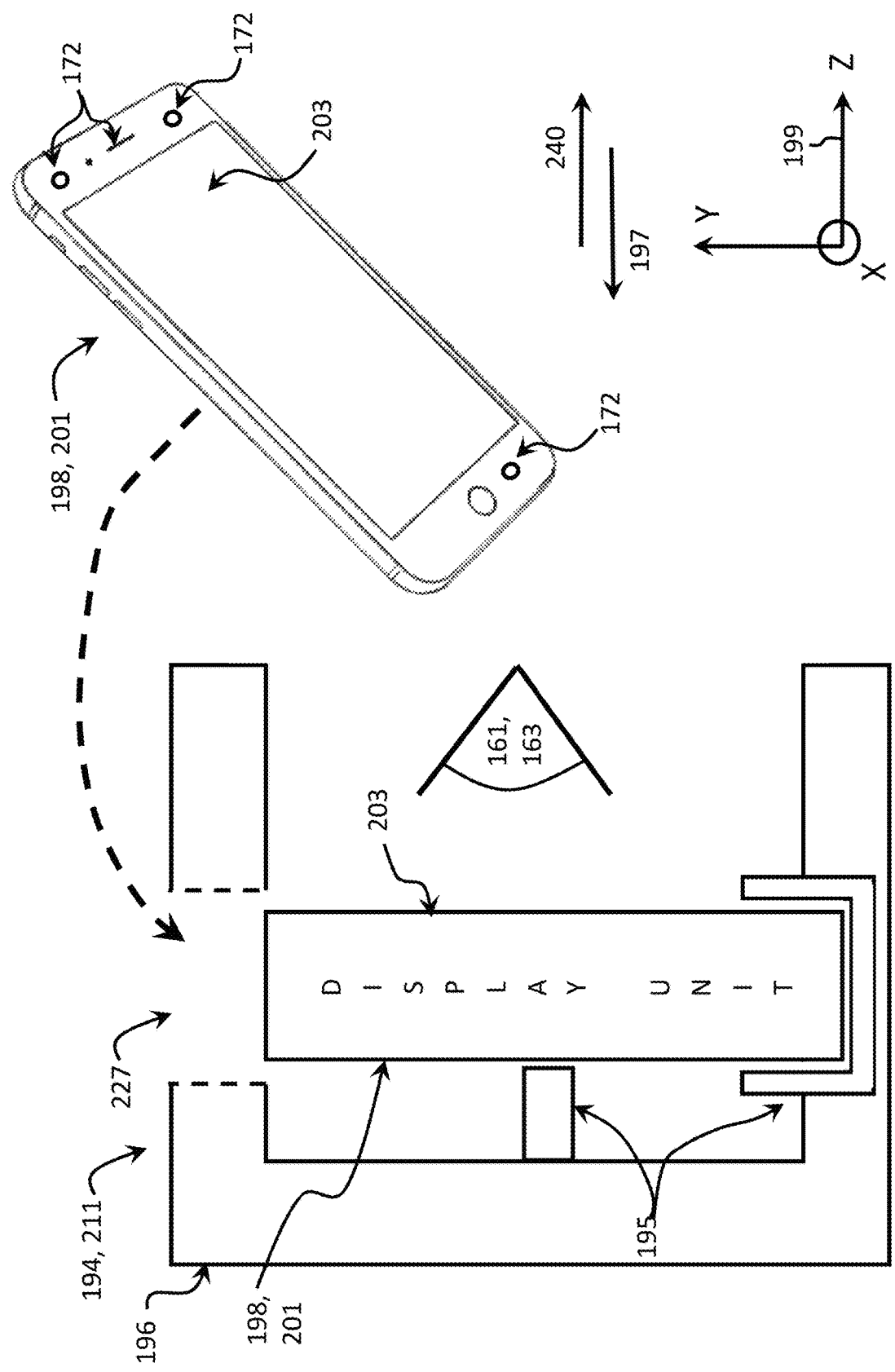
FIG. 21 is a schematic diagram illustrating an embodiment of the body of the medical headset of FIG. 10, illustrating a slot or opening configured to receive and removably hold a mobile computing device.

As shown in FIG. 21, in an embodiment, the display unit 198 includes a mobile computing device 201. The mobile computing device 201 has a mobile screen 203. The mobile computing device 201 can include a smartphone, mobile phone, tablet or other mobile device. For example, the mobile computing device 201 can include any commercially-available smartphone, such as the iPhone® smartphone made by Apple Inc. or the Galaxy® smartphone made by Samsung Electronics Co., Ltd. All of the specifications of such iPhone® and Galaxy® smartphones are hereby incorporated by reference into this disclosure. In this embodiment, the medical headset 162 has a body 211 that is configured to removably receive and hold either such mobile computing device 201. The body 211 defines a slot or opening 227 configured to receive the mobile computing device 201. As illustrated in FIG. 21, the user can insert the mobile computer device 201 through the opening 227 and into the display unit holder 195. In doing so, the user orients the mobile screen 203 to face in the rearward direction 240 toward the subject 112. Once inserted into the display unit holder 195, the display unit holder 195 grasps or otherwise secures the mobile computing device 201. Depending on the embodiment, the display unit holder 195 can include an adjustable securement device that, when rotated or moved, applies a securing force or biasing force to the mobile computing device 201. The mobile screen 203 functions the same as the single screen 235 described above.

In an embodiment, the mobile computing device 201 includes or is operatively coupled to the circuit board 232 or any portion thereof, including the sensors 172 and any of the processors 120, 148. It should be understood that the sensors 172 can be fully or partially housed in the mobile computing device 201 and can include a plurality of subject-facing sensors 172, including subject-facing cameras. Such sensors 172 include one or more eye movement sensors 246 and pupil resizing sensors 248, as described below. The mobile computing device 201 can be reversibly attached to the display unit holder 195 as described above. In addition, the mobile computing device 201 is configured to be operatively coupled to a plurality of sensors 172 that are located apart from the mobile computing device 201, including sensors 172 mounted to or embedded in the frame, housing or other structural components of the headset 124, 162 or 284. In this case, the mobile computing device 201 is operatively coupled to such sensors 172 through a wireless or wire-based connection.

In another embodiment not shown, the mobile computing device 201 is usable without being worn on the head 160 of the subject 112. In this embodiment, the subject 112 subject sits or stands facing the rear side of the mobile computing device 201, which is the side opposite of the mobile screen 203. Another user, such as a health care provider, faces the mobile screen 203. According to the medical system 114 and system data 125, the mobile computing device 201 assists such user in positioning the mobile computing device 201 so the face 206 of the subject 112 is at least substantially within the viewing field of the cameras of the computing device 201. Such user provides a set of visual stimuli to the subject 112 via movements of the user's finger or moving an object following the instructions displayed on the mobile screen 203. Such visual stimuli includes moving the finger vertically, horizontally, and a combination thereof. In this embodiment, the mobile computing device 201 is configured to be operatively coupled to the data processing apparatus 140, as shown in FIG. 6. This coupling can be wire-based or wireless.

In an embodiment, the face assembly 166 includes all of the parts, structure, elements and functionality as the Google Cardboard™ product made by Google LLC. Such product is configured to removably receive and hold a smartphone, which acts as a display unit 198. All of the specifications of such Google Cardboard™ product are hereby incorporated by reference into this disclosure.

In an embodiment, the circuit board 232 includes the processor 120. Such embodiment is compatible with the device-centric architecture 128 shown in FIG. 3, as described above. In another embodiment, the circuit board 232 includes the device processor 148. Such embodiment is compatible with the hybrid architecture 138 shown in FIG. 6, as described above.

Figure 22:
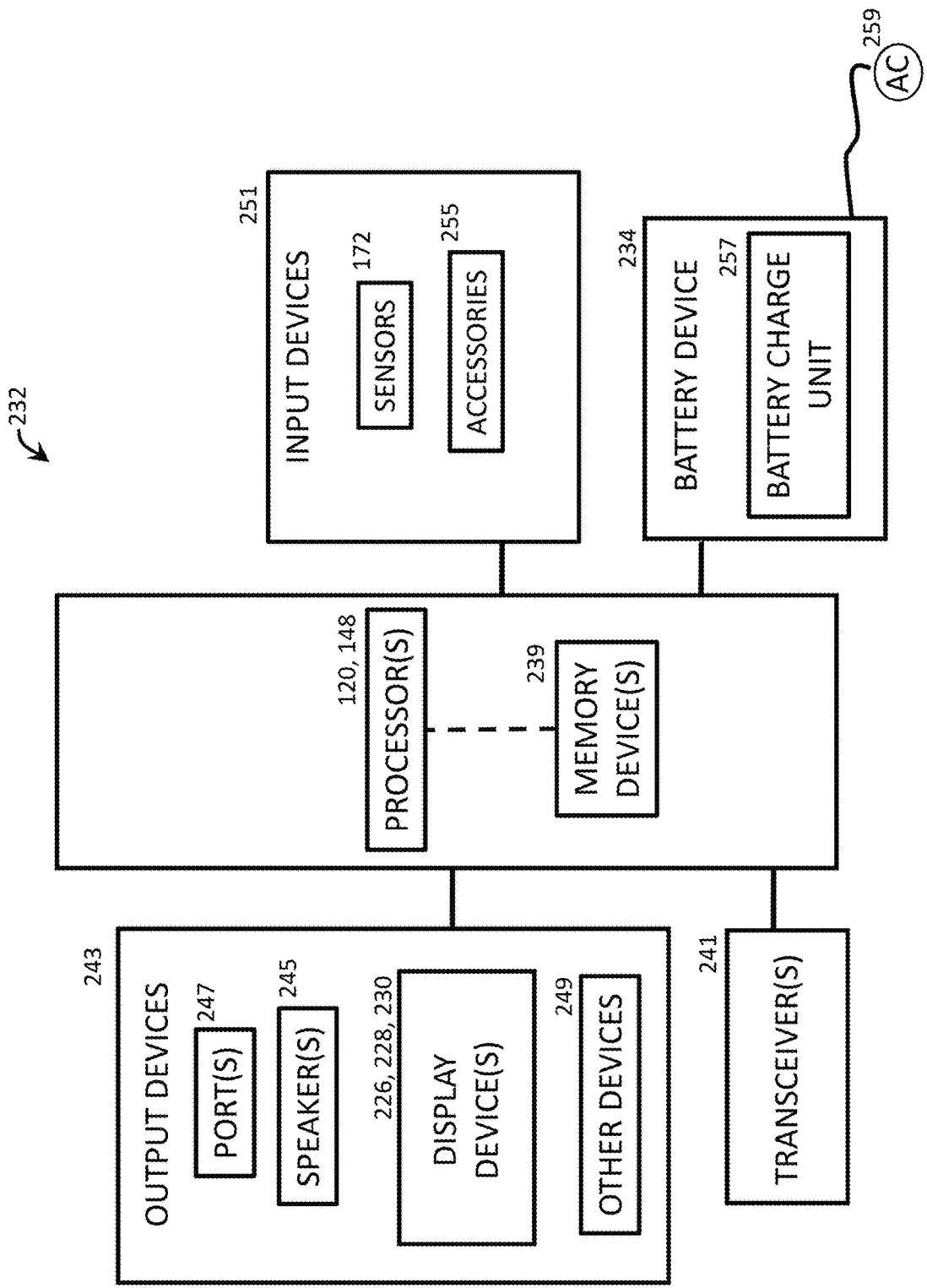
FIG. 22 is a schematic diagram illustrating an embodiment of the circuit board of the medical headset of FIG. 10.

Referring to FIGS. 19, 20 and 22, depending on the embodiment, the circuit board 232 includes, incorporates or is operatively coupled to: (a) the processor 120 or device processor 148; (b) a plurality of memory devices 239; (c) the battery device 234; (d) one or more antennas or transceivers 241 configured to wirelessly send and receive signals, including radio frequency (RF) and infrared (IR) signals; (e) a plurality of output devices 243, including the display devices 226, 228, 230, one or more speakers 245, one or more data ports 247, and other output devices 249, including a plurality of light source devices (e.g., flash lights) and light radiators; and (f) a plurality of input devices 251, including the sensors 172 and a plurality of accessories 255. In the embodiment shown, the battery device 234 includes one or more rechargeable battery cells and a battery charge unit 257 electrically coupled to the cord assembly 173 shown in FIG. 10. Users can periodically recharge the battery cells by connecting the cord assembly 173 to an alternating current (AC) power socket 259 or another source of electrical energy.

In an embodiment, the medical headset 162 operates at least one speaker 245 of the output devices 243 to generate audible commands, prompts or instructions. For example, the speaker 245 is operable, according to the medical system 114, to generate a voice command, such as "Follow the red dot."

In an embodiment, the medical headset 162 is operable with a plurality of the accessories 255. Depending on the embodiment, the accessories 255 can include handset controllers, handheld control devices, remote control devices, voice command devices, control pads, touchpads, keyboards, touchscreens and other suitable input devices. The accessories 255 can be operatively coupled to the circuit board 232 through a wire-based or a wireless connection, and the accessories 255 can be battery-powered or powered through electricity provided by an electrical power cord. Each accessory 255 is configured to receive an input or action from the user and transmit an input command or input signal to the medical headset 162. The medical headset 162 processes such input signals to control certain functions of the medical headset 162.

Figure 23:
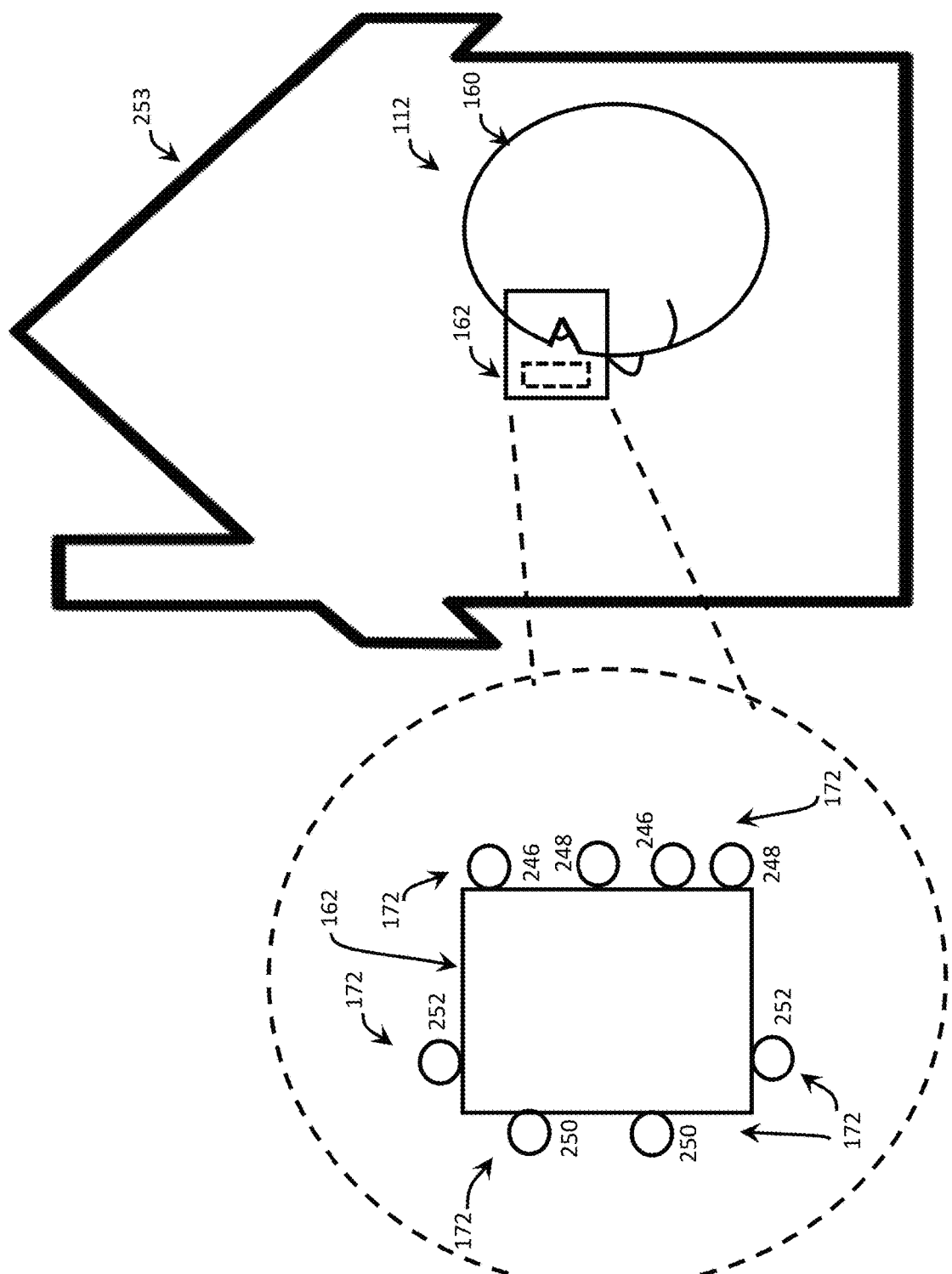
FIG. 23 is a schematic diagram illustrating a subject weaning the medical headset of FIG. 10 in an environment, illustrating a plurality of different types of sensors of the medical headset.
Figure 24:
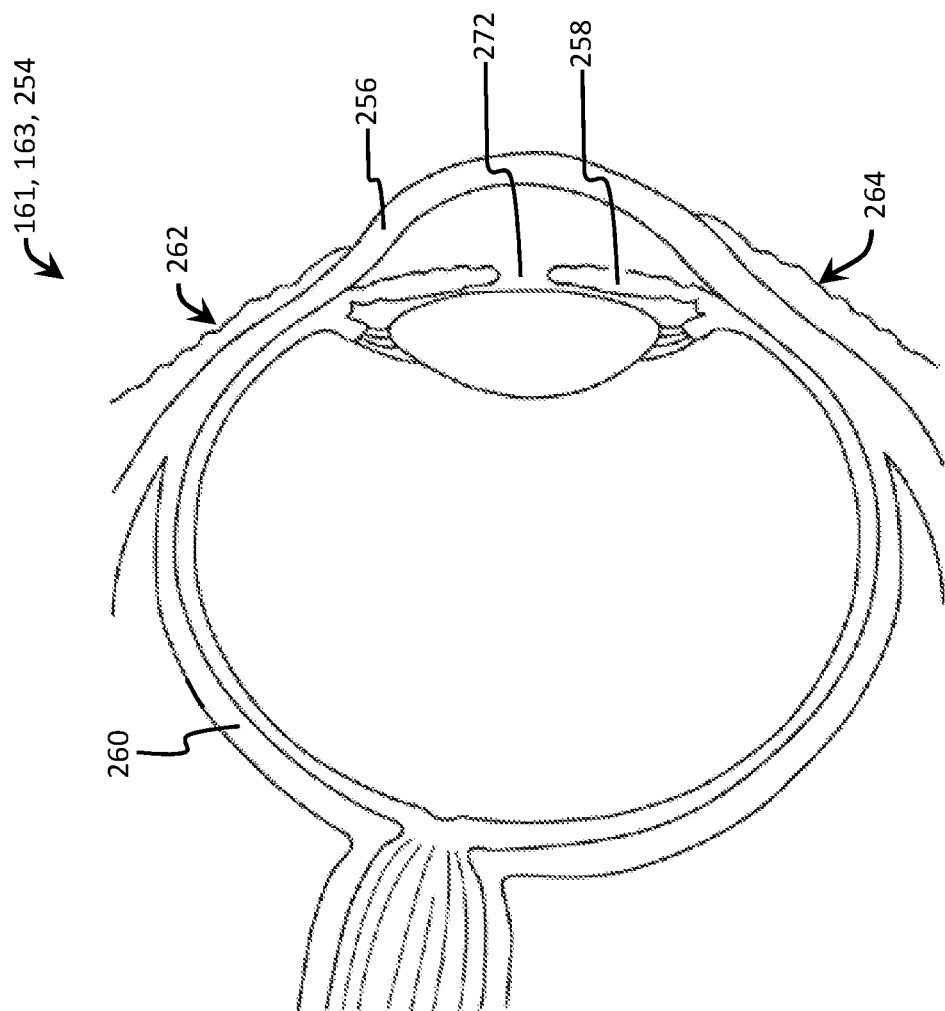
FIG. 24 is a side elevation view of an eye of a subject, illustrating anatomical parts of the eye.

Referring to FIGS. 23-25, the sensors 172 of the medical headset 162 include: (a) a plurality of eye movement sensors 246; (b) a plurality of pupil resizing sensors 248; (c) a plurality of head movement sensors 250; and (d) a plurality of supplemental sensors 252. It should be understood that the sensors 172 can be located on or in the medical headset 162 in any suitable position, arrangement or pattern. Referring to FIGS. 24-25, the eye movement sensors 246 are operable to detect or sense the movement of any part of the eye 254 relative to the head 160 or physical environment 253, including the following parts of the eye 254: the cornea 256, the iris 258, the sclera 260, the upper and lower eyelids 262, 264, the upper and lower eyelashes, 266, 268 and the eyebrow 270. It should be appreciated that the eye 254 represents the parts of each of the right and left eyes 161, 163 of the subject 112. The pupil resizing sensors 248 are operable to detect or sense the change in the diameter or size of the pupillary hole or pupil 272 relative to the head 160 or physical environment 253.

Figure 26:
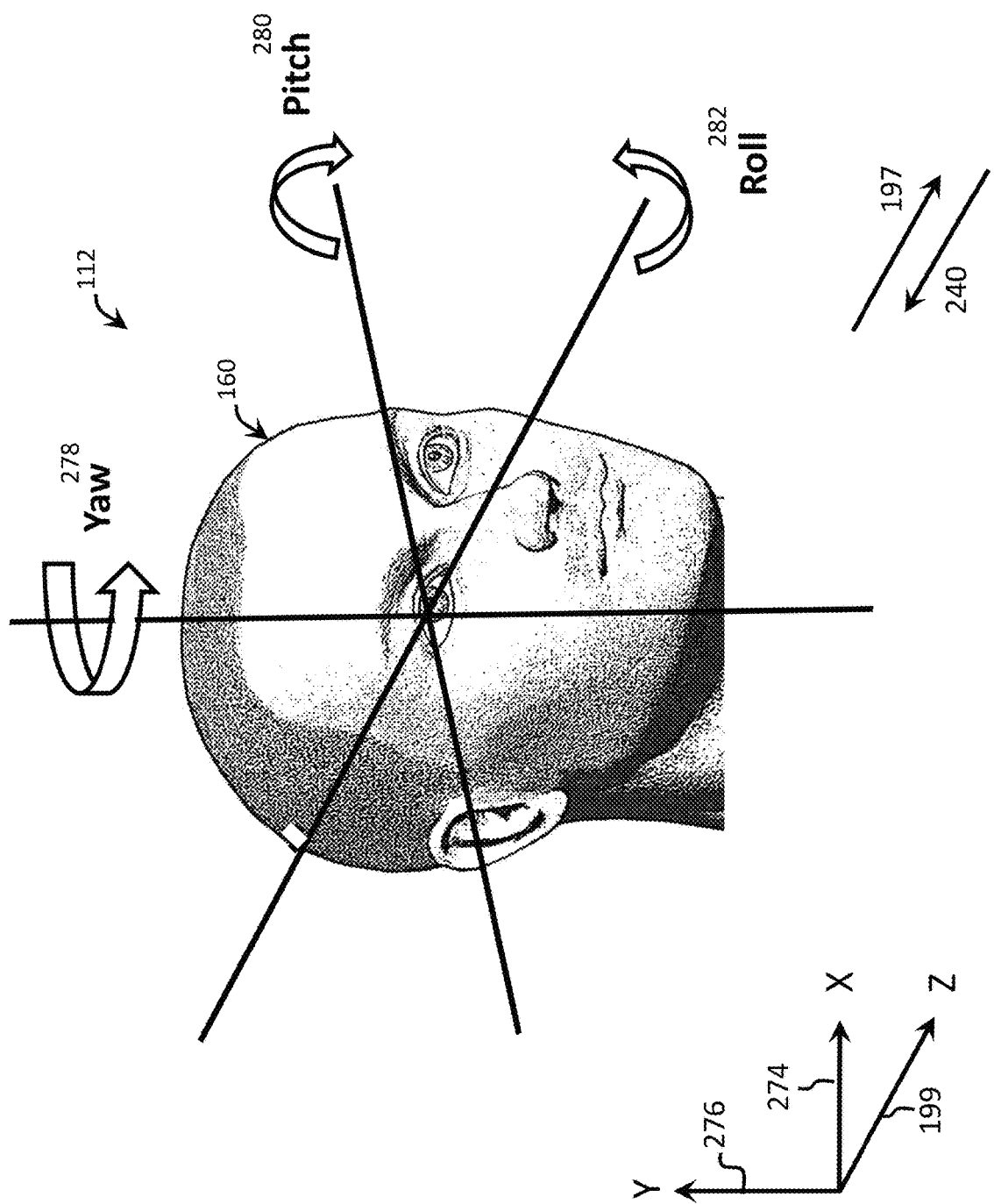
FIG. 26 is an isometric view of a subject, illustrating a plurality of rotational degrees of freedom of the subject.

Referring to FIGS. 24-26, the eye movement sensors 246 are operable to detect or sense the movement of the eye 254 (and parts thereof) relative to the head 160 or the physical environment 253, including the following degrees of freedom: (a) translational movements of the iris 258, eyelids 262, 264, eyelashes, 266, 268 and eyebrow 270 along an X-axis 274, Y-axis 276 or Z-axis 199; and (b) rotational movements of the eye 254 (including the cornea 256 and the sclera 260), including yaw rotation 278 (rotating from left to right or right to left), pitch rotation 280 (rotating downward or upward), pitch rotation 280 in a diagonal downward direction or diagonal upward direction, and variations of such rotational movements.

It should be understood that the physical environment 253 can include any indoor or outdoor environment, including any building, vehicle or outdoor site, such as a park or other plot of land. The head movement sensors 250 are operable to detect or sense the movement of the head 160 relative to the physical environment 253, including the following six degrees of freedom of the head 160 relative to the physical environment 253: translation along the X-axis 274, translation along the Z-axis 199, translation along the Y-axis 276, yaw rotation 278 (rotating the head 160 from left to right or right to left), pitch rotation 280 (rotating the head 160 to look downward or to look upward), and roll rotation 282 (tilting of the head 160 to the left or to the right).

Figure 27:
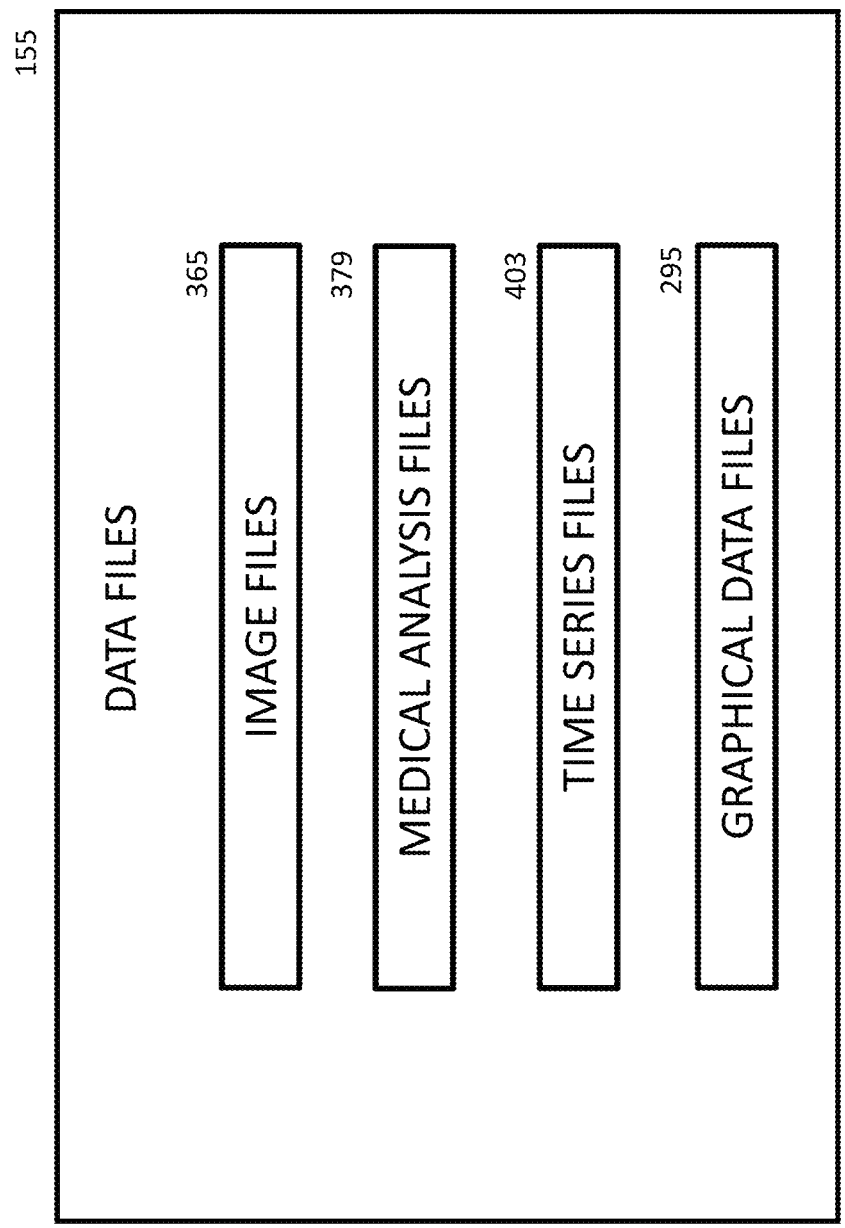
FIG. 27 is a schematic diagram illustrating an embodiment of the data files of the medical assembly of FIG. 1.
Figure 28:
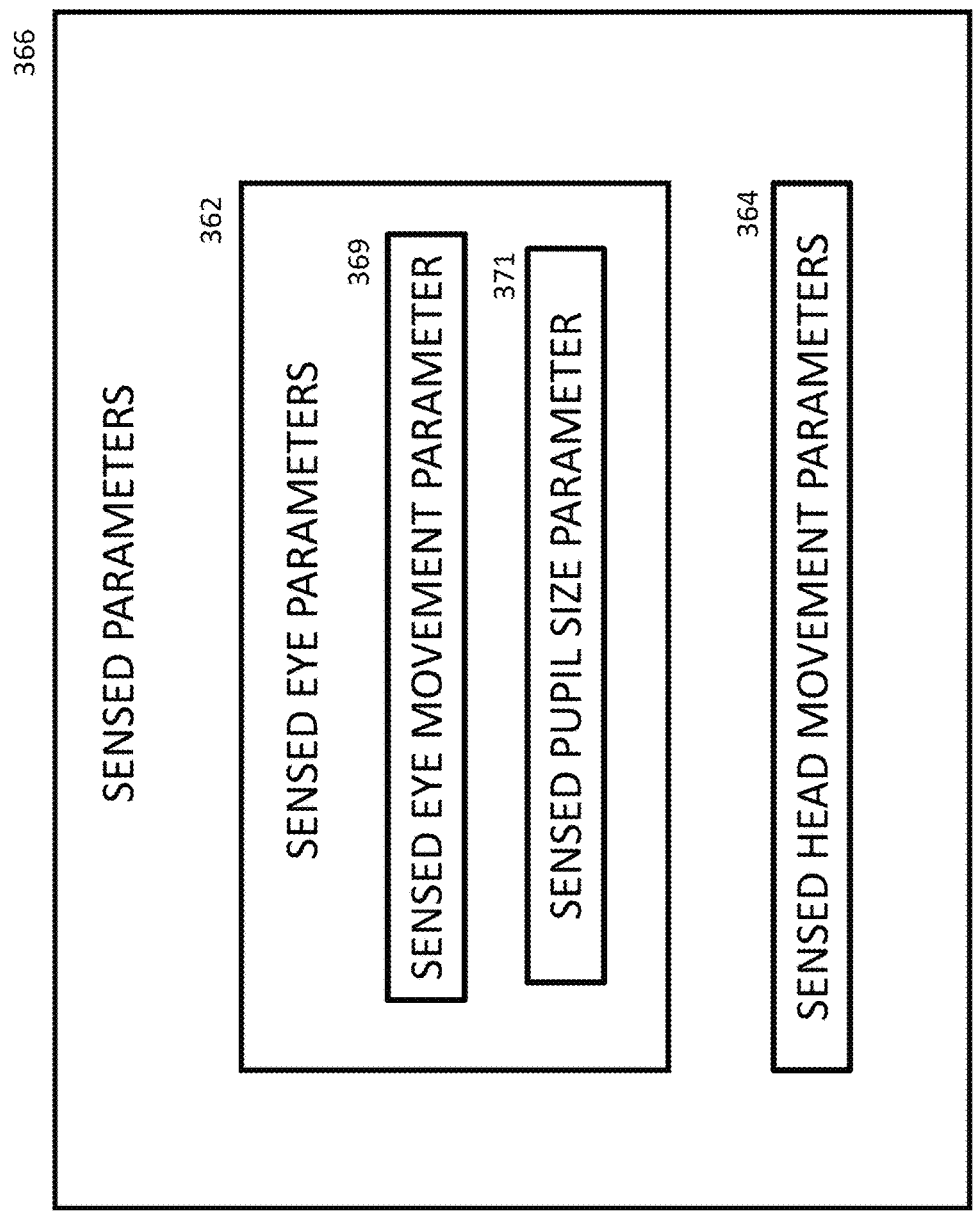
FIG. 28 is a schematic diagram illustrating an embodiment of different types of sensed parameters that can be received or generated by the medical assembly of FIG. 1.

Referring to FIG. 27, in an embodiment, the sensors 172 are configured and operable to capture a plurality of images of the eyes 161, 163, the face 206 and the head 160. Depending on the embodiment and adjustable settings, the sensors 172 can repetitively photograph a sequence of images of the eyes 161, 163, the face 206 or the head 160, or the sensors 172 can continuously record and generate a video of the action of the eyes 161, 163, the face 206 or the head 160. In either case, the sensors 172 generate a series of images, whether derived from photographs or video frames, and each of these images is stored in the form of an image file 365, as shown in FIG. 27. The medical assembly 110 applies or executes image processing algorithms and computer vision algorithms within the system logic 118. According to such algorithms, the medical assembly 110: (a) extracts the region of interest (ROI) of each eye 161, 163 and locates the pupil position in such ROI for each eye 161, 163, resulting in a plurality of sensed eye parameters 362, as shown in FIG. 28; and (b) analyzes each image of the head 160, resulting in a plural of sensed head movement parameters 364, as shown in FIG. 28.

Figure 29:
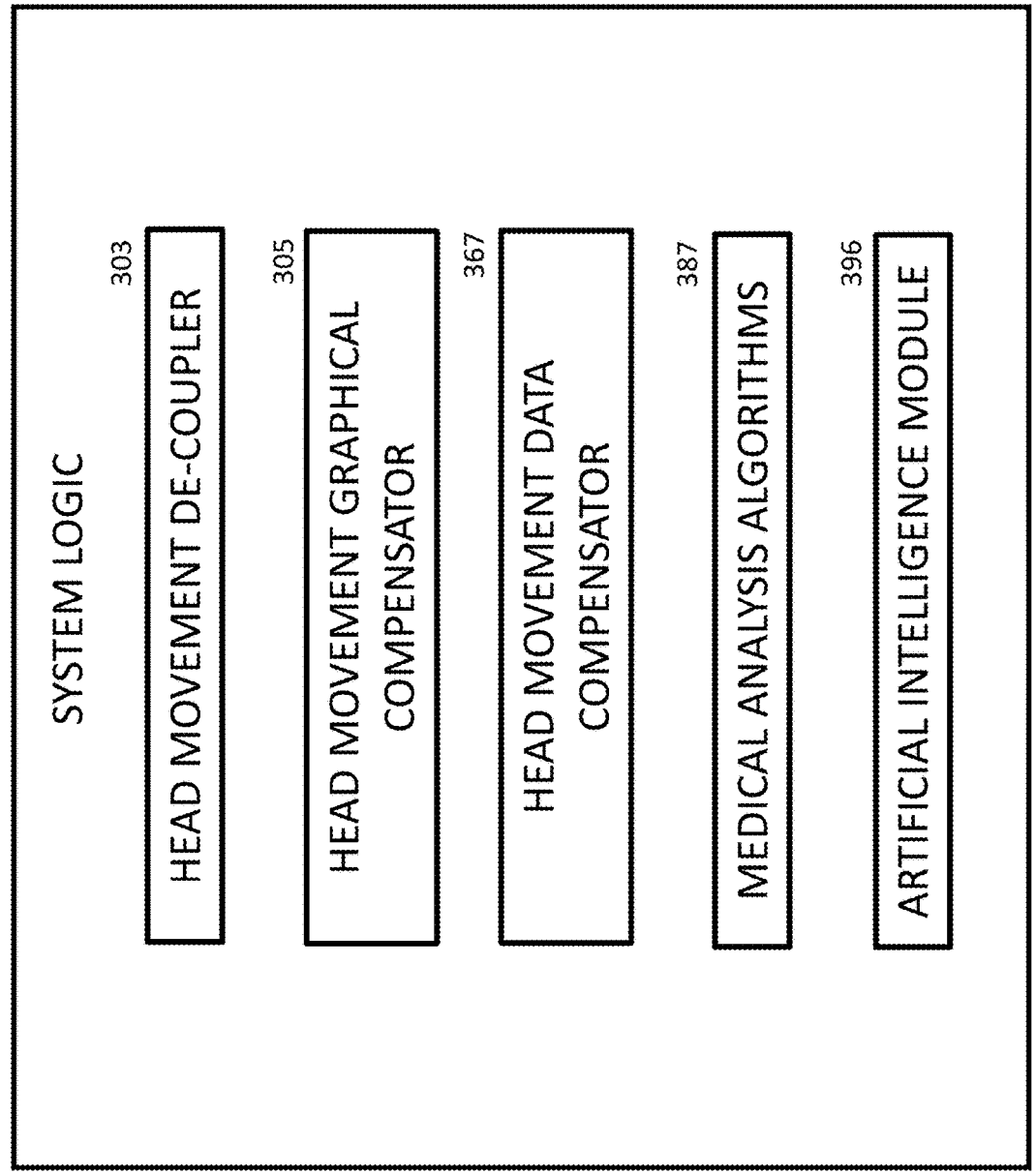
FIG. 29 is a schematic diagram illustrating an embodiment the system logic that is executable by the medical assembly of FIG. 1.
Figure 30:
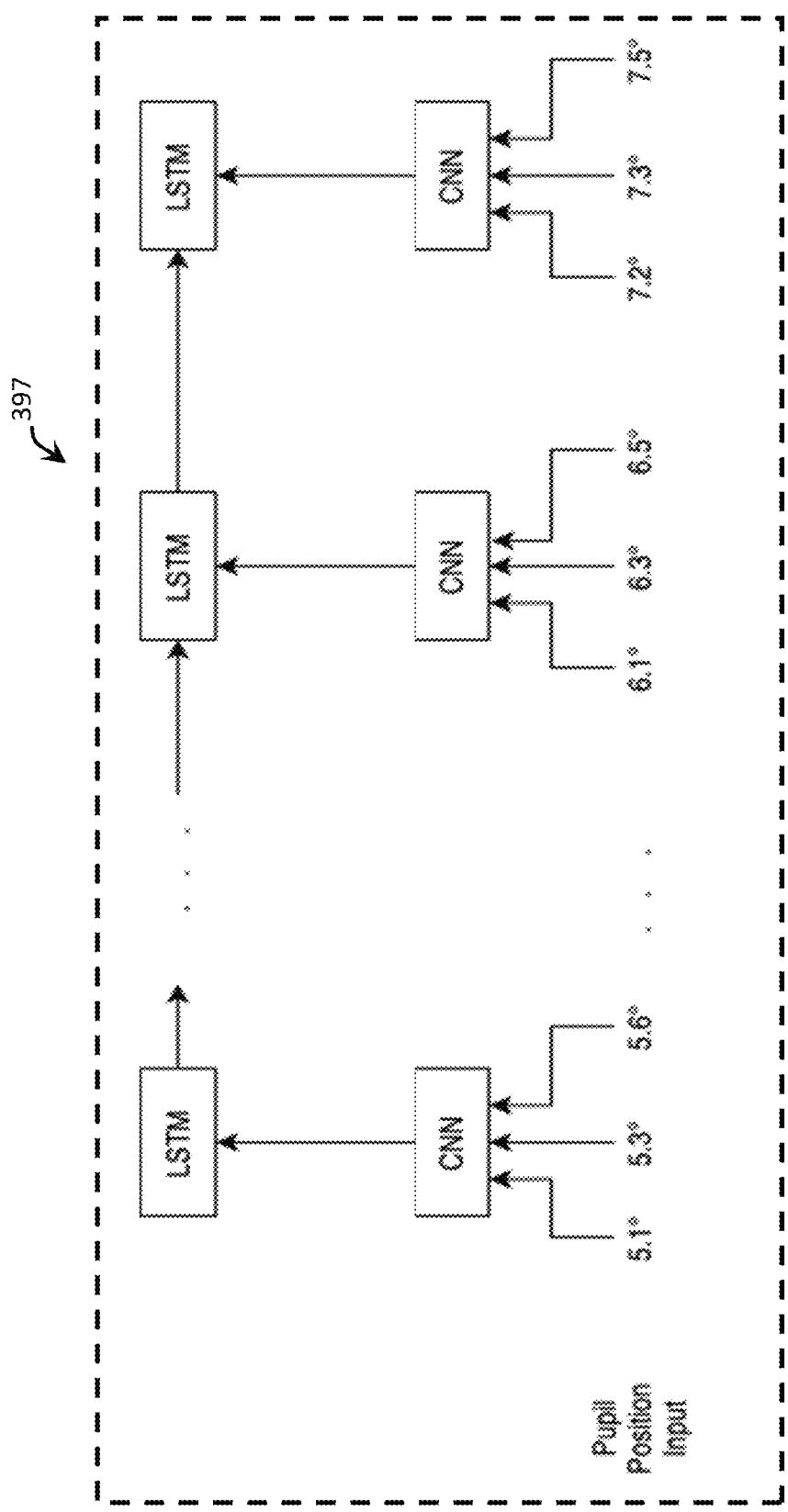
FIG. 30 is a schematic diagram illustrating an embodiment of a PnP algorithm that is executable by the medical assembly of FIG. 1.
Figure 31:
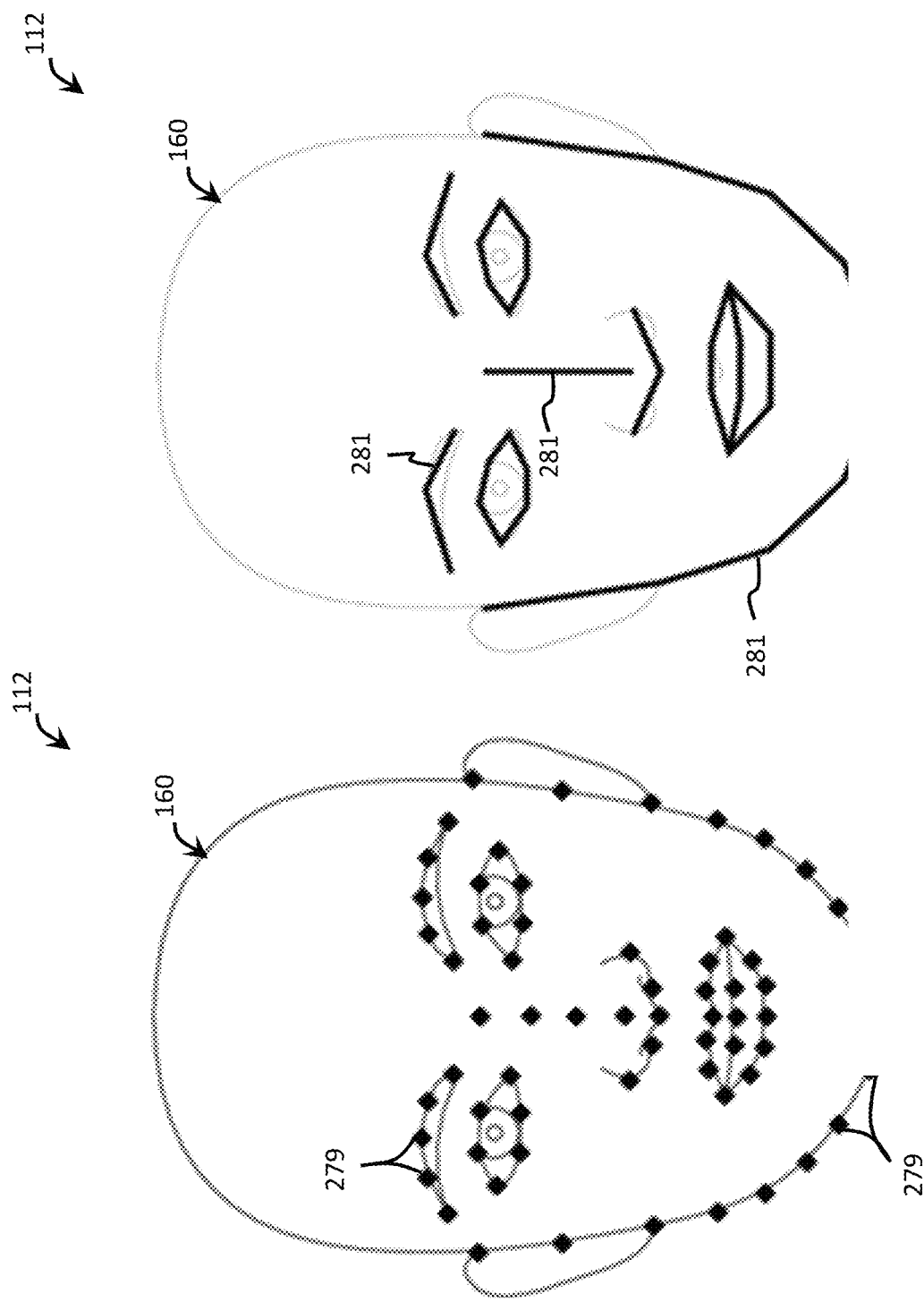
FIG. 31 is a front view of a subject's face marked with a plurality of face landmarks that are recognizable by the medical assembly of FIG. 1.

Referring to FIG. 29, in an embodiment, the system logic 118 includes an AI module 396, which the medical assembly 110 executes to calculate the head pose estimation for the head 160. As described below, the AI module 396 can include a machine learning algorithm trained based on a head pose dataset derived from actual medical outcomes, or the AI module 396 can include a perspective n point (PnP) algorithm 397 for sensing the variable positions of the eyes 161, 163. As illustrated in FIGS. 30-31, the PnP algorithm 397 directs the medical assembly 110 to detect a plurality of predetermined or designated face landmarks 279 (indicated in FIG. 31 as diamonds) and designated face landmarks 281 indicated in FIG. 31 as lines. Then, the PnP algorithm 397 directs the medical assembly 110 to use the face landmarks 279, 281 to calculate or determine an estimate of the positions of the eyes 161, 163 relative to the head 160. In an embodiment, the face landmarks 279, 281 used to calculate the head pose estimation include the corners of the eyes, the tip of the nose, the two corners of the mouth, and the chin. The medical assembly 110 is operable to calculate the head orientation (e.g., the angular positions described above) and the velocity of head movement relative to the physical environment 253 depending on the head pose estimation of each recorded image of the head 160.

In an embodiment, for testing pupil size, the medical headset 162 is operable to shine a light into the subject's eyes for a period of time. During this period, the sensors 172 capture a plurality of images of the pupil to test for reaction to brightness change. As described above, the medical assembly 110 applies or executes image processing algorithms and computer vision algorithms within the system logic 118. According to such algorithms, the medical assembly 110 locates the pupil position and calculates the pupil size or diameter, resulting in sensed eye parameters 362.

The supplemental sensors 252, shown in FIG. 23, are operable to detect or sense activity, actions or changes undertaken by, experienced by or caused by the subject 112, any user or the physical environment 253. In an embodiment, the supplemental sensors 252 are operable to detect or sense the following: sounds and voice commands produced by the subject 112 or other users, ear movement relative to the head 160 or physical environment 253, the variable temperature of the subject 112, variable air or gas composition, and other conditions and events.

It should be understood that, depending on the circumstance, the medical assembly 110 can receive sensed parameters 366 or, alternatively, the medical assembly 110 can generate sensed parameters 366. In some events, the medical assembly 110 receives sensed parameters 366 (e.g., measurements) associated with sensor signals generated by the sensors 172. In other events, the medical assembly 110 receives image files 365 and generates sensed parameters 366 (e.g., measurements) depending on a processing of the image files 365 or an analysis of the images stored in the image files 365. In each scenario, however, the medical assembly 110 ultimately processes the sensed parameters 366 to generate examination outputs 127.

Depending on the embodiment, the sensors 172 include thermal sensors, heat sensors, photonic sensors, infrared sensors, motion sensors, light sensors, video trackers, camera trackers, laser-based trackers, scanners, thermometers, accelerometers, gyroscopes, digital compasses, magnometers, cameras, camera lenses, photographic devices, video recorders, image capturing devices, sound sensors, microphones, haptic sensors, biometric imaging devices, facial recognition devices, and other electronic or electromechanical devices operable to sense, track, monitor, record or detect movement of or changes in the eye 254, any part thereof, the face 206, any part thereof (including lips), or the head 160, any part thereof (including ears), including eye tracking sensors, pupillary sensors, eye lid sensors, lip sensors and ear sensors.

Figure 32:
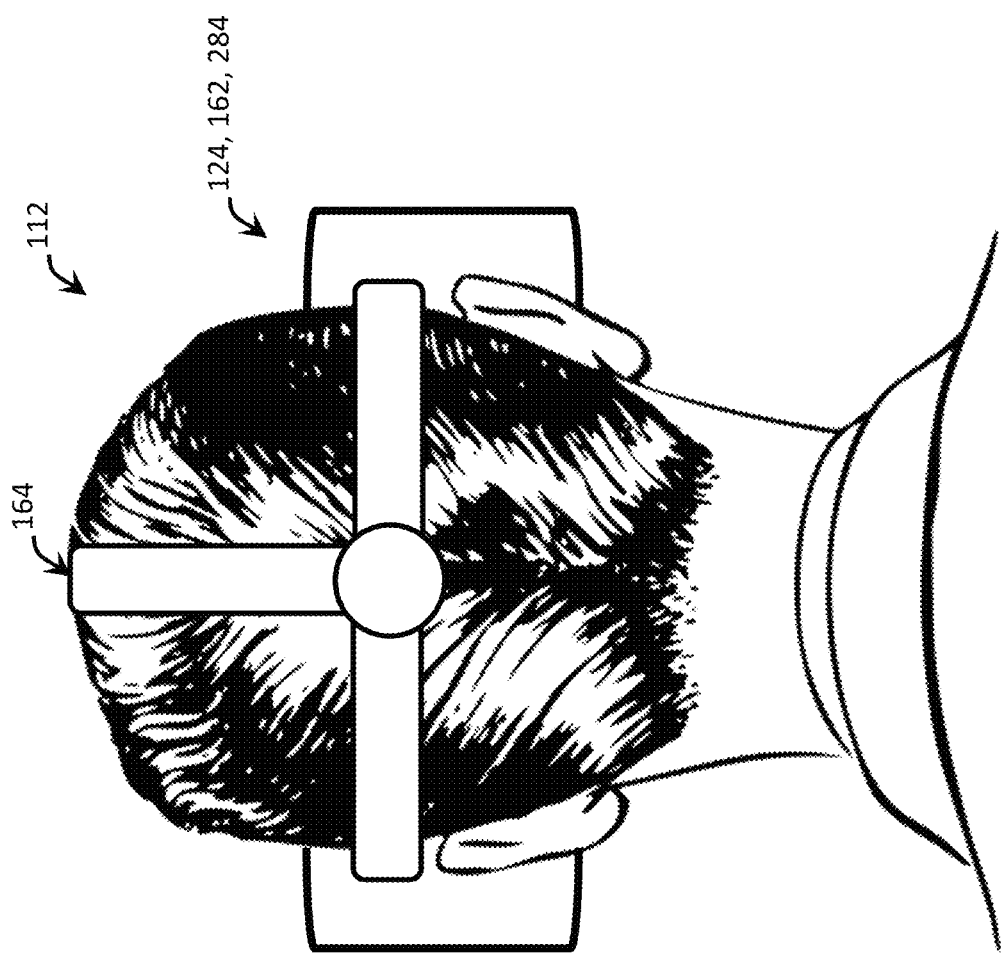
FIG. 32 is a rear view of an embodiment of a 3D medical headset, which is an embodiment of the medical headset of FIG. 10, which, in turn, is an embodiment of the wearable device of the medical assembly of FIG. 1.
Figure 33:
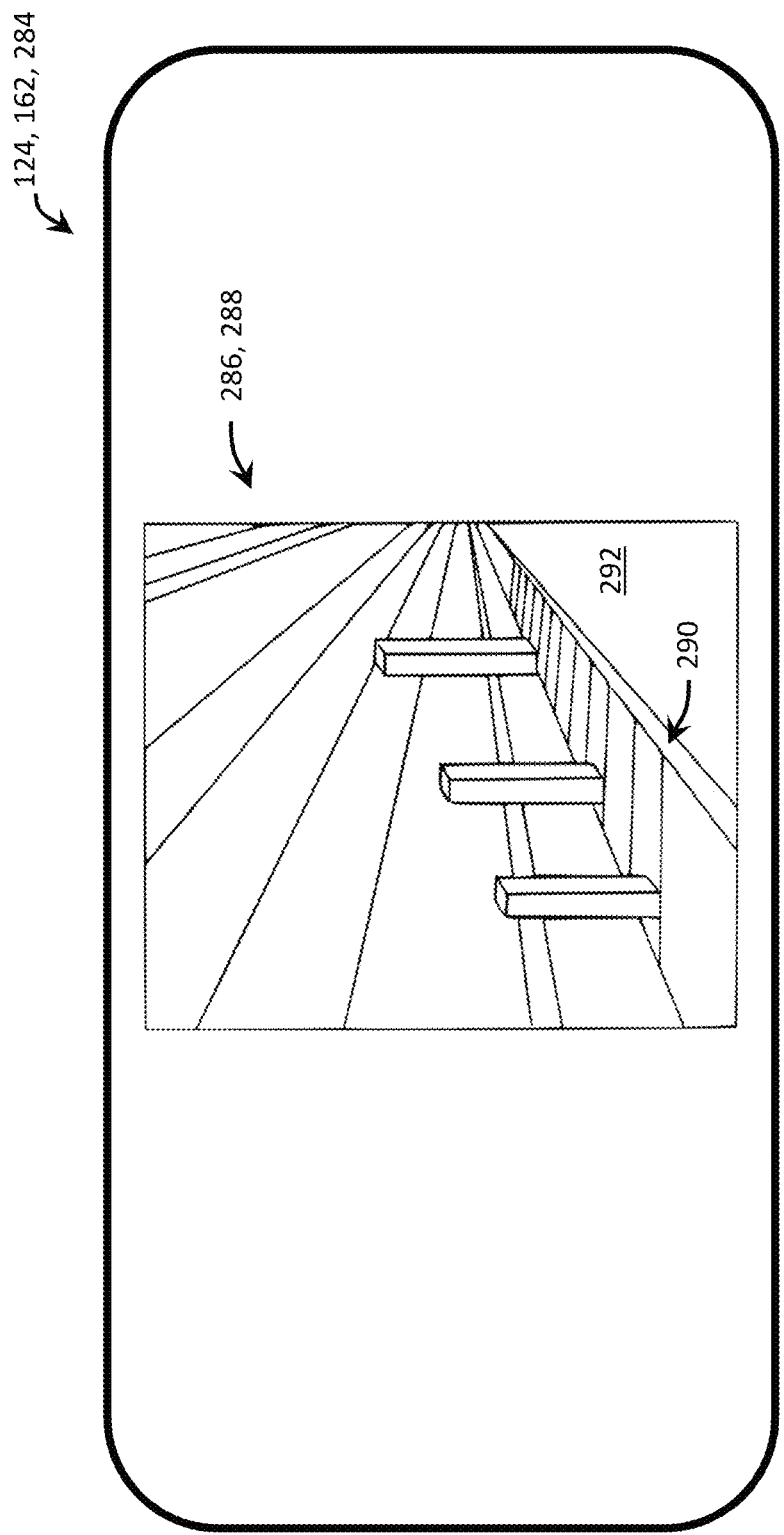
FIG. 33 is a rear view of the 3D medical headset of FIG. 32, illustrating an example of a 3D visual effect generated by the 3D medical headset.

Referring to FIGS. 32-33, in an embodiment, the medical headset 162 includes a 3D medical headset 284 operable to generate relatively high resolution graphics. The 3D medical headset 284 incorporates Virtual Reality hardware and software (VR), Augmented Reality hardware and software (AR), Substitutional Reality hardware and software (SR), Mixed Reality hardware and software (MR), XR hardware and software (XR), or any suitable combination of VR, AR, SR, MR and XR. It should be appreciated that XR is a term commonly used to describe any VR, AR, SR or MR system. The 3D medical headset 284 is configured and operable to generate a 3D visual effect 286 that provides a 3D viewing experience to users. The 3D visual effect 286 simulates, depicts or otherwise displays a 3D computerized environment 288. Depending on the embodiment, the 3D computerized environment 288 can include: (a) a graphical environment that is entirely computer-generated; (b) the physical environment 253; or (c) a combination of such graphical environment and the physical environment 253. Also, depending on the embodiment, the 3D visual effect 286 can provide a user with an immersive viewing experience, creating the impression the user is located in a different physical place even though the user knows the user is wearing a headset. In this regard, the 3D medical headset 284 can include an immersive medical headset.

In an embodiment, the 3D visual effect 286 causes the brain to perceive an experience as if the subject 112 were physically interacting inside the 3D computerized environment 288. The 3D medical headset 284 is configured to generate a three-dimensional (3D) dynamic graphic 290 that is moveable or changeable relative to a 3D static background graphic 292. In an embodiment, the 3D medical headset 284 is operable in a plurality of modes, including a 3D mode and a two-dimensional (2D) mode. In the 3D mode, the 3D medical headset 284 is operable to generate 3D graphics as described above. In the 2D mode, the 3D medical headset 284 is operable to generate 2D graphics as an alternative to 3D graphics. For example, depending on the settings and particular eye test, as described below, a user can use the 3D medical headset 284 to generate 3D graphics, 2D graphics or a combination of 3D and 2D graphics. Whether generating 3D or 2D graphics, the 3D medical headset 284 is configured to displays changes in the graphics in response to physical movement of the subject's eyes, head, face or body. For example, the 3D medical headset 284 is operable to create a 3D visual effect 286 giving the subject or another wearer the impression that he or she is moving or walking about in a virtual environment or in the physical environment 253.

The 3D medical headset 284 is operable to generate graphics in the form of static images (i.e., still images) or videos (i.e., motion picture). Each video can include a sequence of static images or video frames. The 3D medical headset 284 is operable to incrementally display the video frames, quickly replacing one video frame with the next video frame, creating an experience of watching motion. For example, an eye test may prompt the subject 112 follow a red dot as the red dot moves from the left side of the screen to the right side of the screen. The 3D medical headset 284 may then play or execute a graphical data file that includes a video of the red dot's movement. The video may include one hundred static images showing the red dot at different positions ranging from the first static image of the red dot at the far left position to the last static image of the red dot at the far right position.

The 3D medical headset 284 having AR is operable to overlay digitally-created graphics into the physical environment 253. The subject 112 is able to see the physical environment 253 either directly or through displays that reflect the physical environment 253 captured through digital cameras.

The 3D medical headset 284 having MR is operable to overlay digitally-created graphics to the physical environment 253. However, in mixed reality, the digitally-created graphics seamlessly blend with the physical environment 253.

In an embodiment, the 3D medical headset 284 is operable to play, run or otherwise execute graphical data files 295 (shown in FIG. 27) of various formats, including MP4, AVI, MKV, MPEG, MOV, QT, AVCHD, FLV, SWF, APNG, BMP, GIF, JPEG, PNG, SVG, TIFF and GIF. In an embodiment, the 3D medical headset 284 is operable to play, run or otherwise execute graphical data files 295 that are specifically configured or formatted for generating different types of 3D visual effects 286, including 360 video format, VR video format, monoscopic 360 video format, stereoscopic 3D 360 video format and VR180 video format, and VR 180 3D video format.

In an embodiment, the 3D medical headset 284 can be operated and used in a full room VR also known as VR cave. The full room VR includes a space bound by at least three walls. Each such wall projects high definition graphics. The subject 112, wearing the 3D medical headset 284 in the full room VR, experiences the 3D visual effect 286.

In an embodiment, the front surface 196 of the face assembly 166 includes or defines an opening or window. In this embodiment, the 3D medical headset 284 enables the subject 112 to peer through the window to see the physical environment 253, including graphics displayed on a television or other screen. Depending on the embodiment, such graphics can be 3D-formatted for generating a 3D visual effect 286, as described above.

In an embodiment, the face assembly 166 of the 3D medical headset 284 includes all of the parts, structure, elements and functionality as the Google Cardboard™ product made by Google LLC. All of the specifications of such product are hereby incorporated by reference into this disclosure.

In another embodiment, the 3D medical headset 284 includes all of the parts, structure, elements and functionality as the Vive™ virtual reality headset products made by HTC Corporation. All of the specifications of such products are hereby incorporated by reference into this disclosure. One such Vive™ product includes a plurality of handheld or hand-holdable devices that enable users to provide inputs to such Vive™ product, including controllers, buttons, sticks and track pads. The Vive™ eye-tracker of such product (including the eye movement sensors 246 and pupil resizing sensors 248) capture an image of the eye, extract the region-of-interest (ROI), and detect the pupil position within the eye 254 and relative the sensor area. Such Vive™ eye-tracker takes snapshots of the eyes 161, 163 with high frequency to capture the eye movements, preferably at a rate over sixty hertz. Such Vive™ eye-tracker then processes the images within its processing unit or sends the images to the programmed processor 151 to process the images. Such Vive™ eye-tracker can establish the ROI using suitable algorithms stored in the medical system 114.

As described below, the medical system 114 and system data 125 can include data derived through machine learning by a deep learning network, such as the YOLO network. In such case, such Vive™ eye-tracker is operable to extract the pupil position by using such derived data with weight factors configured to precisely detect the pupil's center position. The pupil position can also be detected by increasing the contrast of the image and applying a threshold to isolate the pupil position from the rest of the image. Such Vive™ eye-tracker also detects the openness level of the eye by analyzing the distance between the eyelids, where a value of 0 indicates the eyes are closed, and a value of 1 indicates that eyes are fully open. Such Vive™ eye-tracker analyzes the image of the eye to measure the pupil diameter in each image.

In yet another embodiment, the 3D medical headset 284 includes all of the parts, structure, elements and functionality as the Oculus Rift™ virtual reality headset products made by Facebook Inc. All of the specifications of such products are hereby incorporated by reference into this disclosure.

In still another embodiment, the 3D medical headset 284 includes all of the parts, structure, elements and functionality as the PlayStation™ virtual reality headset products made by the Sony Corporation. All of the specifications of such products are hereby incorporated by reference into this disclosure.

9. Tests Using Wearable Device

In an embodiment, the medical assembly 110 (whether including the wearable device 124, the medical headset 162 or the 3D medical headset 284) is configured and operable to conduct a plurality of eye tests. Each eye test involves at least one graphic generated by the medical assembly 110.

Figure 34:
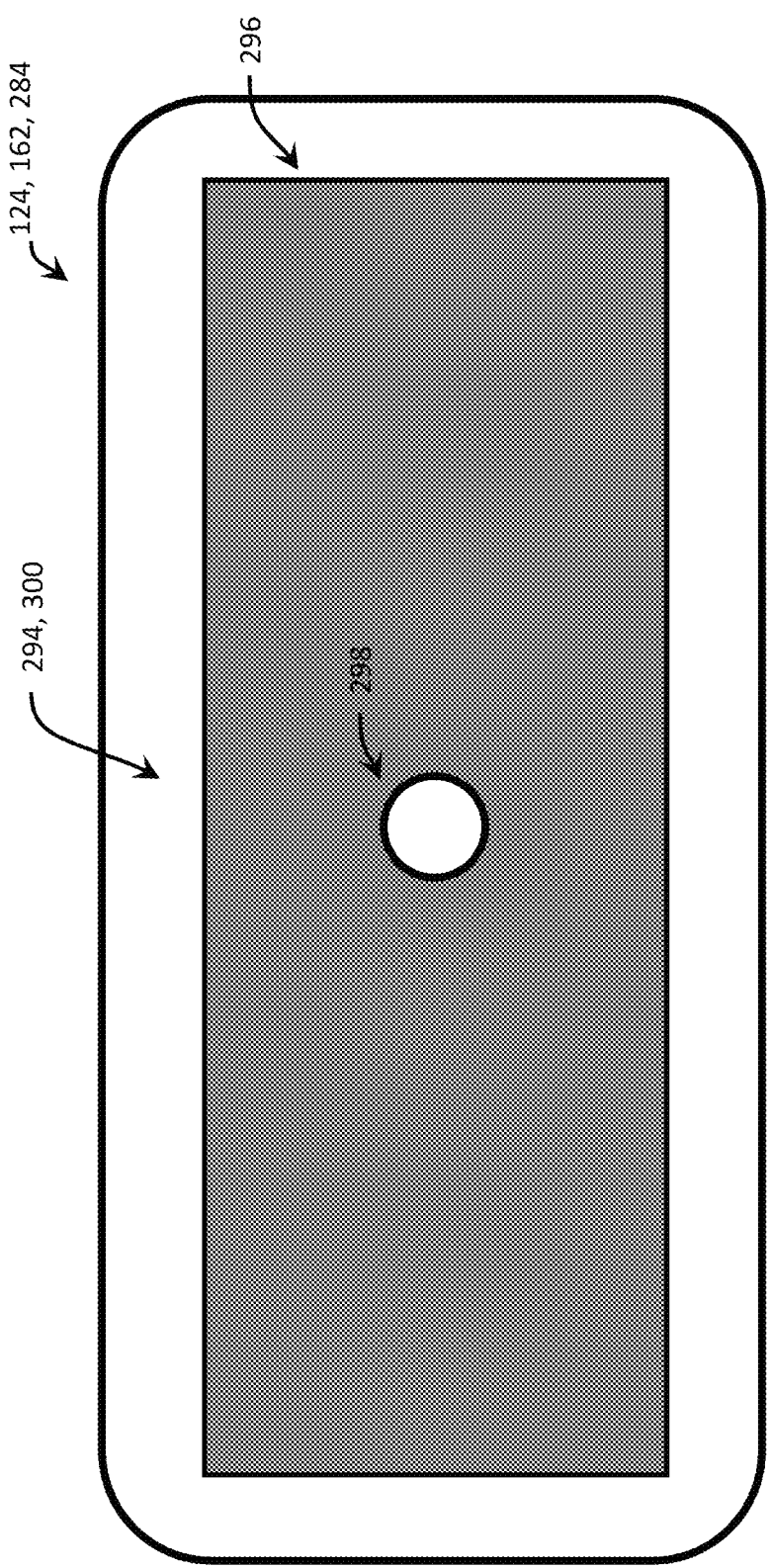
FIG. 34 is a rear view of the 3D medical headset of FIG. 32, illustrating the first frame of an example of a pursuit graphic.
Figure 35:
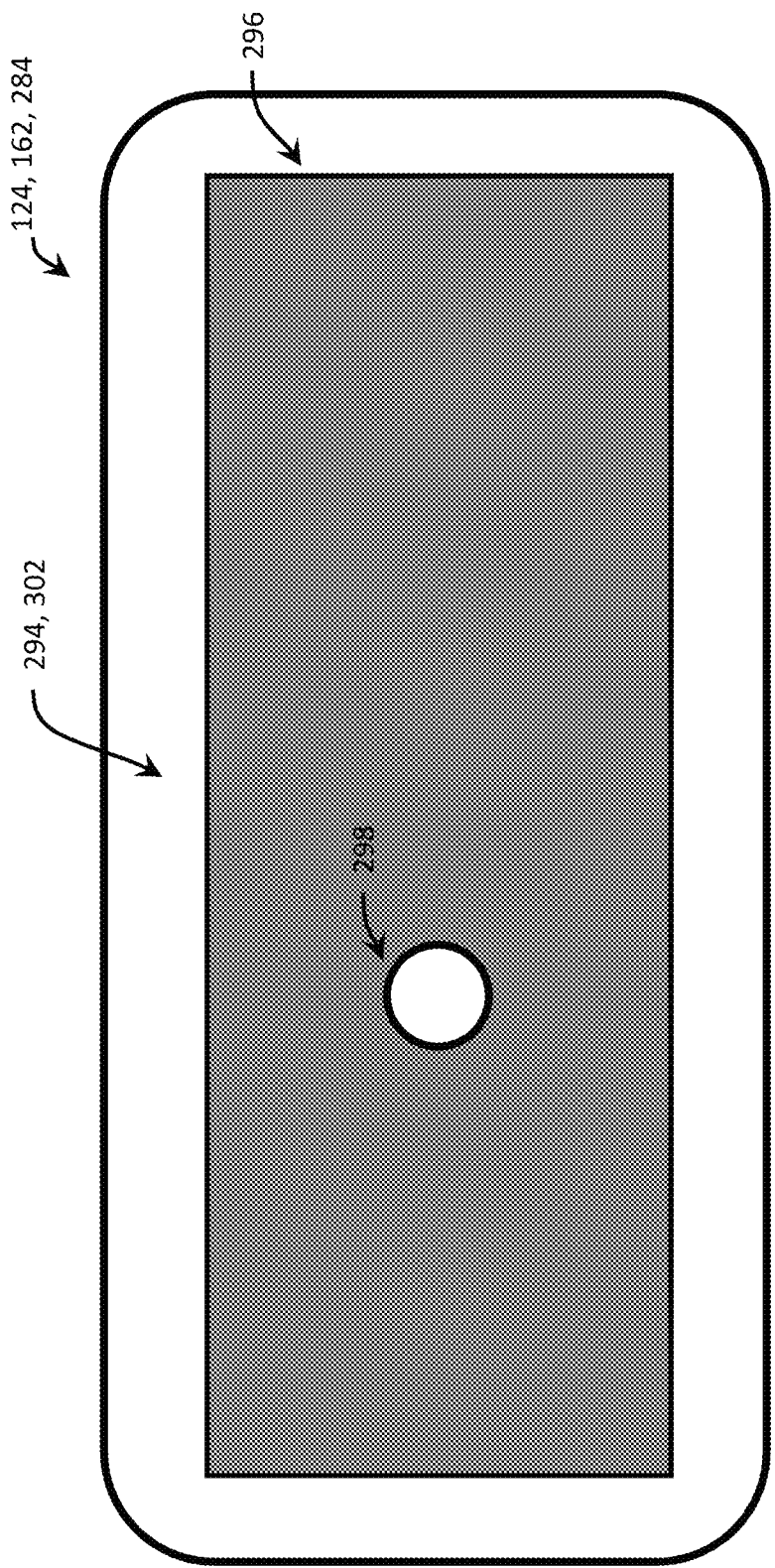
FIG. 35 is a rear view of the 3D medical headset of FIG. 32, illustrating the second frame of the example of the pursuit graphic of FIG. 34.
Figure 36:
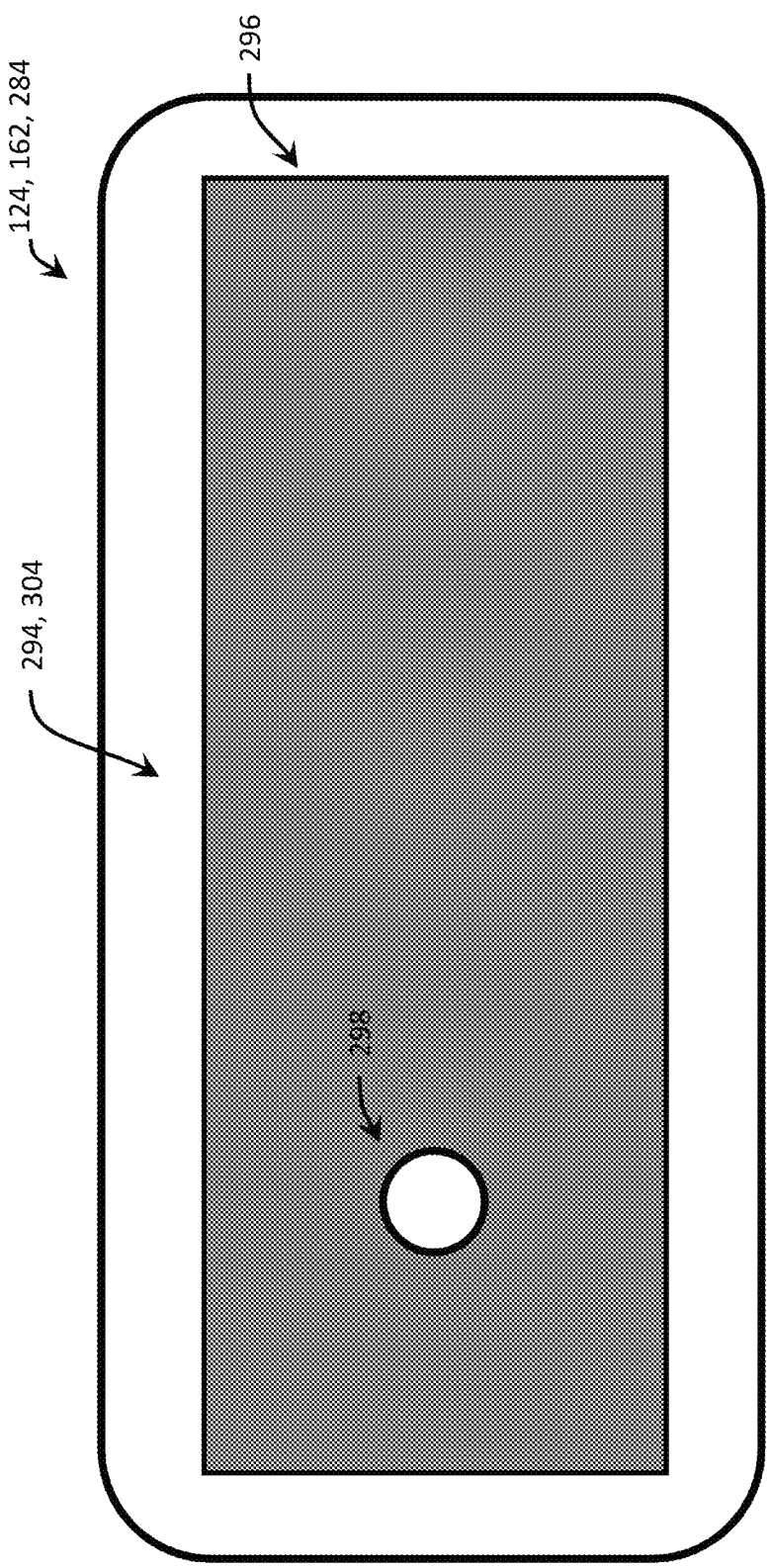
FIG. 36 is a rear view of the 3D medical headset of FIG. 32, illustrating the third frame of the example of the pursuit graphic of FIG. 34.

For a pursuit eye movements test, listed in Table 1 below, the medical assembly 110 generates a pursuit graphic 294, as illustrated in FIGS. 34-36. The pursuit graphic 294 includes a background image 296 and a sprite or traveling stimulus 298 that moves relative to the background image 296. The traveling stimulus 298 moves horizontally, vertically and a combination thereof. In the example shown in FIGS. 34-36, the pursuit graphic 294 includes a video having a plurality of images or frames 300, 302, 304. The pursuit graphic 294 shows the traveling stimulus 298 moving along a leftward, horizontal path. For this example, the medical assembly 110 or health care provider audibly or visually prompts the subject 112 to use the subject's eyes to follow the movement of the traveling stimulus 298. The pursuit eye movement test includes movement of the traveling stimulus 298, relative to the background image 296, along a horizontal path (leftward and rightward), vertical path (upward and downward) and a combination of such movements.

For the pursuit eye movements test, the subject 112 might tend to move the subject's head 160 in an attempt to follow the traveling stimulus 298. This is because the medical assembly 110 is operable, at times, to dynamically adjust graphics depending on movement of the head 160 relative to the physical environment 253. For example, the medical assembly 110 is operable to generate a 3D visual effect 286, as described above. As a result of the 3D visual effect 286, the subject 112 could rotate the subject's head 160 in various directions, and the viewable graphics would change to show different graphics or views based on the head rotations. This behavior by the subject 112 can compromise or skew the results of the pursuit eye movements test and other eye tests.

To address this problem, the system logic 118 includes a head movement de-coupler 303, as shown in FIG. 29. According to the head movement de-coupler 303, the medical assembly 110 is configured to de-couple head movements from any changes in the pursuit graphic 294 or in other graphics intended to be experienced without head movement. In particular, the medical assembly 110 disables or deactivates the 3D visual effect 286 to the extent that the pursuit graphic 294 is generated (and remains generated) independent of any movement of the head 160 relative to the physical environment 253.

Figure 37:
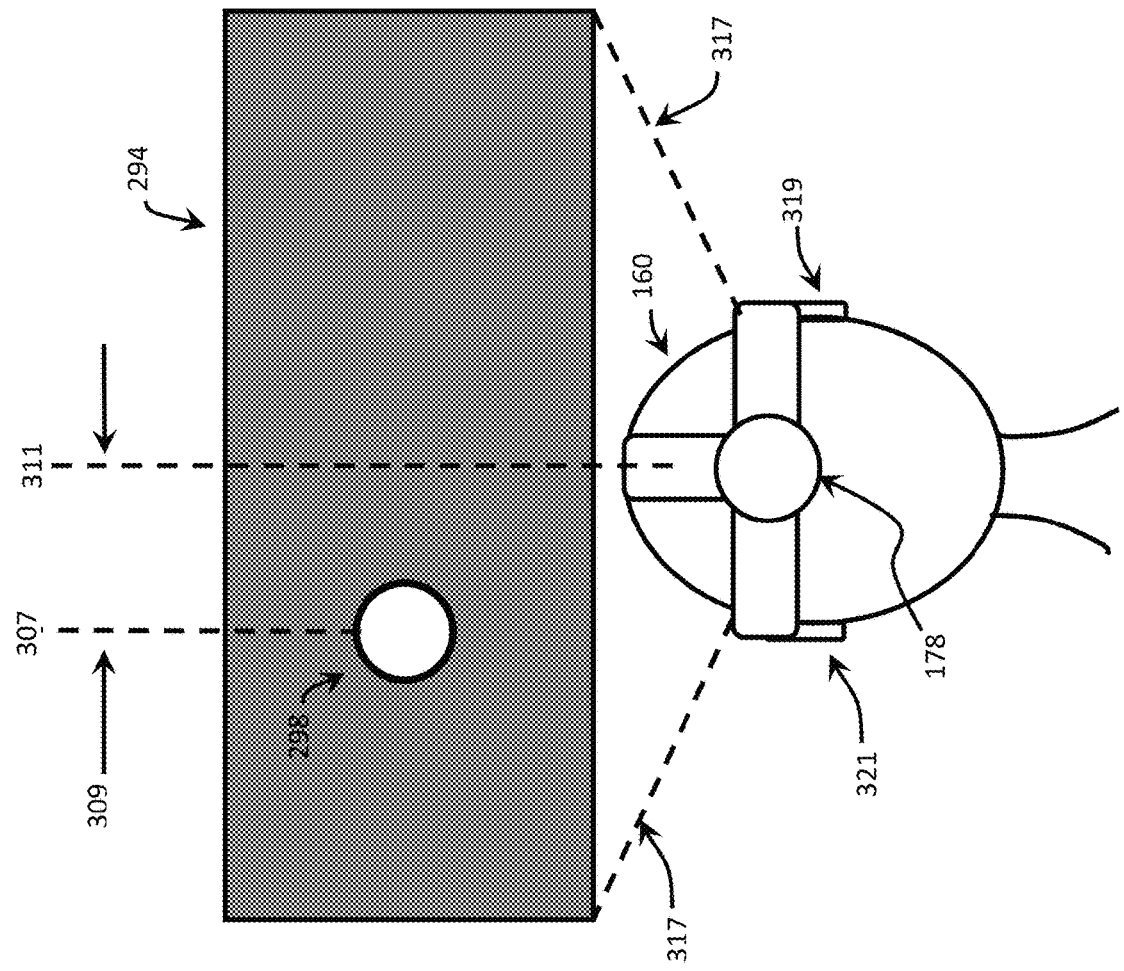
FIG. 37 is a rear view of the 3D medical headset of FIG. 32, illustrating a subject's head having a first angular position relative to an example of a pursuit graphic.
Figure 38:
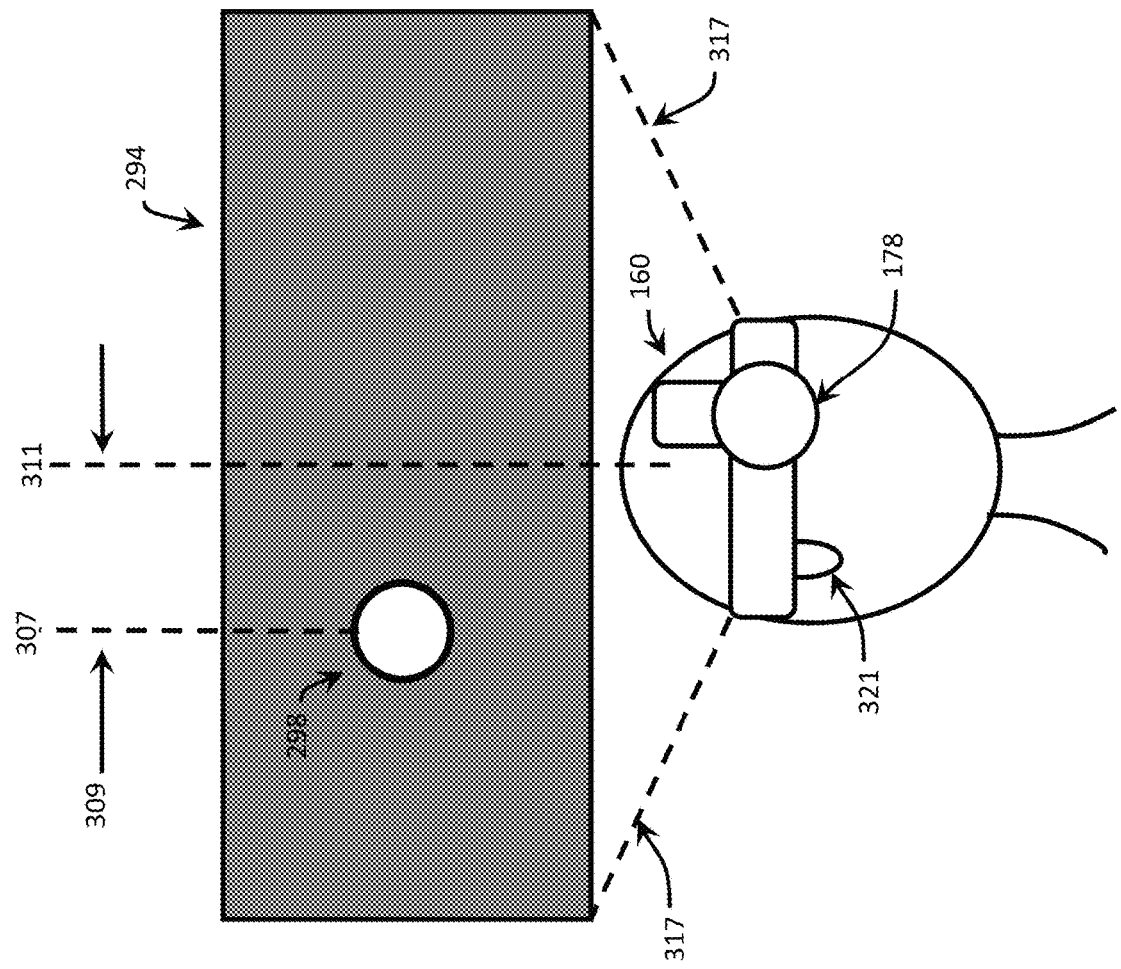
FIG. 38 is a rear view of the 3D medical headset of FIG. 32, illustrating a subject's head having a second angular position relative to the example of the pursuit graphic of FIG. 37, wherein the pursuit graphic does not change in response to a change to the second angular position of the head.

In the example shown in FIGS. 37-38, the traveling stimulus 298 of the pursuit graphic 294 has an initial graphic position 307. This is because, during the test, the traveling stimulus 298 moved a horizontal distance 309 to the left of the center line 311 of the pursuit graphic 294. In response, the subject 112 turned the head 160 (having right and left ears 319, 321) twenty degrees to the left in a yaw rotation 278, and the medical assembly 110 kept the pursuit graphic 294 so that the traveling stimulus 298 retained the initial graphic position 307. As a result, the subject 112 has the visual experience or impression that the entire pursuit graphic 294 is fixed on a sheet of paper physically attached to the subject's head 160 via rigid arms 317. Accordingly, the head movement de-coupler 303 prevents or inhibits the head movement from affecting or impairing the testing of the eyes in certain tests, such as the pursuit eye movements test.

In an embodiment, the medical assembly 110 activates a graphic change mode for certain eye tests. During the graphic change mode, the medical assembly 110 automatically displays a change in one or more of the graphics depending on the movement of the subject's head 160. When the medical assembly 110 is used to perform other types of eye tests, such as the pursuit movements test, the medical assembly 110 is operable to deactivate the graphic change mode. When the graphic change mode is deactivated, the medical assembly 110 generates the graphics independent of any head movement. Depending on the embodiment, the deactivation can occur automatically or in response to a control input provided by a user.

Figure 39:
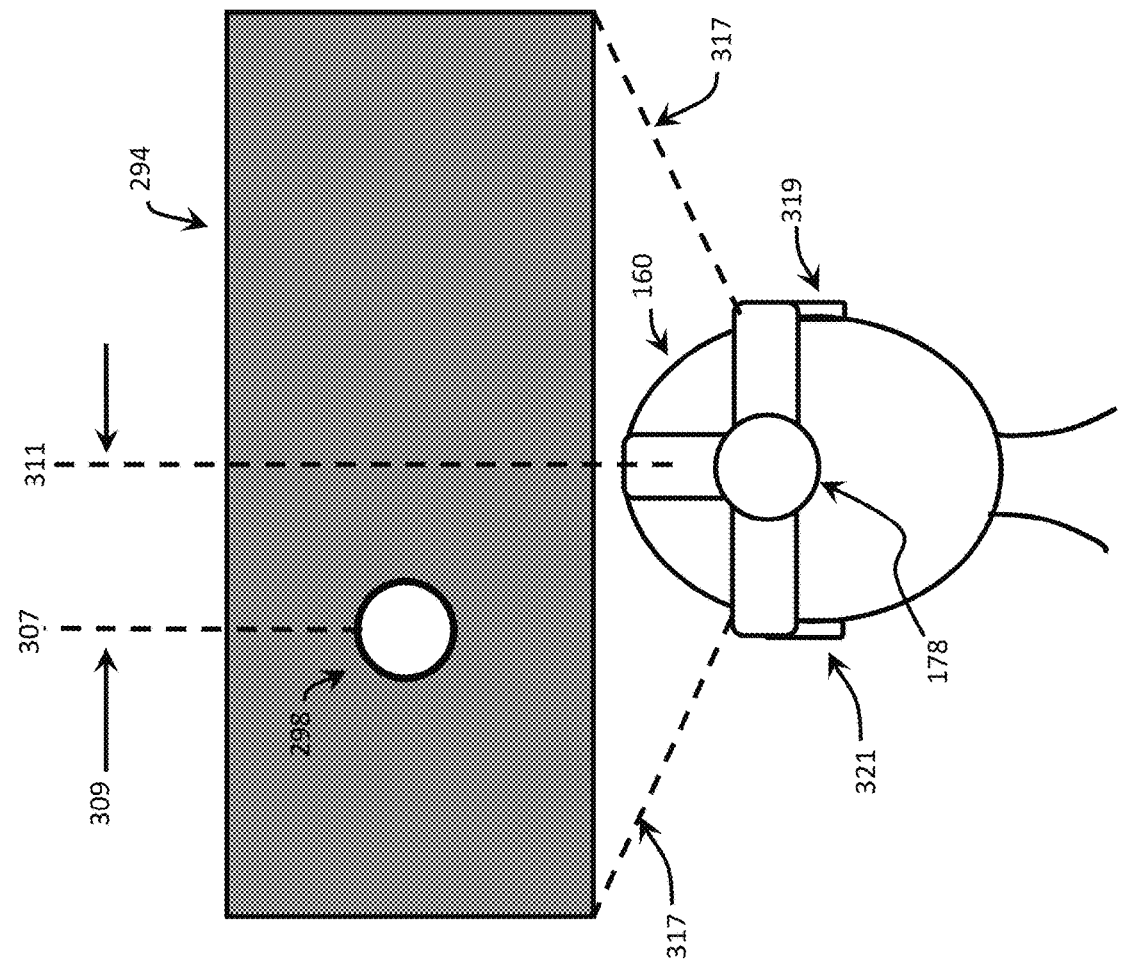
FIG. 39 is a rear view of the 3D medical headset of FIG. 32, illustrating a subject's head having a first angular position relative to an example of a pursuit graphic.
Figure 40:
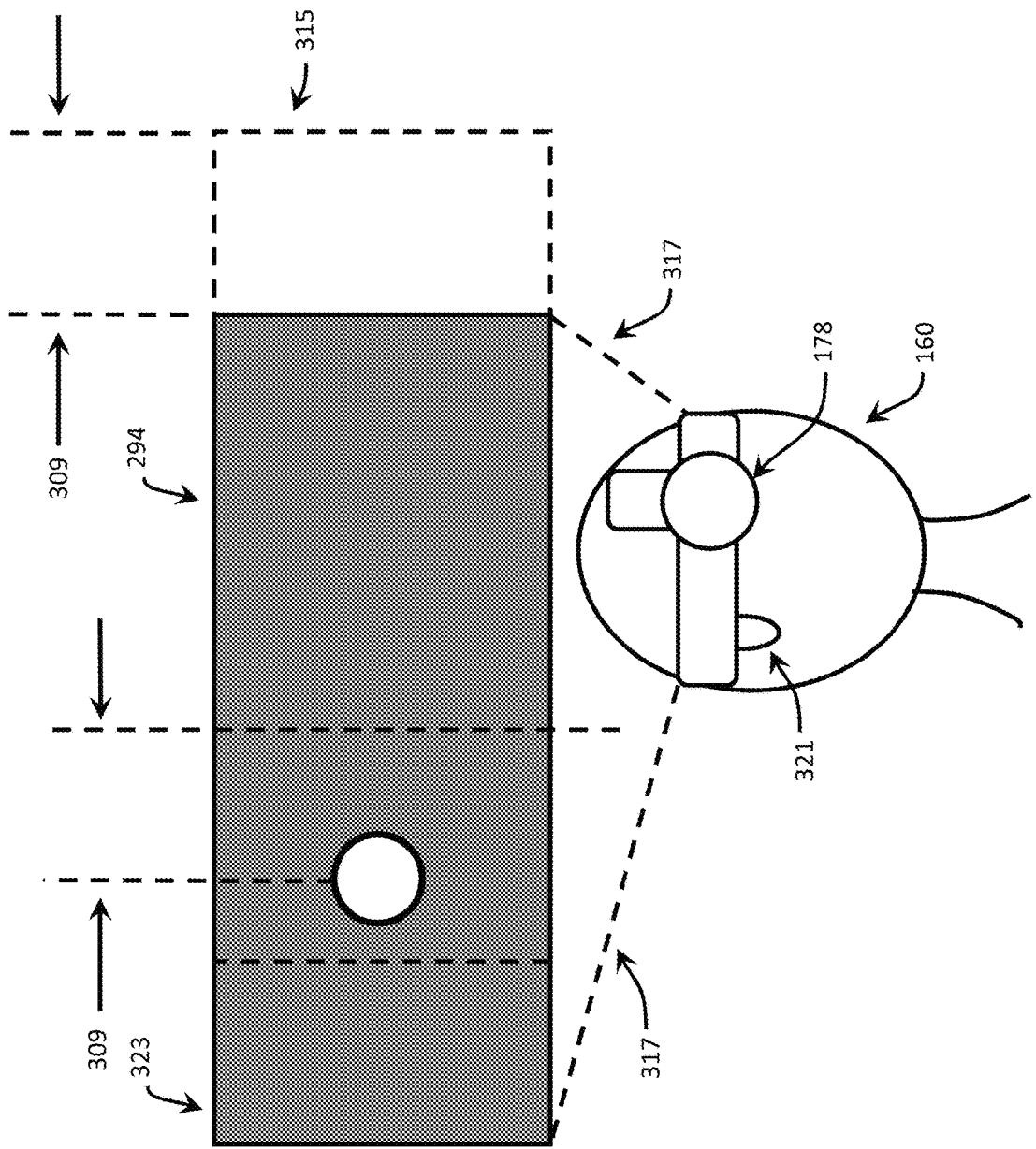
FIG. 40 is a rear view of the 3D medical headset of FIG. 32, illustrating a subject's head having a second angular position relative to the example of the pursuit graphic of FIG. 39, wherein the entire pursuit graphic moves in response to a change to the second angular position of the head.

Referring to FIGS. 29 and 39-40, in another embodiment, the system logic 118 includes a head movement graphical compensator 305 as an alternative to the head movement de-coupler 303. The head movement graphical compensator 305 directs the medical assembly 110 to dynamically adjust the position of the entire pursuit graphic 294 depending on any movement of the head 160 relative to the physical environment 253. The head movement graphical compensator 305 aids in the accurate sensing and collection of sensed eye parameters 362 regardless of the head movement relative to the physical environment 253. The head movement graphical compensator 305 directs the medical assembly 110, based on sensed head movement parameters 364, to generate the visual effect (3D, immersive or otherwise) that the entire pursuit graphic 294 moves based on such head movement. In the example shown in FIGS. 39-40, the pursuit graphic 294 has the initial graphic position 307. During the test, the traveling stimulus 298 has moved the horizontal distance 309 to the left of the center line 311 of the pursuit graphic 294. The subject 112 turned the head 160 twenty degrees to the left in a yaw rotation 278, and the medical assembly 110 dynamically collected data regarding such twenty degree head movement. Based on such data, the medical assembly 110 generated the pursuit graphic 294 in a way that produced the visual effect (3D, immersive or otherwise) that the entire pursuit graphic 294 has horizontally moved the horizontal equivalent 313 of twenty degrees leftward, which corresponds to such twenty degree head movement. As a result of such movement from the initial position 315, the entire pursuit graphic 294 has a compensated position 323. Consequently, the subject 112 has the visual experience or impression that the entire pursuit graphic 294 is physically connected to the head 160 via rigid arms 317 so that moving the head 160 does not help the subject 112 follow the pursuit graphic 294. Accordingly, the head movement graphical compensator 305 prevents or inhibits the head movement from affecting or impairing the testing of the eyes.

Figure 41:
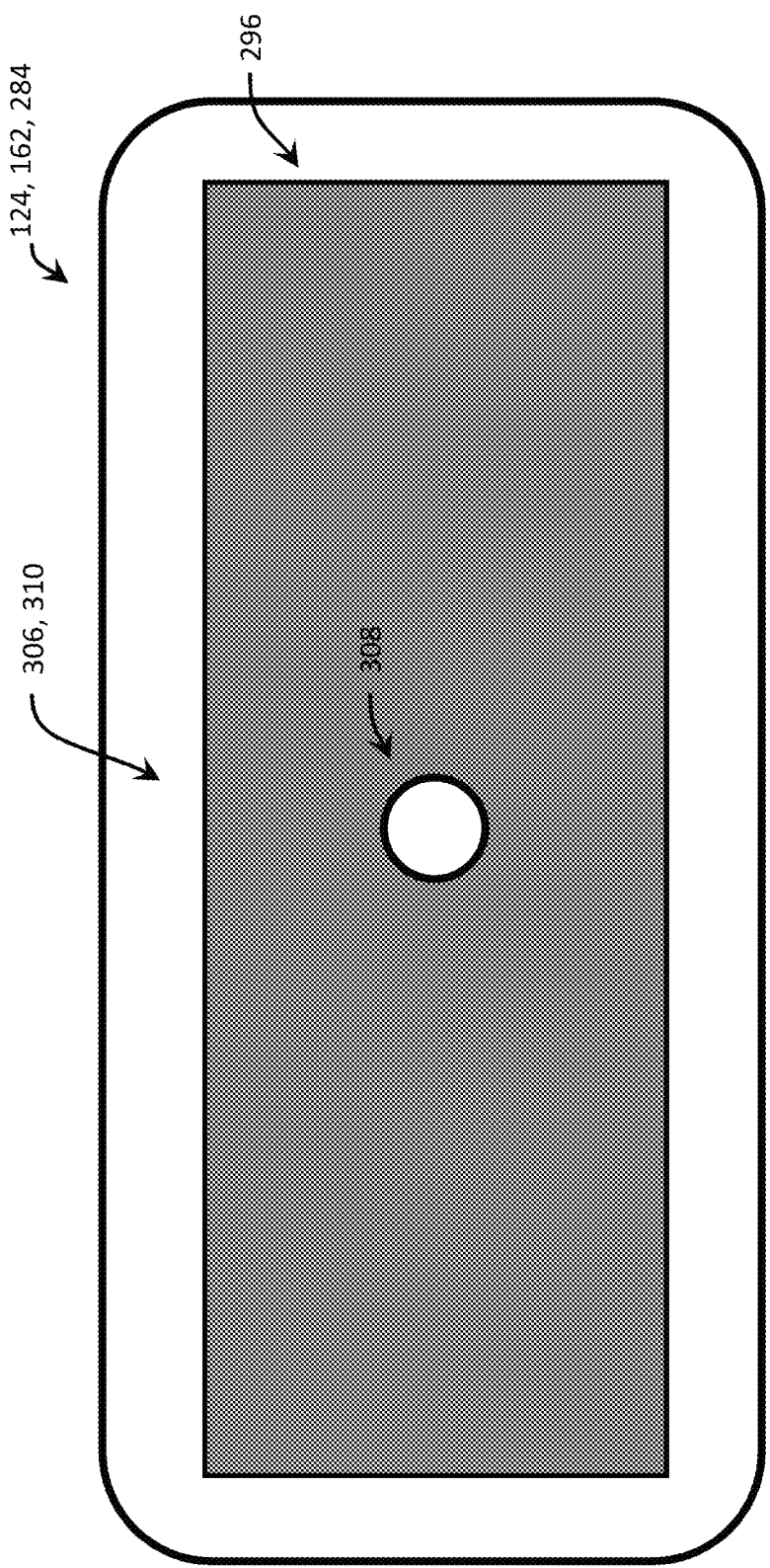
FIG. 41 is a rear view of the 3D medical headset of FIG. 32, illustrating the first frame of an example of a popup graphic.
Figure 42:
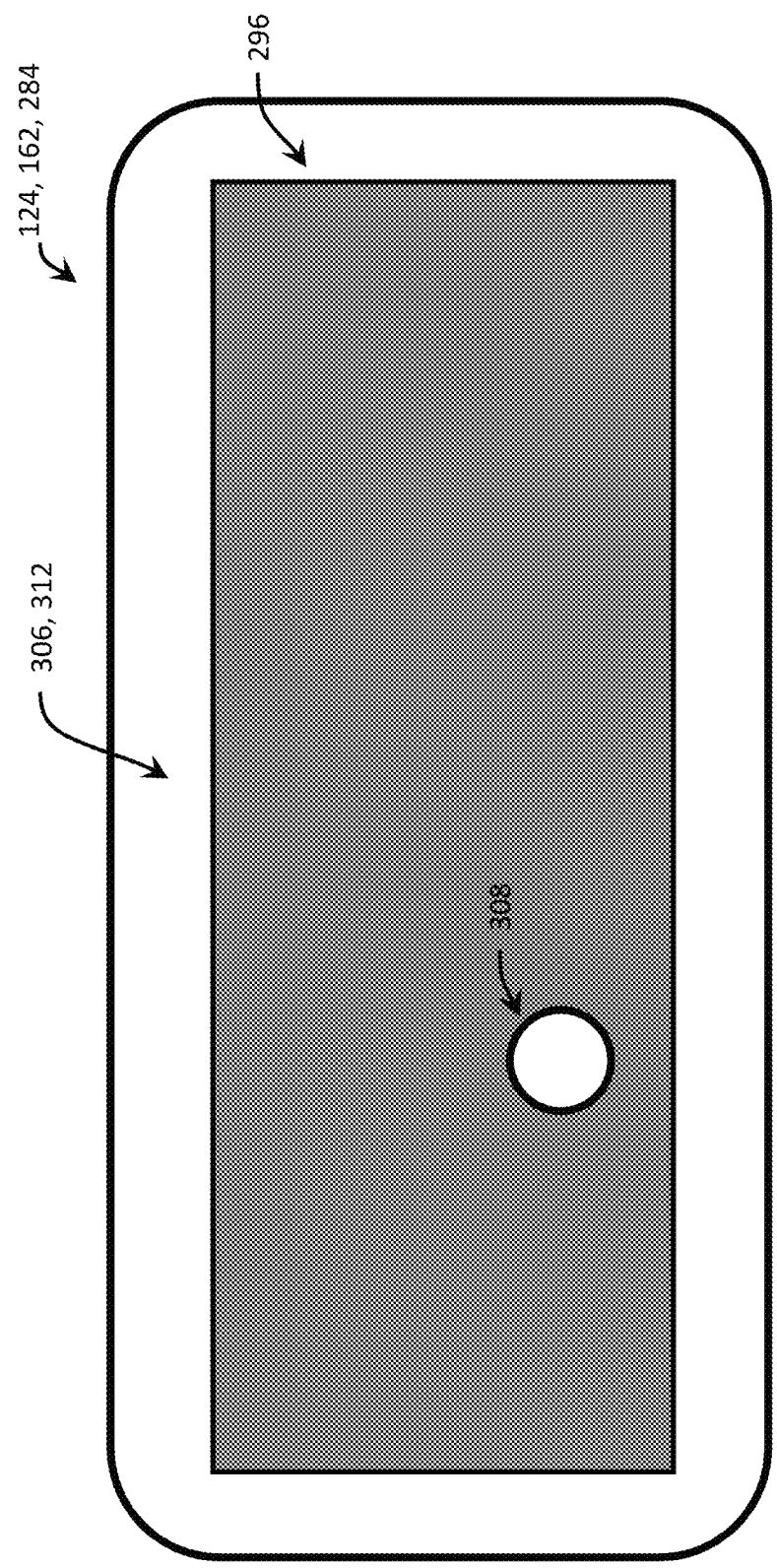
FIG. 42 is a rear view of the 3D medical headset of FIG. 32, illustrating the second frame of the example of the popup graphic of FIG. 41.
Figure 43:
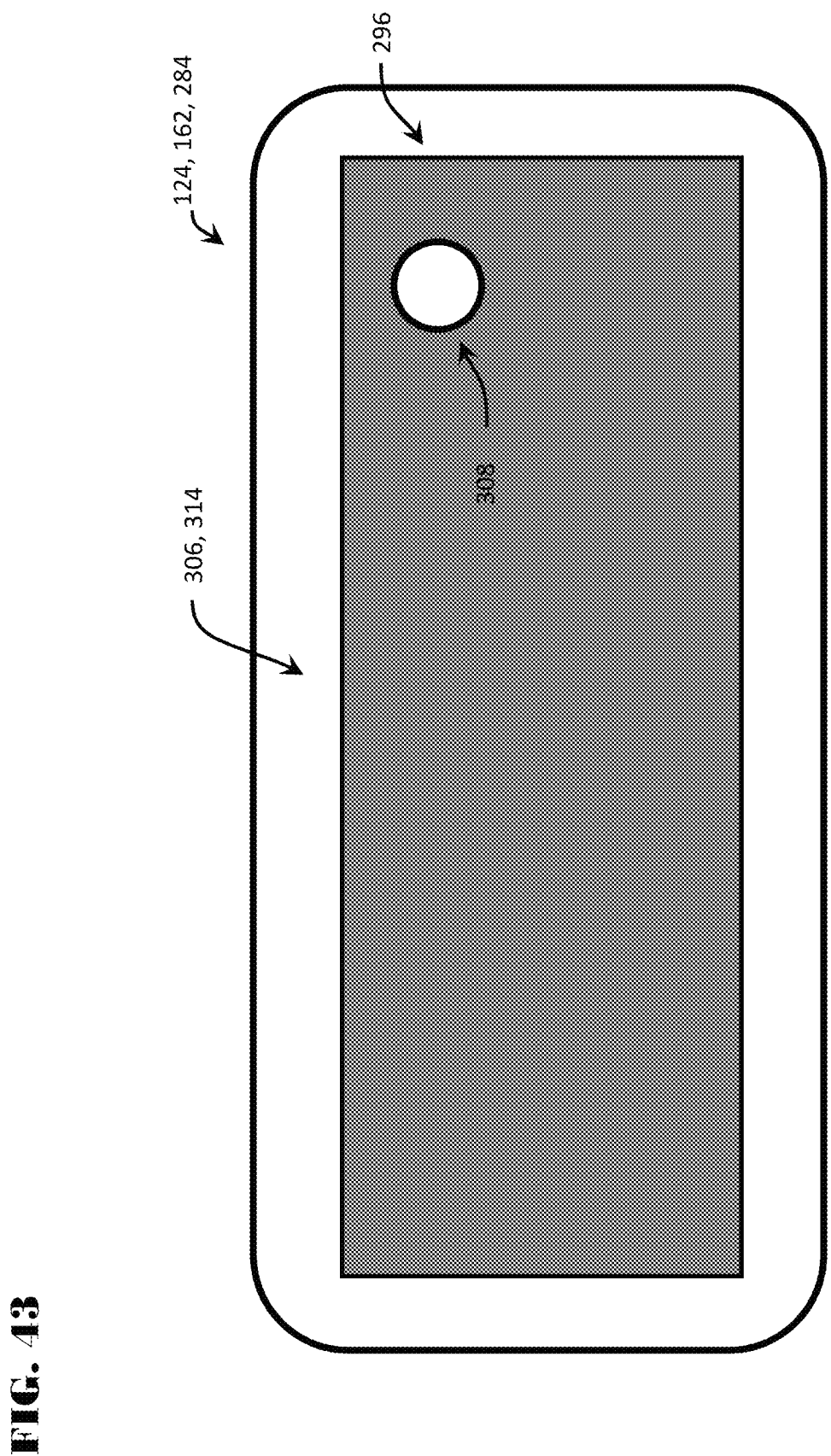
FIG. 43 is a rear view of the 3D medical headset of FIG. 32, illustrating the third frame of the example of the popup graphic of FIG. 41.

For a saccadic eye movements test, listed in Table 1 below, the medical assembly 110 generates a popup graphic 306 illustrated in FIGS. 41-43. The popup graphic 306 includes the background image 296 and a sprite or popup stimulus 308. The popup stimulus 308 appears and then disappears at different locations on the background image 296. In this example, the popup graphic 306 includes a video having a plurality of images or frames 310, 312 314. The popup graphic 306 shows the popup stimulus 308 popping-up (appearing) and disappearing at predetermined locations on the background image 296. For this example, the medical assembly 110 or health care provider audibly or visually prompts the subject 112 to use the subject's eyes to look at each popup stimulus 308 as soon as it appears. As described for the pursuit eye movements test, the medical assembly 110 also uses the head movement de-coupler 303 to prevent or inhibit head movement from affecting the results of the saccadic eye movements test. The head movement de-coupler 303 alleviates or resolves the problems caused by the subject moving the head 160, as described above.

Figure 44:
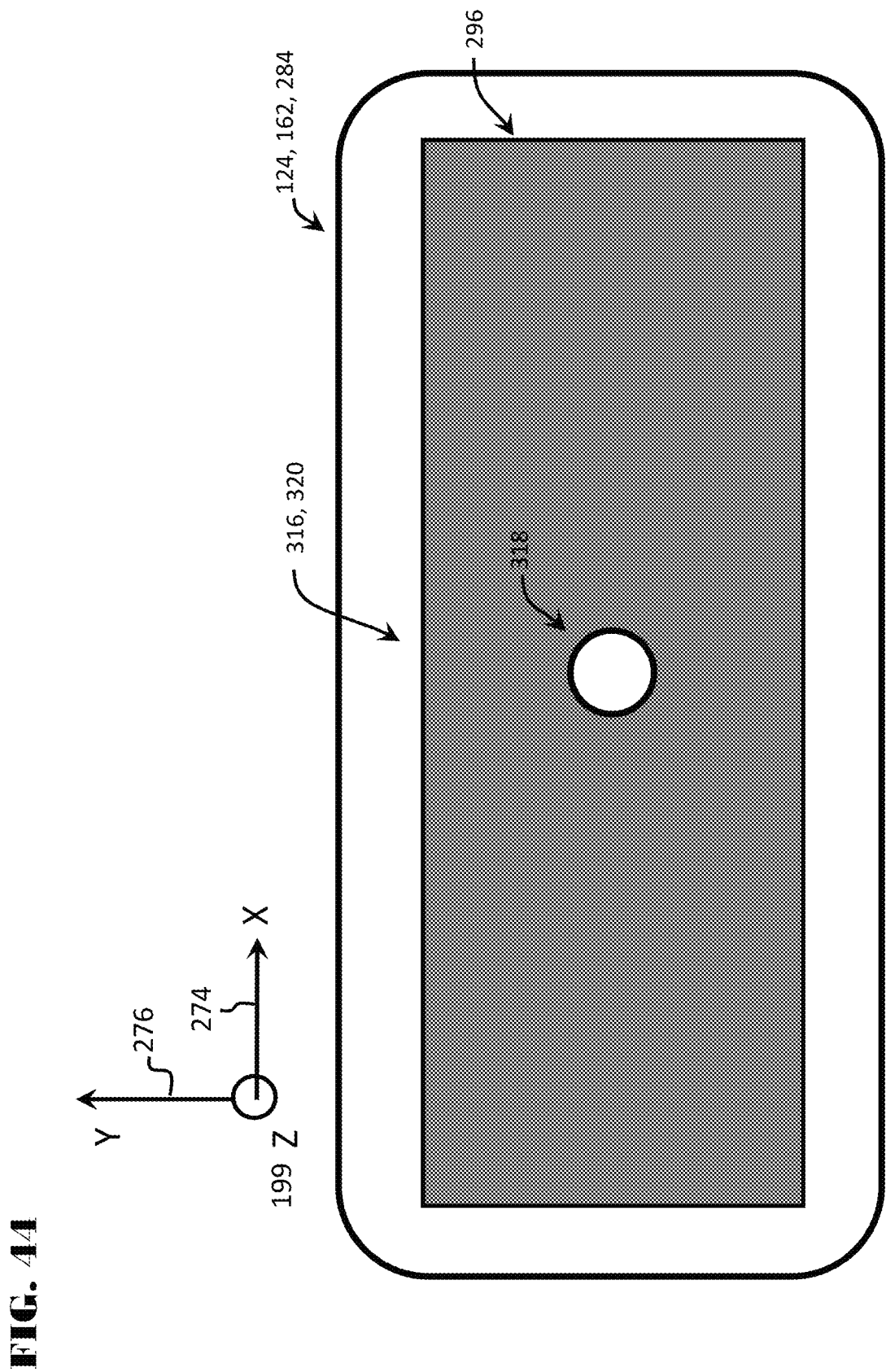
FIG. 44 is a rear view of the 3D medical headset of FIG. 32, illustrating the first frame of an example of a depth-traveling graphic.
Figure 45:
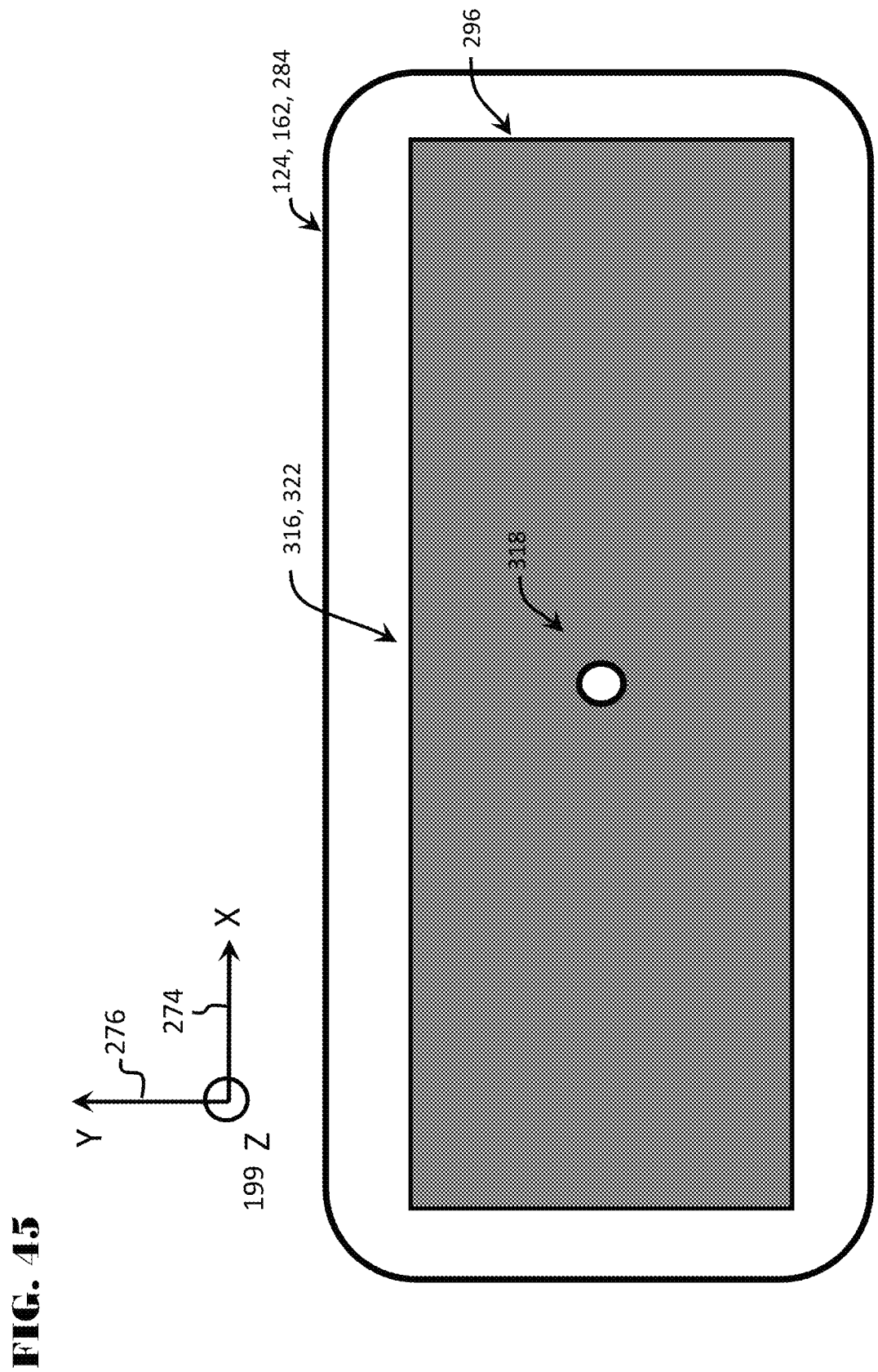
FIG. 45 is a rear view of the 3D medical headset of FIG. 32, illustrating the second frame of the example of the depth-traveling graphic of FIG. 44.
Figure 46:
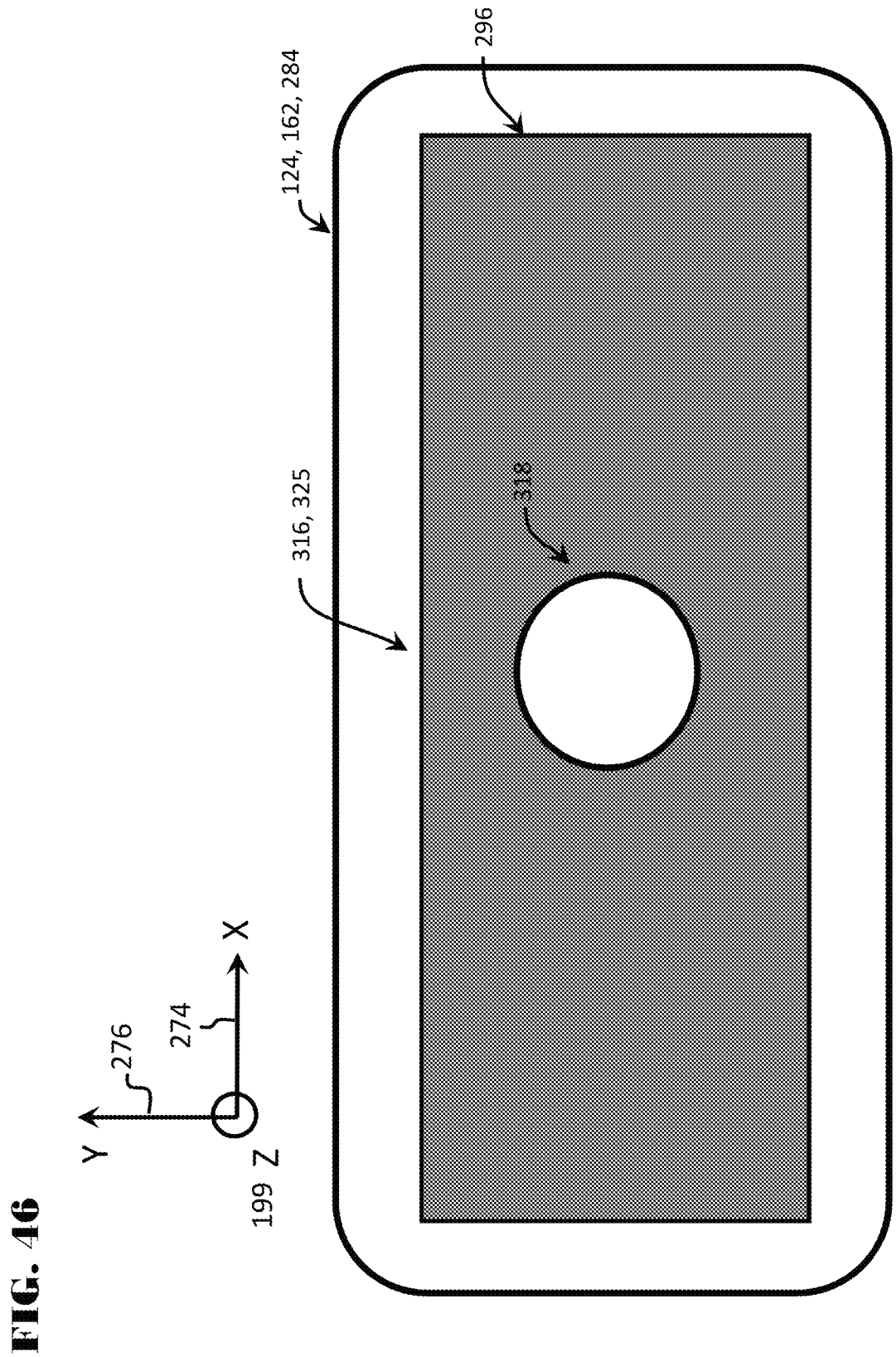
FIG. 46 is a rear view of the 3D medical headset of FIG. 32, illustrating the third frame of the example of the depth-traveling graphic of FIG. 44.

For a vergence eye test, listed in Table 1 below, the medical assembly 110 generates a depth-traveling graphic 316 illustrated in FIGS. 44-46. The depth-traveling graphic 316 includes the background image 296 and a sprite or depth stimulus 318. The medical assembly 110 causes a visual effect (3D, immersive or otherwise) that gives the subject 112 the impression that the depth stimulus 318 moves along the Z-axis 199 relative to the background image 296. This causes the subject 112 to think the depth stimulus 318 appears at different depths or distances from the subject's eyes along the Z-axis 199. In this example, the depth stimulus 318 includes a video having a plurality of images or frames 320, 322, 325. The depth-traveling graphic 316 shows the depth stimulus 318 moving from the initial location on Z-axis 199 relative to a point in the background image 196 as exemplified in FIG. 44, to a distance from such point (further from the subject 112) along the Z-axis 199 as exemplified in FIG. 45, to a distance from such point (closer to the subject 112) along the Z-axis 199 as exemplified in FIG. 46. For this example, the medical assembly 110 or health care provider audibly or visually prompts the subject 112 to use the subject's eyes to watch the depth stimulus 318 as it virtually moves along the Z-axis 199.

Figure 47:
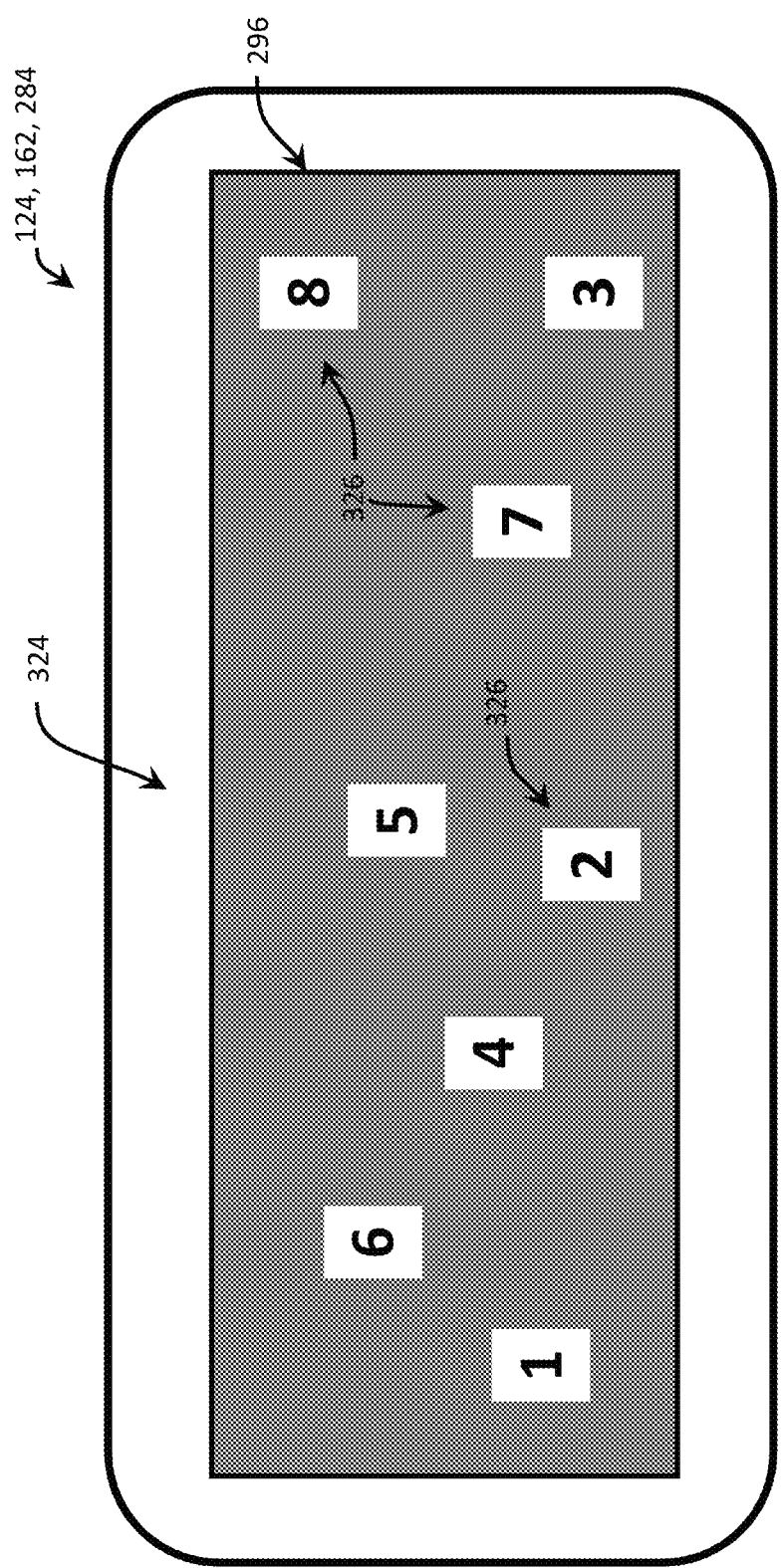
FIG. 47 is a rear view of the 3D medical headset of FIG. 32, illustrating an example of a gaze graphic.

For a spontaneous eye movements test, listed in Table 1 below, the medical assembly 110 generates a gaze graphic 324 illustrated in FIG. 47. The gaze graphic 324 includes the background image 296 and a plurality of gaze targets 326 exemplified as numerals one through eight. As an analysis for nystagmus, the medical assembly 110 or health care provider audibly or visually prompts the subject 112 to stare, gaze or fixate at each of the gaze targets 326 for a designated period of time. This can provide localizing clues for nystagmus.

Figure 48:
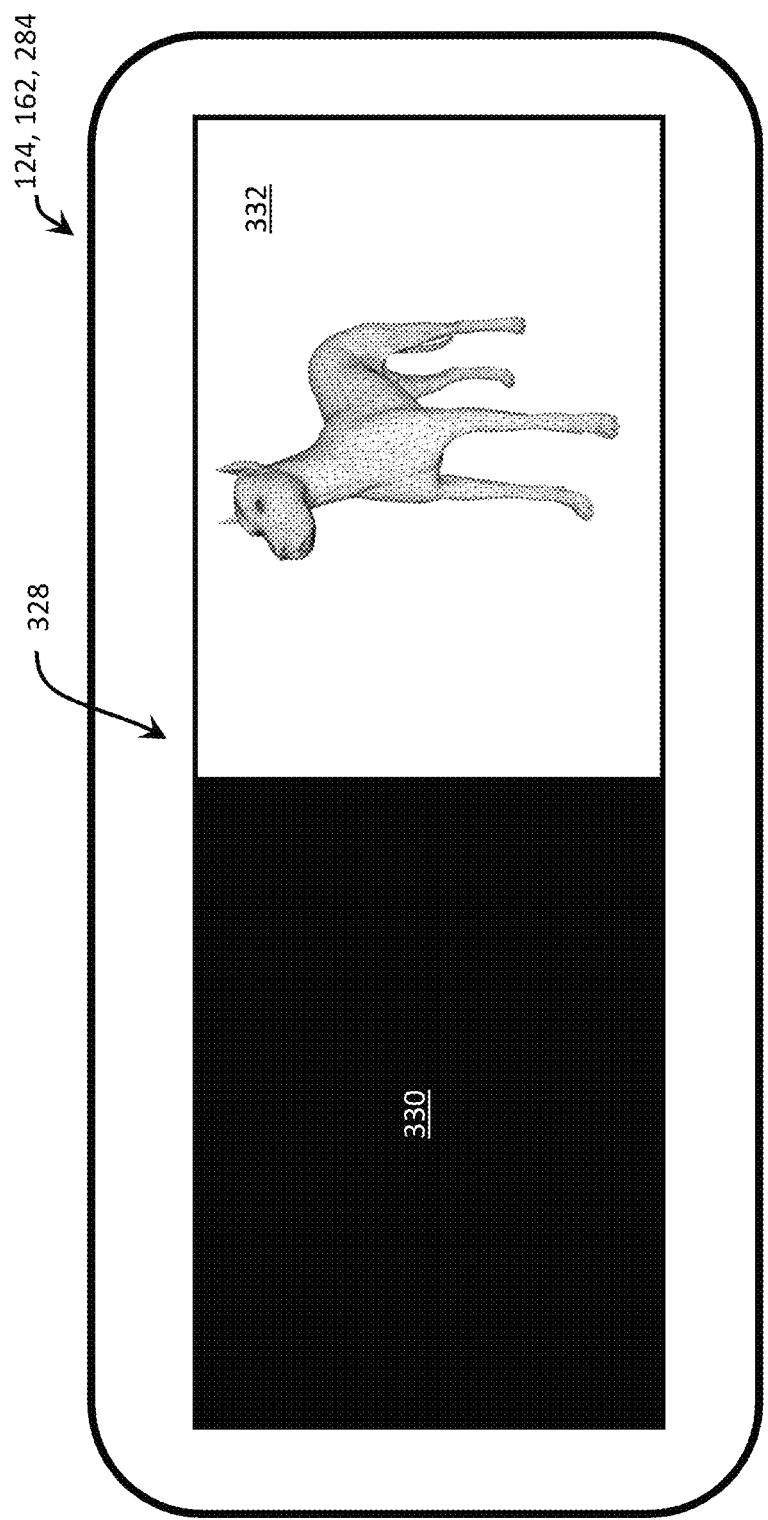
FIG. 48 is a rear view of the 3D medical headset of FIG. 32, illustrating an example of a split screen graphic, illustrating a left occlusion image displayed to block a left eye.
Figure 49:
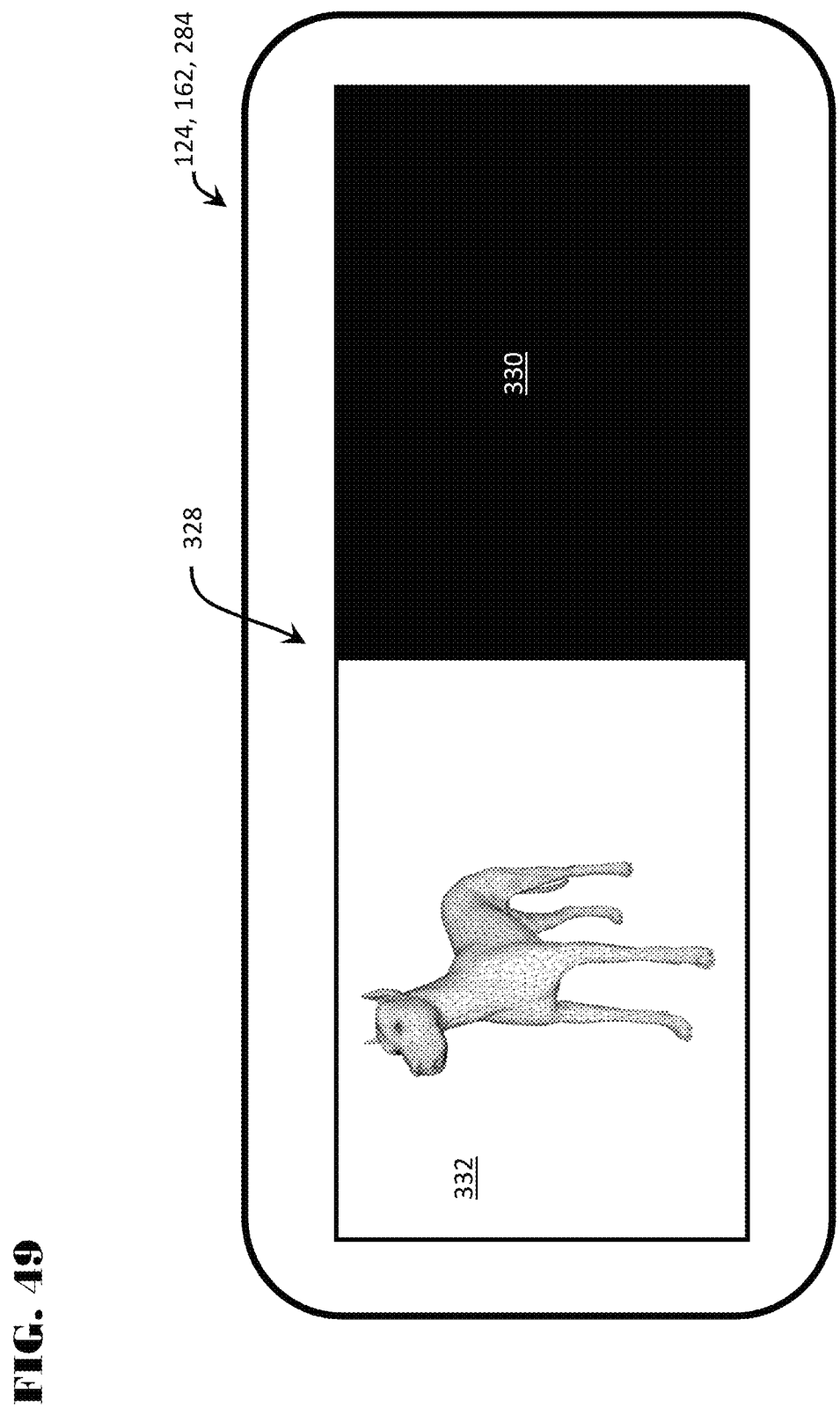
FIG. 49 is a rear view of the 3D medical headset of FIG. 32, illustrating an example of a split screen graphic, illustrating a right occlusion image displayed to block a right eye.

For a phoria-tropia test, listed in Table 1 below, the medical assembly 110 generates a split screen graphic 328, as illustrated in FIGS. 48-49. The split screen graphic 328 includes a single eye coverage, blockage or occlusion image 330 and a single eye stimulus 332. The medical assembly 110 alternatively displays the occlusion image 330 to independently test each of the eyes 161, 163. In this regard, the occlusion image 330 functions to cover and uncover each of the eyes 161, 163. In this example, the left occlusion image 330 covers the left eye 163 while the singe eye stimulus 332 is visible to the right eye 161, as exemplified in FIG. 48. Likewise, the right occlusion image 330 covers the right eye 161 while the single eye stimulus 332 is visible to the left eye 163, as exemplified in FIG. 49. The results of this type of cover-uncover testing can indicate the presence of phoria or tropia.

Figure 50:
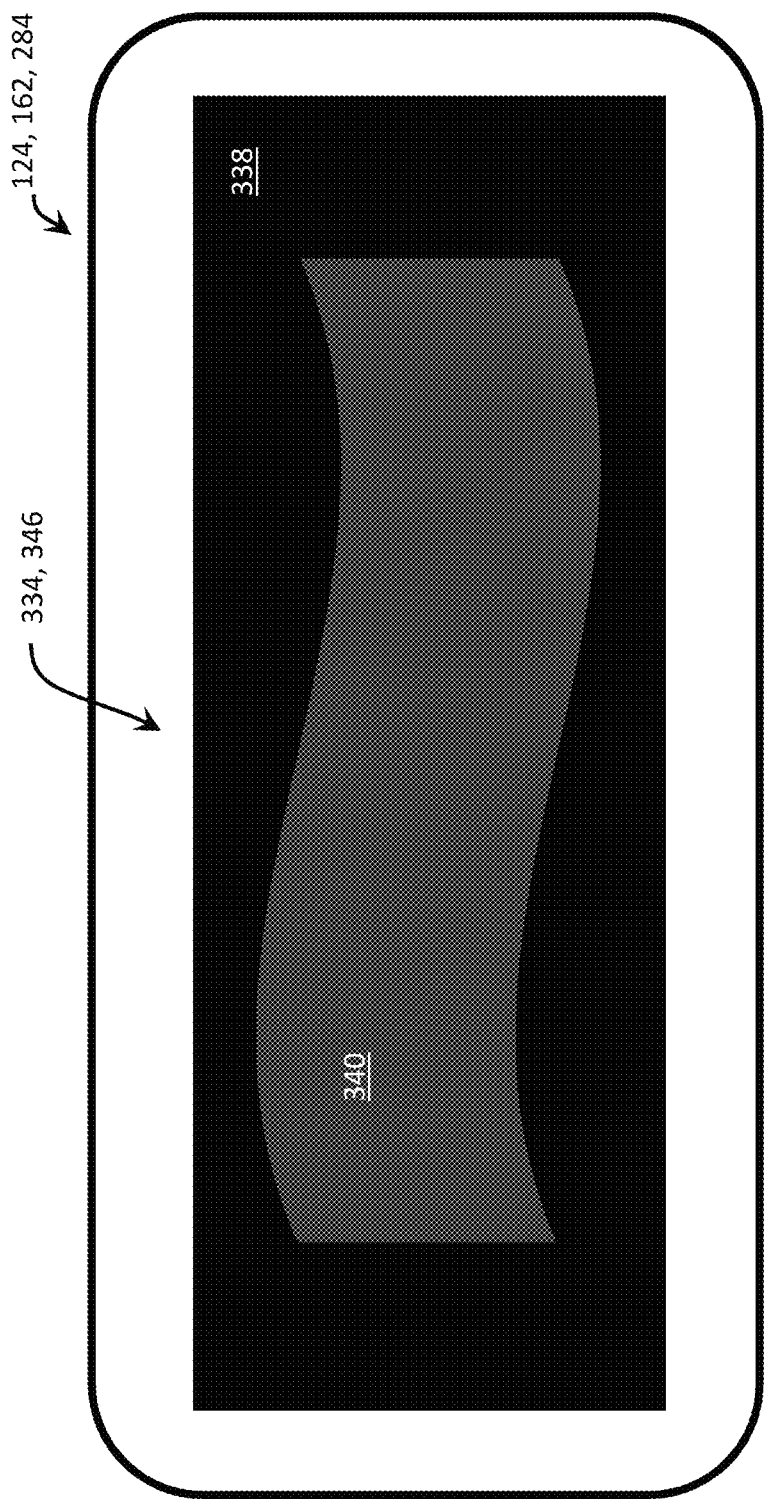
FIG. 50 is a rear view of the 3D medical headset of FIG. 32, illustrating the first frame of an example of a luminosity graphic.
Figure 51:
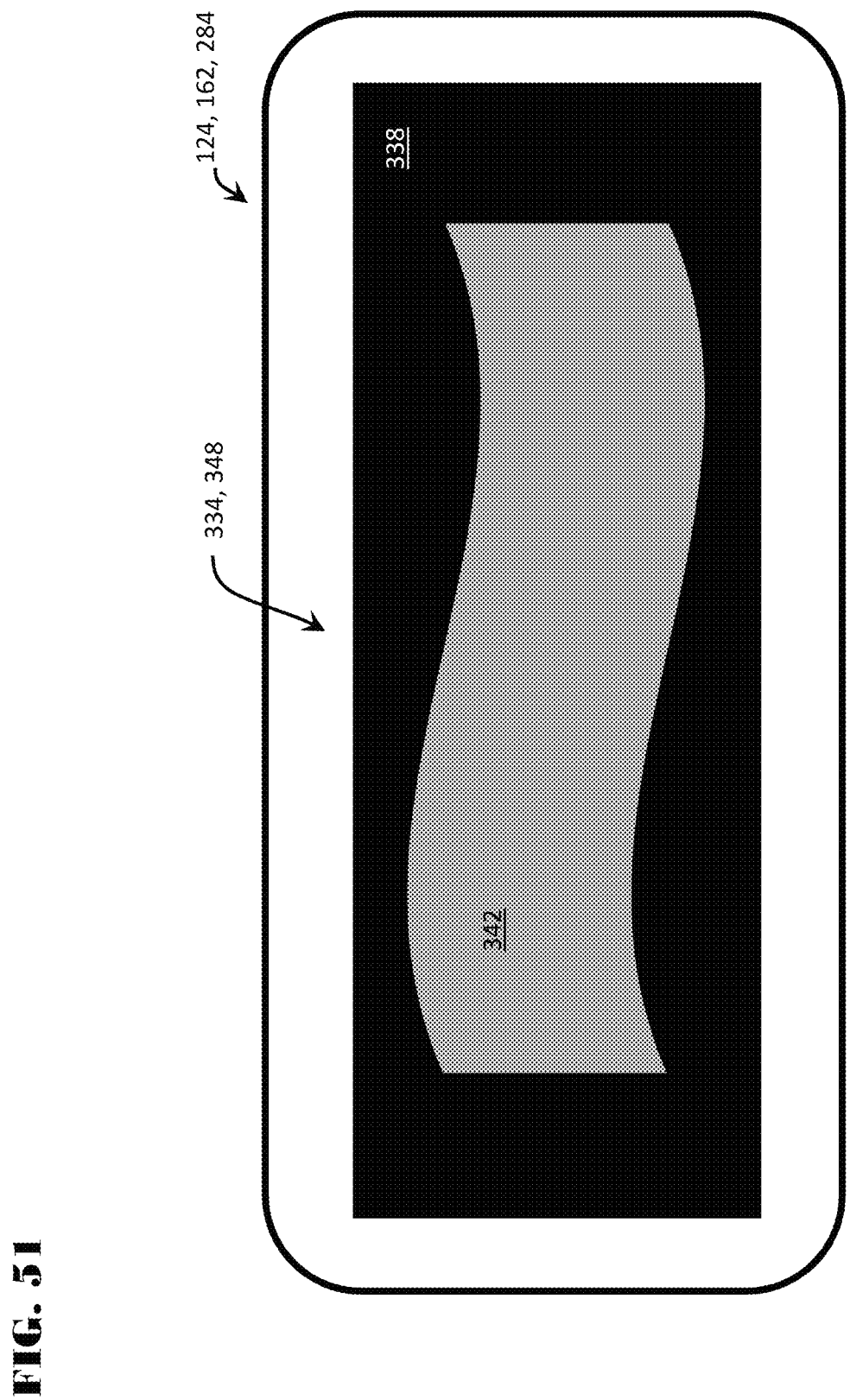
FIG. 51 is a rear view of the 3D medical headset of FIG. 32, illustrating the second frame of the example of the luminosity graphic of FIG. 50.
Figure 52:
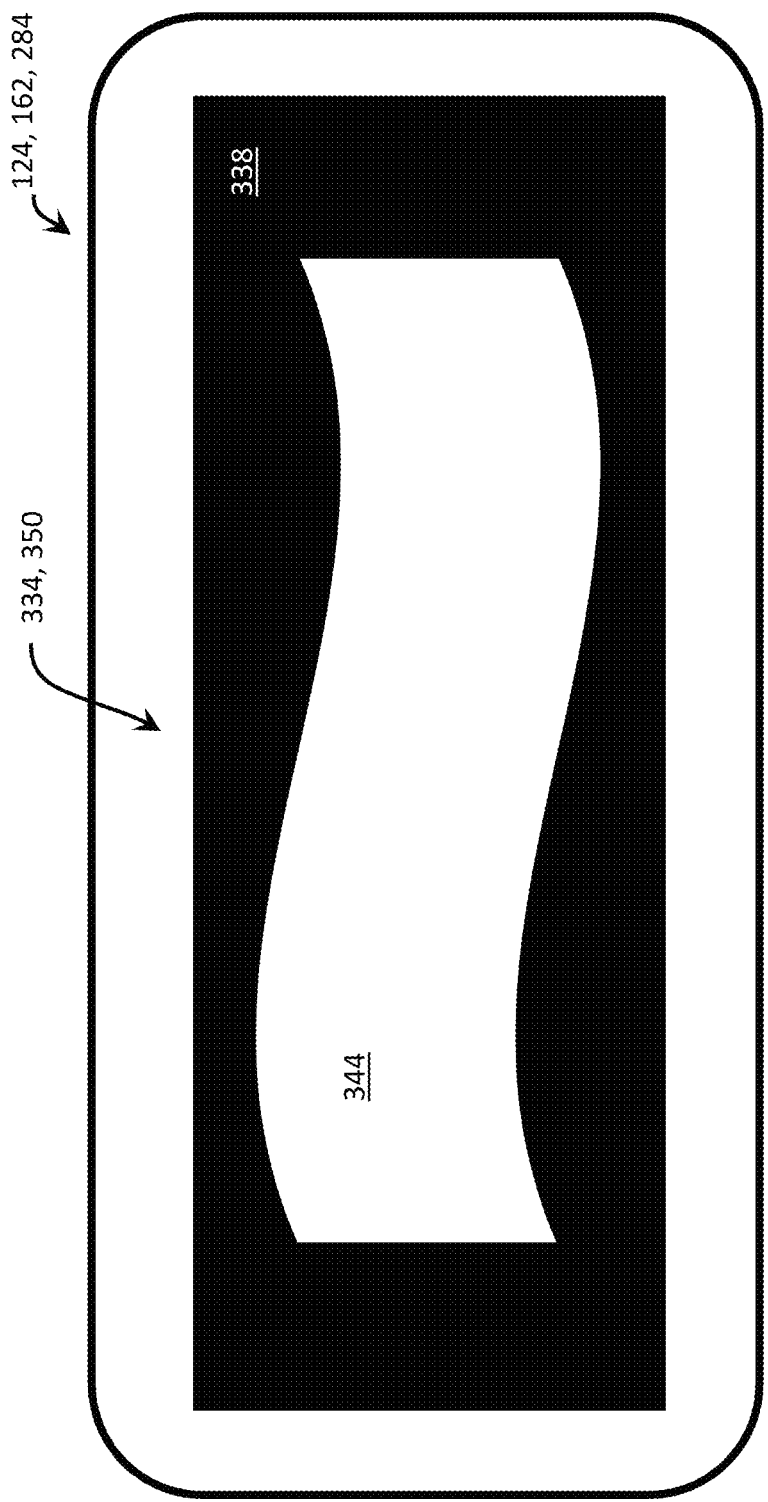
FIG. 52 is a rear view of the 3D medical headset of FIG. 32, illustrating the third frame of the example of the luminosity graphic of FIG. 50.

For a pupillary function test, listed in Table 1 below, the medical assembly 110 generates a luminosity graphic 334, as illustrated in FIGS. 50-52. The luminosity graphic 334 includes a background image 338 and a plurality of brightness stimuli 340, 342, 344. In this example, the luminosity graphic 334 includes a video having a plurality of images or frames 346, 348, 350 corresponding to the brightness stimuli 340, 342, 344, respectively. The brightness stimulus 344 is brighter than the brightness stimulus 342, and the brightness stimulus 342 is brighter than the brightness stimuli 340, 342, 344. The medical assembly 110 plays or generates the brightness stimuli 340, 342, 344 in a series or sequence of increasing brightness or decreasing brightness. By displaying occlusion images 330, as described above, the medical assembly 110 is also operable to display the brightness stimuli 340, 342, 344 solely to one eye at a time.

Figure 53:
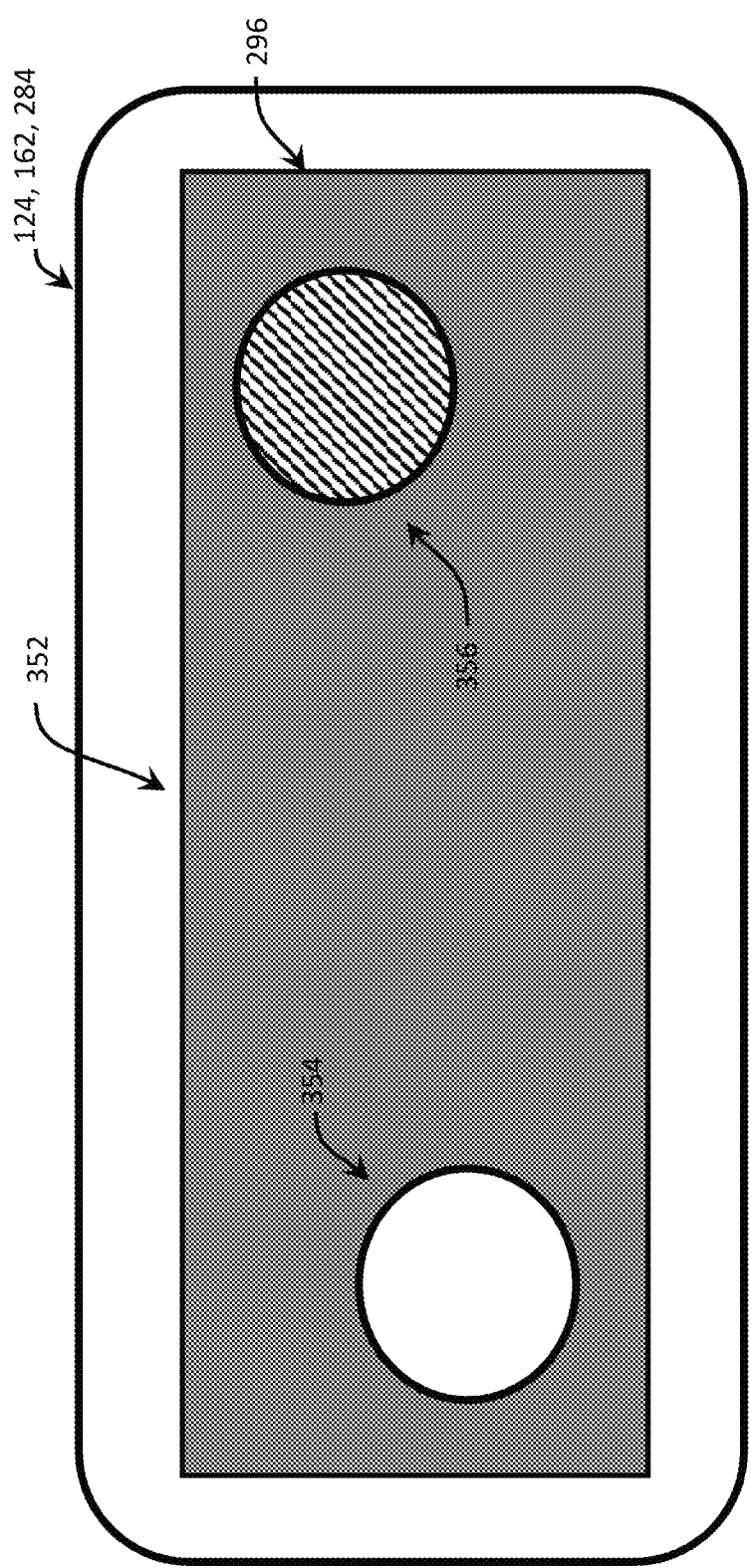
FIG. 53 is a rear view of the 3D medical headset of FIG. 32, illustrating an example of an interactive graphic.

For a dissociating test, listed in Table 1 below, the medical assembly 110 generates an interactive graphic 352, as illustrated in FIG. 53. The interactive graphic 352 includes the background image 296 and a plurality of moveable graphical elements 354, 356. The graphical elements 354, 356 can be differently colored, such as a red dot for the right eye 161 and a white dot for the left eye 163. The medical assembly 110 is operable to receive repositioning inputs from an accessory 255 (e.g., a handheld controller) operated by the subject 112. In this way, the subject 112 can select and drag, pull or slide one or each of the graphical elements 354, 356. In doing so, the subject 112 can cause (or attempt to cause) the graphical elements 354, 356 to overlap. For this example, the medical assembly 110 or health care provider audibly or visually prompts the subject 112 to use such accessory 255 to overlap the graphical elements 354, 356.

Figure 54:
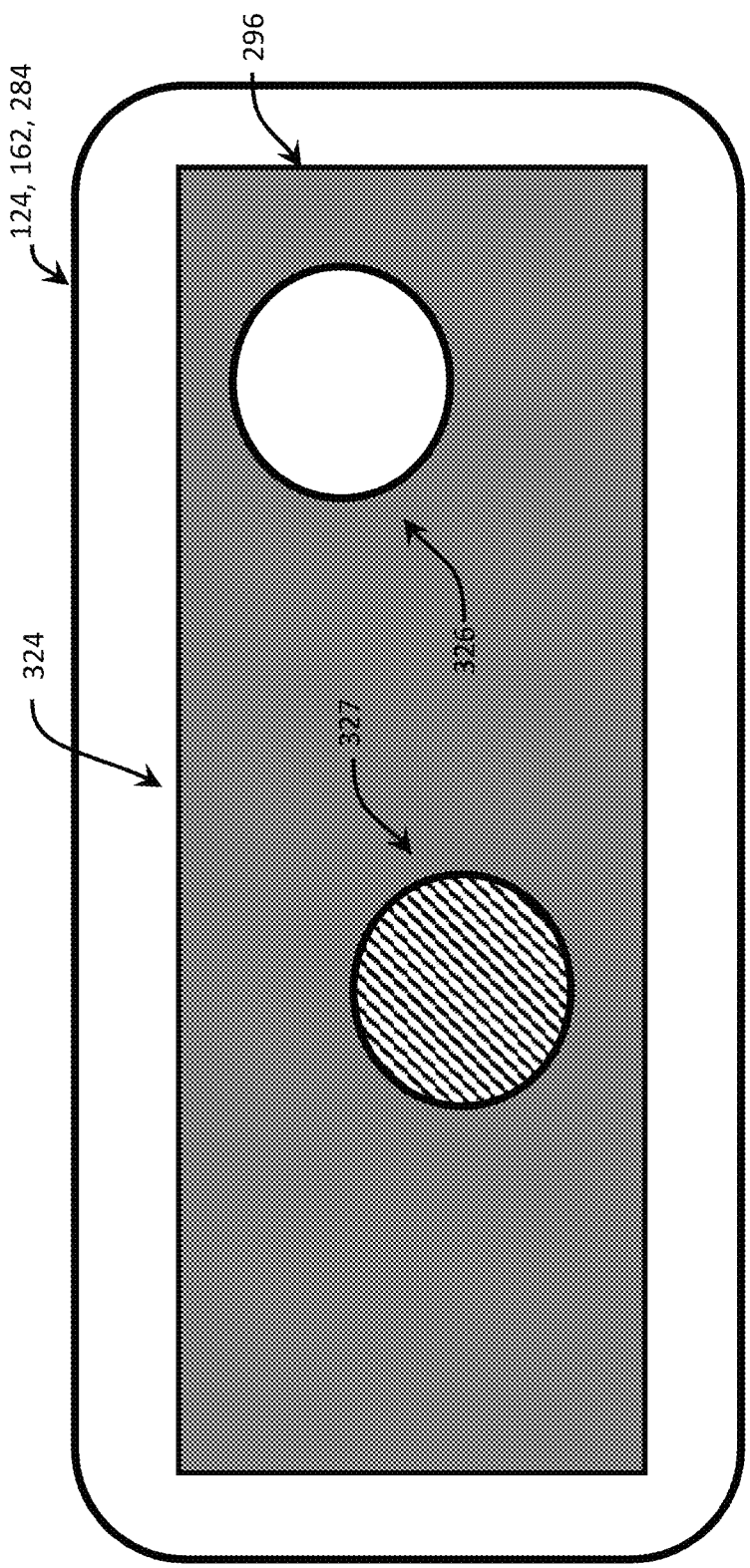
FIG. 54 is a rear view of the 3D medical headset of FIG. 32, illustrating an example of a gaze graphic.

For an inner-ear and vestibulo-ocular functions test, listed in Table 1 below, the medical assembly 110 generates the gaze graphic 324 illustrated in FIG. 54. As an analysis for correction saccades, correction nystagmus or vertigo, the medical assembly 110 or health care provider audibly or visually prompts the subject 112 to move the subject's head 160 while staring at, gazing at or fixating on one of the gaze targets 326, 327 for a designated period of time. Such head movements can include yaw rotation 278, pitch rotation 280, roll rotation 282, any combination thereof, or any specialized maneuvers associated with any symptoms, including head-thrust movement, dix-hallpike maneuver, log-rolling test, head shaking and caloric movement. Furthermore, as part of the inner-ear and vestibulo-ocular functions test, the health care provider can manually shake or move the head 160 horizontally, vertically or a combination thereof at a designated frequency. For example, the health care provider can horizontally move the head 160 at a frequency of two hertz for about fifteen cycles.

For an external eye appearance test, listed in Table 1 below, the medical assembly 110 photographs the external aspects of the subject's eyes 161, 163, resulting in a plurality of eye images. The images display the shapes, size and locations of the eyelids, eyebrows and other parts of the eyes 161, 163. The medical assembly 110 analyzes such images and determines eye dimensions and parameters.

Figure 55:
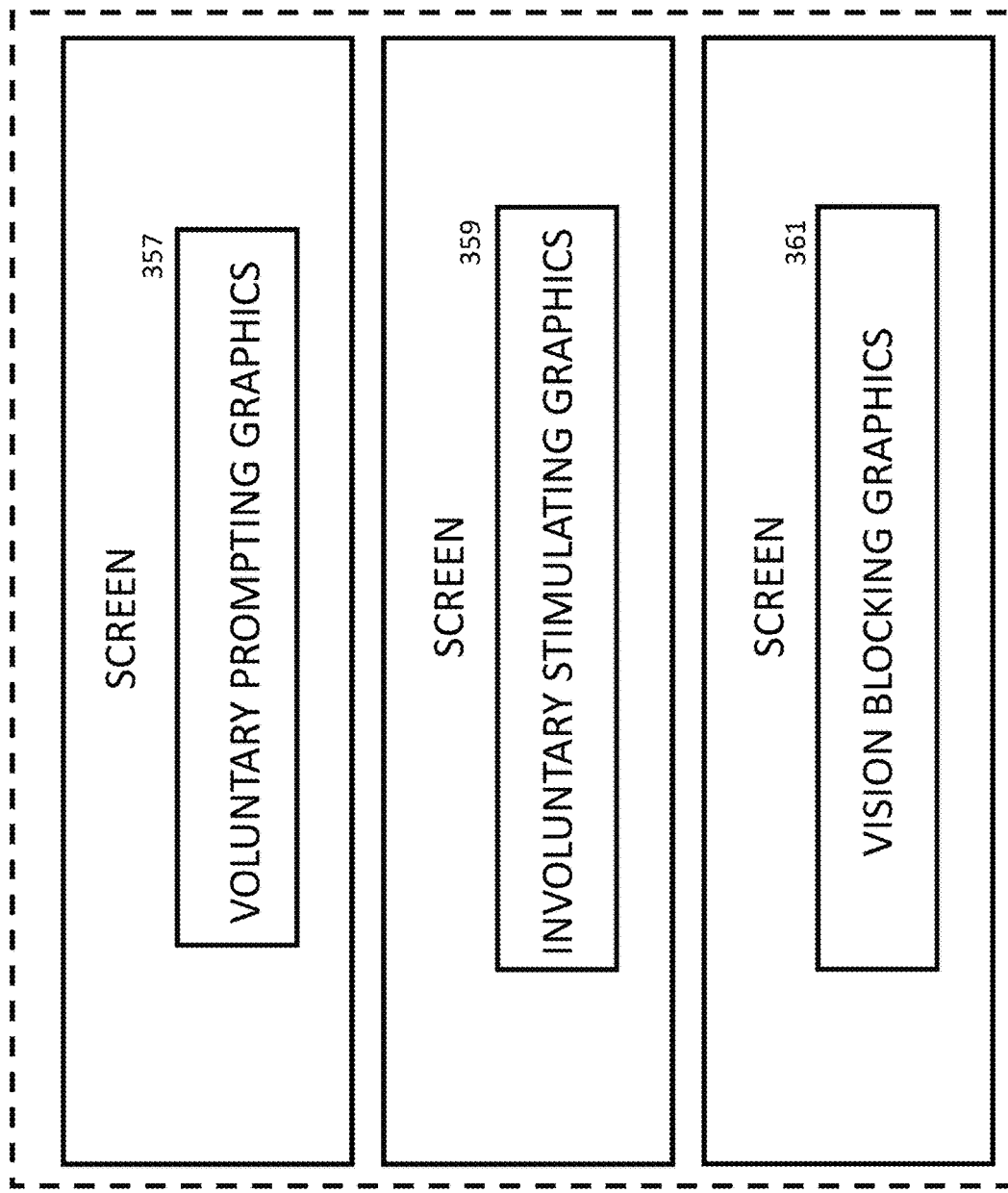
FIG. 55 is a schematic diagram illustrating embodiments of different types of graphics that can be generated by the medical assembly of FIG. 1.

As shown in FIG. 55, during the tests described above or other tests conducted through operation of the medical assembly 110, the medical assembly 110 generates various types of voluntary prompting graphics 357, involuntary stimulating graphics 359 and vision blocking graphics 361. The voluntary stimulating graphics 357 are configured to prompt voluntary reactions or voluntary responses from the subject 112. The involuntary stimulating graphics 359 are configured to prompt involuntary reactions or involuntary responses from the subject 112. The vision blocking graphics 361 are configured to block or cover a single eye of the subject 112 while the other eye remains uncovered.

10. Collection and Analysis of Sensed Parameters

Figure 56:
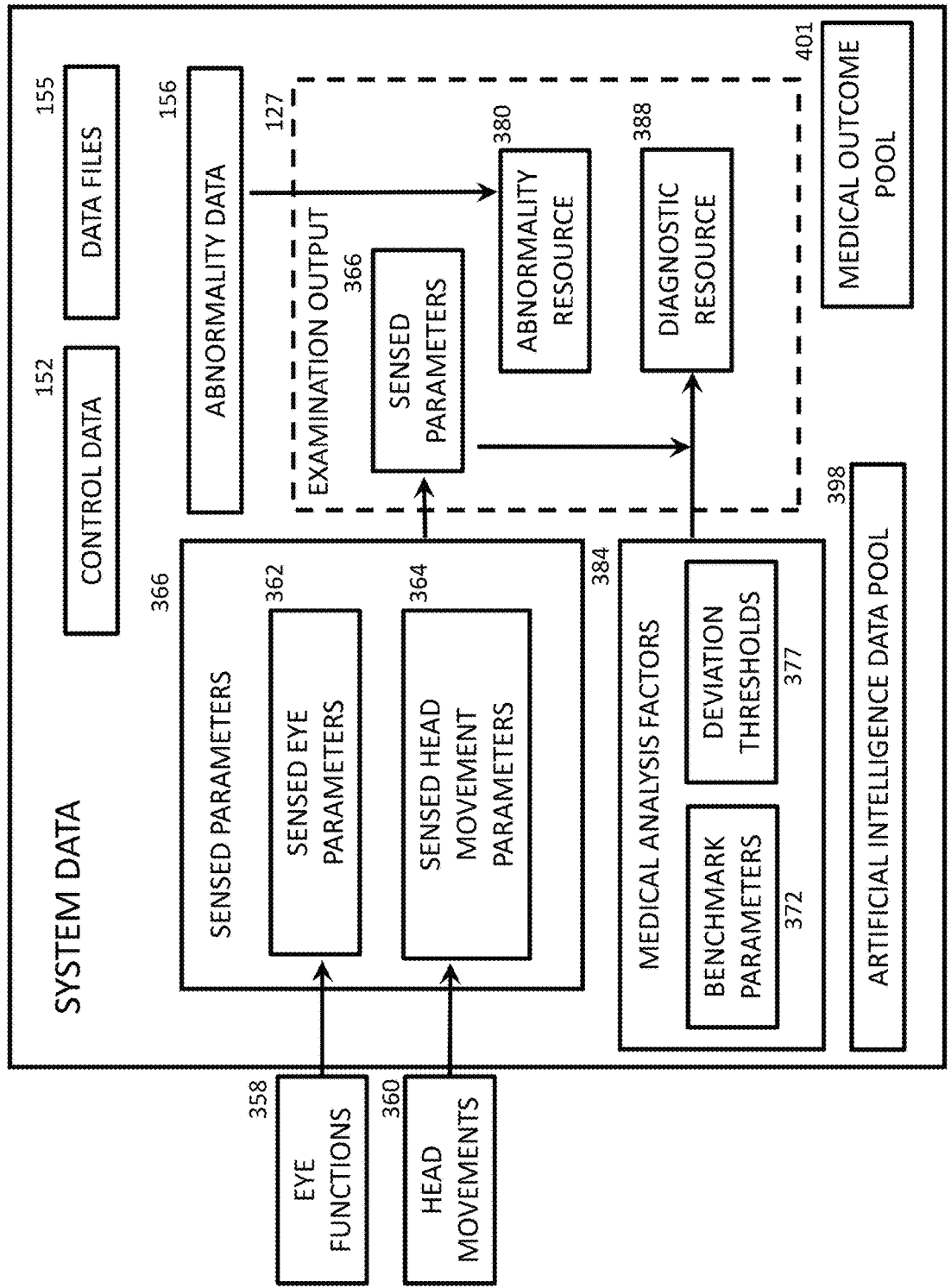
FIG. 56 is a schematic diagram illustrating an embodiment of the system data, including the different relationships between the different types of data.

Referring to FIG. 56, during each of the eye tests described above, the medical assembly 110 detects or senses a plurality of eye functions 358 and a plurality of head movements 360 relative to the physical environment 253. The eye functions 358 can include voluntary eye functions, involuntary eye functions or a combination thereof. The eye functions 358 can include, but are not limited to, reactionary eye movement and other eye reactions, such as pupil resizing. The head movements 360 can include a plurality of different types of rotations relative to the physical environment 153, including yaw rotation 278, pitch rotation 280, roll rotation 282 or any combination thereof.

Referring back to FIG. 28, the medical assembly 110 collects, receives or generates a plurality of sensed eye parameters 362 related to the eye functions 358 and a plurality of sensed head movement parameters 364 related to the head movements 360. The sensed parameters 366 (which include the sensed eye parameters 362 and the sensed head movement parameters 364) can be quantified or qualified in terms of dimensions, including measurement, dimensional data, length, diameter, angular degree, rate or distance per time, frequency, binary data (e.g., 1 for yes or present and 0 for no or absent), numeric variable, and color.

With continued reference to FIG. 28, in an embodiment, the sensed eye parameters 362 include a plurality of sensed eye movement parameters 369. Each sensed eye movement parameter 369 specifies or is otherwise related to a physical movement of either one of the eyes 161, 163 (or any part thereof) relative to the head 160 or the physical environment 253. The sensed eye parameters 362 also include a plurality of sensed pupil size parameters 371. Each sensed pupil size parameter 371 specifies or is otherwise related to a change in the size of the pupil of either one of the eyes 161, 163.

In an embodiment, during any of the eye tests described above, the medical assembly 110 is operable to capture eye movement and head movement during the periods of the tests. In an embodiment, the sensors 172 sense the movement of the head 160 regardless of whether the head movement affects the graphics displayed by the medical assembly 110.

During the pursuit eye movements test, the medical assembly 110 is operable to receive or generate sensed parameters 366, including the initial eye position when the eyes 161, 163 are fixated at a target in the middle of the background image 296, symmetry of the eyes 161, 163 based on a comparison of the eyes 161, 163 to each other, a range of motion to all directions of each eye, a deviation between the path of eye movement and the path of a moving target displayed against the background image 296, the velocity of eye movement, any latency or delay in eye movement, and the visual field of each of the eyes 161, 163.

During the saccadic eye movements test, the medical assembly 110 is operable to receive or generate sensed parameters 366, including the initial eye position when the eyes 161, 163 are fixated at a target in the middle of the background image 296, any latency or delay in eye movement, amplitude of eye movement, velocity of eye movement, accuracy of the eyes' saccadic movements, and symmetry of the eyes 161, 163 based on a comparison of the eyes 161, 163 to each other.

During the vergence test, the medical assembly 110 is operable to receive or generate sensed parameters 366, including eye movement, head movement and pupillary resizing and changes.

During the spontaneous eye movements test, the medical assembly 110 is operable to receive or generate sensed parameters 366, including eye movement and head movement. The sensed parameters 366 related to eye movement can include, but are not limited to, frequency of eye movement, velocity of eye movement, amplitude of eye movement, and direction of eye movement.

During the phoria-tropia test, the medical assembly 110 is operable to receive or generate sensed parameters 366 relating to the functions and characteristics of the covered eye and the uncovered eye.

During the pupillary function test, the medical assembly 110 is operable to receive or generate sensed parameters 366, including response of the pupil to direct bright light and consensual pupillary reflex, including the response of the contralateral pupil to bright light when shined into the eyes 161, 163.

During the dissociating test, the medical assembly 110 is operable to receive or generate sensed parameters 366, including the movement and variable positions of the eyelids as well as the angle or direction of the line extending between the moveable graphical elements 354, 356 and the distance between the moveable graphical elements 354, 356.

During the inner-ear and vestibulo-ocular functions test, the medical assembly 110 is operable to receive or generate sensed parameters 366, including the direction and velocity of eye movements detected by the sensors 172 during any head movement, including loss of gaze fixation, correction saccades, nystagmus or a combination thereof.

The medical assembly 110 is also operable to perform a hearing test. In an embodiment, the medical assembly 110 causes the ear assemblies 170 to emit sounds of different volumes and pitches to one ear at a time. The subject 112 can interact with an accessory 255 (e.g., a handheld controller) to provide an input when the subject 112 hears each sound. The system logic 118 includes a suitable fourier transform module or logic. According to such system logic 118, the medical assembly 110 calculates, determines or otherwise generates a plurality of sensed parameters 366, including head and eye movements, which the medical assembly 110 uses to compute auditory gain and phase.

In an embodiment, the medical assembly 110 generates certain sensed eye parameters 362 by comparing a sensed eye parameter 362 of one eye to the sensed eye parameter 362 of the other eye. For example, the medical assembly 110 can compare the pupil diameters of the subject's right and left eyes 161, 163 and, based on that comparison, generate a size abnormality of the left eye 163. In this example, the dimension of such size abnormality would be one of the sensed eye parameter 362 of the left eye 163. Also, the medical assembly 110, processing the subject health history data 389 shown in FIG. 57, can compare the sensed pupil diameters to the pupil diameters of the subject 112 that were recorded in the past. Based on such comparison, the medical assembly 110 can generate or indicate pupil size abnormalities.

In an embodiment, the medical assembly 110 generates certain sensed eye parameters 362 based on or depending on one or more of the sensed head movement parameters 364. In this embodiment, the system logic 118 includes a head movement data compensator 367 as shown in FIG. 29. The head movement data compensator 367 directs the medical assembly 110 to calibrate, correct, offset, modify or adjust the eye parameter data received from the sensors 172 to generate certain sensed eye parameters 362. Based on the head movement data compensator 367, such sensed eye parameters 362 exclude or reduce eye inaccuracies or false eye information caused by head movement.

As described below, to collect certain types of sensed parameters 366, the medical assembly 110 captures and stores images. Depending on the embodiment and adjustable settings, the medical assembly 110 can repetitively photograph a sequence of images of the eyes 161, 163 or the head 160, or the medical assembly 110 can continuously record and generate a video of the action of the eyes 161, 163 or the head 160. In either case, the medical assembly 110 generates a series of images, whether derived from photographs or video frames, and each of these images is stored in the form of an image file 365, as shown in FIG. 27. The medical assembly 110 is configured to incorporate such image files 365 into the system data 125. After stored, the medical assembly 110 is configured to analyze such images and, based on such analysis, generate one or more sensed parameters 366 associated with each one of such images.

Figure 57:
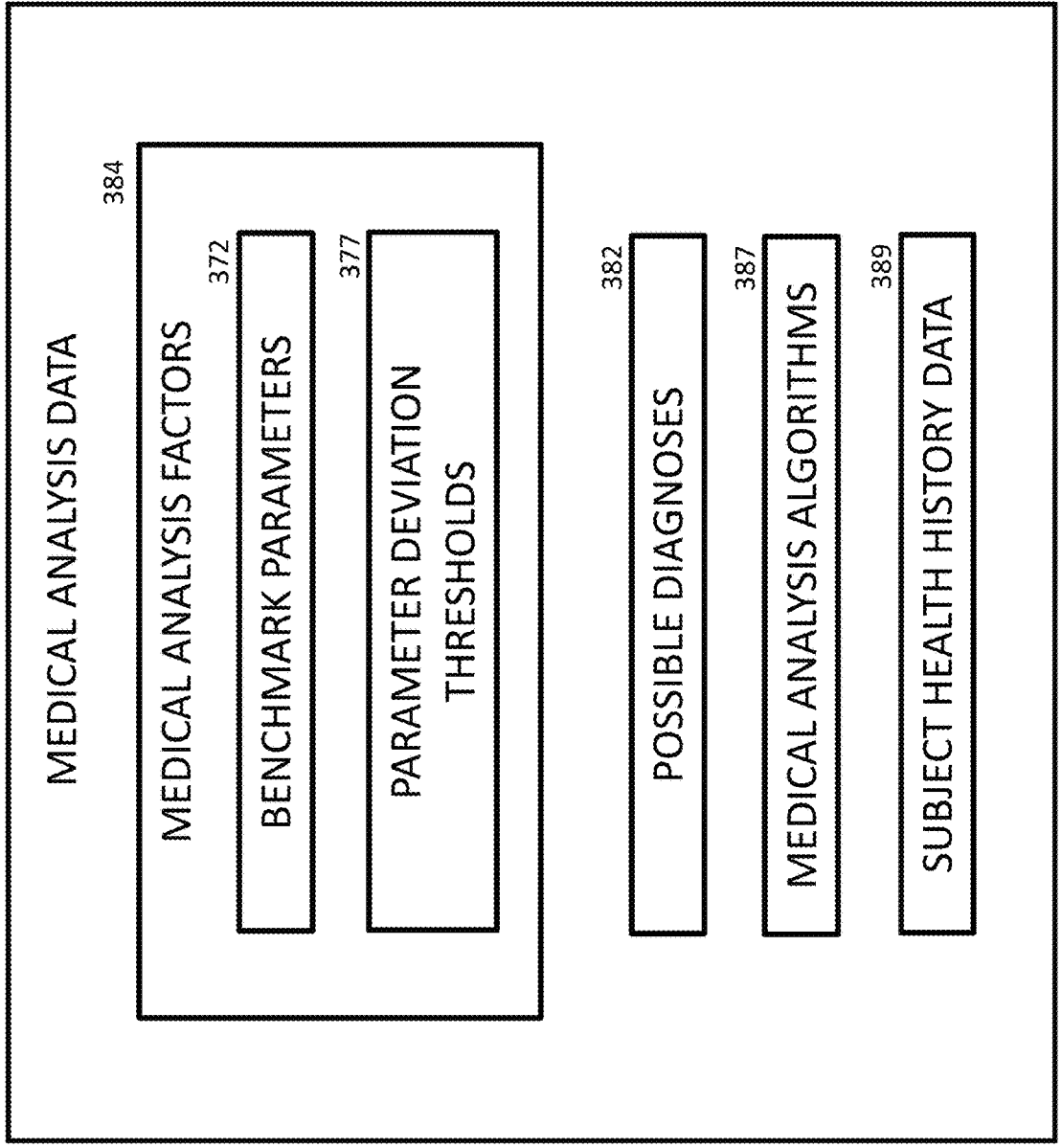
FIG. 57 is a schematic diagram illustrating an embodiment of medical analysis data that can be processed by the medical assembly of FIG. 1.

As described above, the medical assembly 110 determines and processes a plurality of sensed parameters 366, including the sensed eye parameters 362 and the sensed head movement parameters 364. The sensed parameters 366 are received or generated based, at least in part, on the electronic measuring, monitoring or observing by the sensors 172. As shown in FIG. 57, the sensed parameters 366 are associated with a plurality of eye characteristic categories 368. The following table provides a list certain eye tests described above, examples of the eye characteristic categories 368 associated with each such eye test, and examples of sensed parameters 366 based on such tests:

TABLE 1

| Test Name | Eye Characteristic Category(ies) | Example of Sensed Parameter(s) |
|---|---|---|
| Pursuit Eye Movements | Adduction | 48 degrees |
| | Abduction | 46 degrees |
| | Elevation | 34 degrees |
| | Depression | 58 degrees |
| Saccadic Eye Movements | Saccade Latency | 400 milliseconds |
| | Saccade Velocity | 657 degrees per second |
| | Saccade Accuracy | −3 degrees per 20 degrees |
| Vergence | Vergence | 30 degrees |
| | Pupil Size | 3.5 millimeters |
| Spontaneous Eye Movements | Frequency of spontaneous eye movements | 2 hertz |
| | Velocity of Slow Component | 30 degrees per second |
| | Velocity of Fast Component | 100 degrees per second |

TABLE 1-continued

| Test Name | Eye Characteristic Category(ies) | Example of Sensed Parameter(s) |
|---|---|---|
| | Amplitude | 20 degrees |
| | Direction | Horizontal |
| Phoria-Tropia | Phoria | Exodeviation of 10 degrees |
| | Tropias | Exodeviation of 20 degrees |
| Pupillary Function | Pupillary Diameter in Light | 4 millimeters |
| | Pupillary Diameter in Dark | 5 millimeters |
| | Time for Pupillary Size Change | 1 millisecond |
| Dissociating Inner-Ear and Vestibulo-Ocular Functions | Magnitude of Diplopia | 15 degrees of exotropia |
| | Loss of Gaze Fixation (Yes: 1/No: 0) | 1 |
| | Correction Saccades (Yes: 1/No: 0) | 0 |
| | Nystagmus (Yes: 1/No: 0) | 1 |
| | Nystagmus Direction (Vertical: 1/Horizontal: 2) | 1 |
| | Vestibular Gain | 0.70 |
| External Eye Appearance | Palpebral Fissure Opening | 10 millimeters |

As shown in FIG. 58, each eye characteristic category 368 is associated with: (a) at least one of a plurality of eye abnormalities 370; (b) at least one of a plurality of benchmark parameters 372; (c) at least one of the sensed parameters 366; (d) a percentile severity indicator 374 representing the value of the relevant sensed parameter 366 that is below or above the other values in a designated population; (e) a deviation 376 of the sensed parameter 366 compared to the associated benchmark parameter 372; and (f) a severity ranking, severity score or severity indicator 378 depending, at least in part, on the associated deviation 376.

The severity indicator 378 indicates a level of severity of an eye abnormality 370 relative to a plurality of levels of severity associated with the type of such eye abnormality 370. The severity indicator 378 can also be based on one or more medical analysis factors 384, which are described below. In an embodiment, each of the eye abnormalities 370 is associated with a weight factor based on the percentile severity indicator 374 or based on the severity indicator 378 corresponding to such eye abnormality 370.

Referring back to FIG. 56, the value of the percentile severity indicator 374 (e.g., 60$^{th}$ percentile) or the value of the severity indicator 378 (e.g., 3) is fed into the abnormality data 156 which, in turn, is fed into the abnormality resource 380. The percentile severity indicator 374 or the severity indicator 378 automatically provides the heath care provider with an estimate of the severity of the relevant eye abnormality.

With continued reference to FIGS. 56-57, the medical analysis data 158 includes a plurality of medical analysis factors 384, which, in turn, include the benchmark parameters 372. The benchmark parameters 372 are pre-stored and derived from one or more medical sources of health, clinical or diagnostic information. The medical analysis data 158 also includes a list of possible diagnoses 382.

Referring to FIGS. 58-59, for each possible diagnosis 382, the medical analysis data 158 includes one or more medical analysis factors 384 that correlate to such diagnosis 382. The medical analysis factors 384 include, are based on, or depend on: (a) one or more of the deviations 376 of the relevant eye abnormalities 370; and (b) one or more parameter deviation thresholds 377. Each parameter deviation threshold 377 specifies a designated level or magnitude that is usable as a comparison to the associated deviation 376. For each possible diagnosis 382, the medical analysis factors 384 are storable in the form of a diagnostic file or medical analysis file 379, as shown in FIG. 27.

Furthermore, the medical analysis data 158 includes a diagnostic certainty ranking, diagnostic certainty score or diagnostic certainty indicator 386, as shown in FIG. 59. The diagnostic certainty indicator 386 depends on a plurality of variables, including the magnitudes of the relevant deviations 376. The diagnostic certainty indicator 386 provides the heath care provider with an estimate of the likelihood that the subject 112 actually has the disorder corresponding to such diagnostic certainty indicator 386.

With continued reference to FIG. 59, in an embodiment, the medical assembly 110 generates a diagnostic resource 388 in addition to the abnormality resource 380. The diagnostic resource 388 includes a plurality of possible diagnoses 382 indicative of a plurality of disorders, each of which is associated with one or more of the eye characteristic categories 368. The diagnostic resource 388 includes a diagnostic certainty indicator 386 that is at least partially based on one or more of the deviations 376. The diagnostic certainty indicator 386 includes diagnostic certainty information. Such certainty information can include a probability factor (such as a percentage) associated with one of the diagnoses 382. Such probability factor represents an estimate of the probability that a diagnosis 382 of a disorder is correct or otherwise appropriate in accordance with the applicable standard of care.

In an embodiment, the medical analysis factors 384 include a plurality of medical analysis algorithms 387, as shown in FIG. 57. The medical analysis algorithms 387 can include a plurality of protocols, procedures, ANNs, neural networks or decision trees structured or otherwise arranged for diagnostic or medical analysis purposes. The medical analysis algorithms 387 are codified in the form of computer-readable instructions stored in the system logic 118 for execution by the programmed processor 151 of the medical assembly 110.

Each medical analysis algorithm 387 is associated with a designated one of the eye abnormalities 370 or a designated disorder. Each medical analysis algorithm 387 includes or specifies a plurality of different types of events and one or more decision flows or directives stemming from each such event. The events and directives can be interrelated and dependent upon each other. Eventually, one or more of the directives leads to a result. Depending on the type of the medical analysis algorithm 387, the result can include an identification of: (a) one or more actual or possible abnormalities 370; (b) one or more possible diagnoses 382 of one or more disorders; or (c) a combination thereof.

Figure 60:
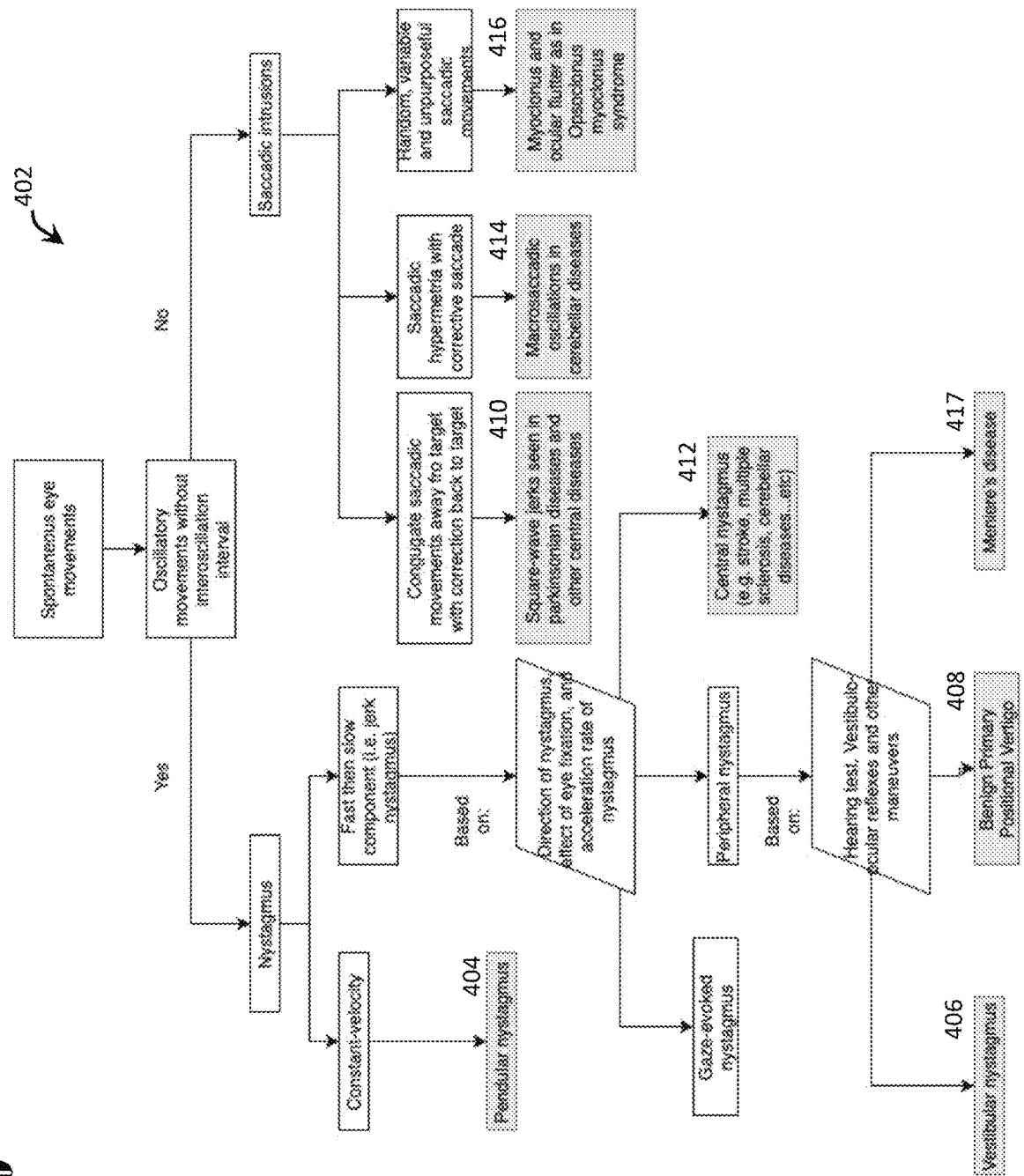
FIG. 60 is a flow chart representing an example of a medical analysis algorithm.

In the example shown in FIG. 60, the medical analysis algorithm 402 is structured to evaluate for the following eye abnormalities: pendular nystagmus 404, vestibular nystagmus 406, benign primary positional vertigo 408, square-wave jerks 410 seen in parkinsonian diseases and other central diseases, central nystagmus 412 seen in stroke, multiple sclerosis and cerebellar diseases, macrosaccadic oscillations 414 seen in cerebellar diseases, myocionus and ocular flutter 416 seen in Opsocionus myoclonus syndrome, and Miniere's disease 417. Such eye abnormalities can be identified or revealed through the spontaneous eye movements test described above and other tests described above.

Figure 61:
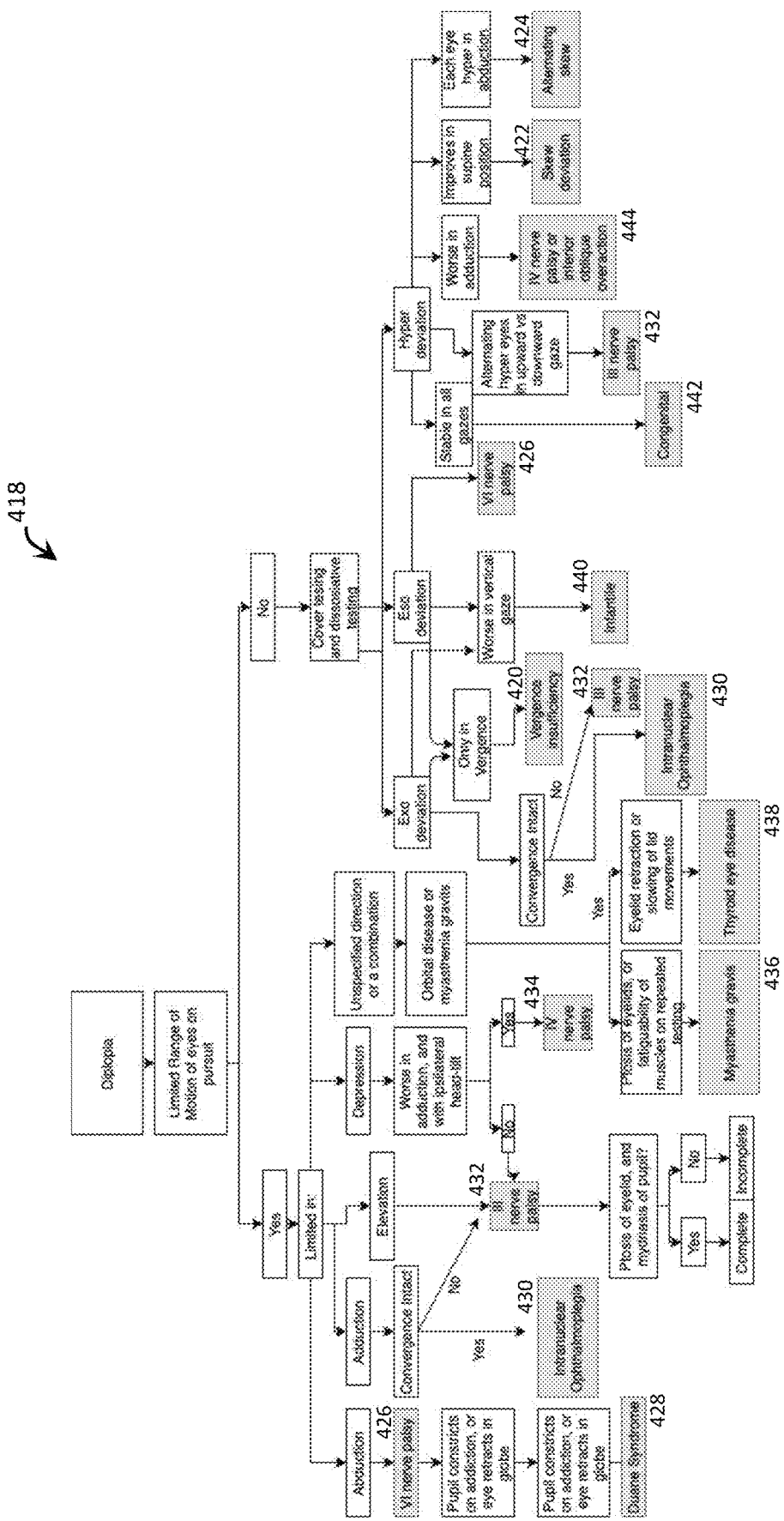
FIG. 61 is a flow chart representing an example of another medical analysis algorithm.

In the example shown in FIG. 61, the medical analysis algorithm 418 is structured to: (a) evaluate for the following eye abnormalities: vergence insufficiency 420, skew deviation abnormality 422 and alternating skew abnormality 424; and (b) evaluate for the following disorders: VI nerve palsy 426, Duane Syndrome 428, intranuclear ophthalmoplegia 430, III nerve palsy 432, IV nerve palsy 434, Myasthenia gravis 436, thyroid eye disease 438, infantile 440, congenital 442, or IV nerve palsy or inferior oblique overaction 444. Such abnormalities and disorders can be identified or revealed through the pursuit eye movements test described above and other tests described above.

In another embodiment, the medical analysis data 158 includes subject health history data 389 as shown in FIG. 57. The subject health history data 389 includes historical clinical and health data related to the history of the particular subject 112 who has undergone the eye examination, including patient-specific historical data files. By processing the subject health history data 389, the medical assembly 110 can compare the sensed parameter 366 of any eye characteristic category or any other health category with the historical parameter related to the same category. Based on such comparison, the medical assembly 110 can generate or indicate one or more abnormalities. Also, the medical assembly 110 can process the subject health history data 389 to monitor any particular subject's progression of any identified abnormality.

When a health care provider or user provides the medical assembly 110 with a request for a report or output related to an eye examination, the medical assembly 110 is operable to automatically generate the examination output 127. As shown in FIG. 56, the examination output 127 includes, among other examination results and information: (a) the sensed parameters 366 related to such examination; and (b) the abnormality resource 380 related to such examination, the diagnostic resource 388 related to such examination, or a combination of the abnormality resource 380 and the diagnostic resource 388. The examination output 127 provides health care providers with important and valuable assistance with diagnosing disorders for subjects 112. The medical system 114 and the system data 125 enable the medical assembly 110 to automatically generate the examination output 127. This process involves a systematized analysis based on the electronically-sensed parameters 366, benchmark parameters 372, and numerous medical analysis factors 384 and combinations thereof. This systematized process provides a substantial improvement over conventional steps manually performed by health care providers, which can lead to risks of misdiagnoses and diagnostic omissions. The systematized process implemented by the medical assembly 110 decreases such risks, resulting in improved health care performed at a faster rate with the convenience of being performed remotely or in-person at a health care facility.

In an embodiment, the examination output 127 includes an eye examination report, such as the eye motility report 390 exemplified in FIGS. 62-64. As shown in FIGS. 61-64, the eye motility report 390 provides sensed parameters 366 related to ductions, the pupils, maneuver testing and external eye appearance. As shown in FIG. 64, the eye motility report 390 also provides an abnormality resource 446 and a diagnostic resource 448. The abnormality resource 446 identifies three eye abnormalities numbered one through three. For each such eye abnormality, the abnormality resource 446 displays one of the severity indicators 450, 452, 454 related to such eye abnormality. The diagnostic resource 448 identifies three possible diagnoses numbered one through three. For each such diagnosis, the diagnostic resource 448 displays one of the certainty indicators 456, 458, 460, each of which is a diagnostic certainty percentage.

Figure 66:
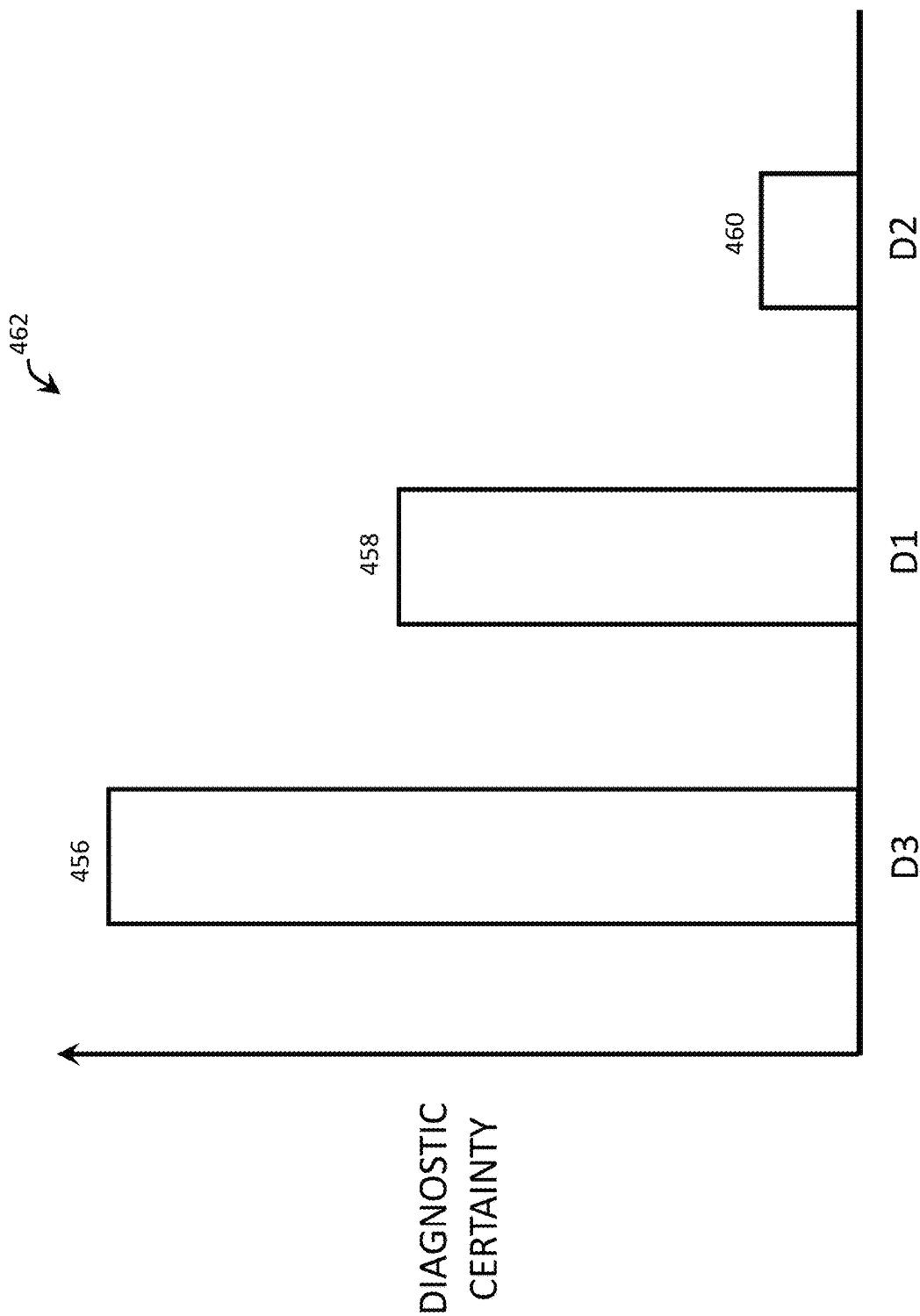
FIG. 66 is an example of a certainty bar chart displaying a plurality of different certainty indicators, each of which is associated with a possible diagnosis.

The examination output 127, such as the eye motility report 390, can exhibit or convey the diagnostic certainty or certainty indicators 386 using various types of certainty indicators 386, as shown in FIG. 65. Depending on the embodiment, the certainty indicators 392 for different diagnoses can include different percentages, or a scale 394 of different textual descriptions, different symbols or different colors. In another embodiment shown in FIG. 66, the certainty indicators 456, 458, 460 for different diagnoses can be incorporated into a chart, such as the certainty bar chart 462.

In another embodiment, the medical assembly 110 is operable in accordance with a method having the following steps:

In a first step, the subject 112 mounts the 3D medical headset 284 to the head 160 of the subject 112.

In a second step, the 3D medical headset 284 is activated to begin generating visual or audible instructions to the eyes of the subject 112.

In a third step, the 3D medical headset 284 displays a sentence that states "Follow the dot with your eyes." Alternatively, the 3D medical headset 284 can audibly generate this instruction by outputting an audible output played to the subject 112 via the ear assemblies 170.

In a fourth step, the 3D medical headset 284 activates the sensors 172 to start collecting sensed parameters 366, including the position of the pupils, pupil diameter, openness of the eyes by measuring the distance between the eyelids, and head orientation.

In a fifth step, the 3D medical headset 284 displays various types of voluntary prompting graphics 357, involuntary stimulating graphics 359 and vision blocking graphics 361, as described above. The particular type of graphic that is presented depends on the type of eye test being conducted.

In a sixth step, the medical assembly 110 collects or otherwise receives the sensed parameters 366 (including the sensed eye parameters 362 and sensed head movement parameters 364) collected or generated by the sensors 172. In an embodiment, each of the sensed parameters 366 has a value, including a numerical value (e.g., 2 millimeters) or a binary value (e.g., 0 representing no or not present and 1 representing yes or present). In performing this sixth step, the medical assembly 110 records or stores the time at which each of the sensed parameters 366 was collected. Based on the stored time, the medical assembly 110 stores a timestamp value in association with each of the sensed parameters 366. In an embodiment, the timestamp values are unique points on a chronological timeline. The interval of the timestamp values depends on the frequency of the sensing activity of the 3D medical headset 284. For example, the medical assembly 110 may sense the duction of the eyes for a designated eye test over a timeline having timestamps at increments of milliseconds. The test may begin at timestamp zero, and the duction of the subject 112 may continue for a duration of nine hundred milliseconds or timestamps. At each millisecond mark or timestamp, the medical assembly 110 is operable to capture and store a photograph or image of each eye 161, 163 of the subject 112, resulting in eighteen hundred eye images, eighteen hundred corresponding image files 365, and eighteen hundred corresponding timestamp values. As described below, in an embodiment, the timestamp values are incorporated into time series files 403 of the data files 155, as shown in FIG. 27, and the medical assembly 110 uses and processes such timestamp values for purposes of generating the examination output 127.

In a seventh step, the medical assembly 110 de-noises the sensed parameters 366 (including sensed parameters 366 related to eye blinks) by applying one or more signal processing filters to the sensed parameters 366. The signal processing filters are stored within or operatively coupled to the medical system 114. The signal processing filter can include artificial, normal values and any suitable data filtering or data screening algorithm, computer program, software, or software-based service, including the Savitzky-Golay filter algorithm. All of the specifications of such algorithm are hereby incorporated by reference into this disclosure. The de-noising parameters of the signal processing filter depends on the data quality of the sensed parameters 366.

In an eighth step, the medical assembly 110 maps the sensed head movement parameters 364 to the sensed eye parameters 362. As part of this mapping process, the medical assembly 110 records or stores each set of sensed head movement parameters 364 that is related to each set of sensed eye parameters 362.

In a ninth step, after having de-noised and mapped the sensed parameters 366, the medical assembly 110 analyzes the sensed parameters 366. In one embodiment for the ninth step, the medical assembly 110 stores or has access to a plurality of the eye characteristic categories 368 described above. Each of the eye characteristic categories 368 is associated with at least one of the sensed parameters 366 and at least one of the benchmark parameters 372. In the analysis, the medical assembly 110 compares the sensed parameter 366 to the benchmark parameter 372, determines the deviation 376 of the sensed parameter 366 relative to the benchmark parameter 372, compares the deviation 376 to a parameter deviation threshold 377, processes a plurality of medical analysis factors 384, and outputs an examination output 127, which includes a diagnostic resource 388. The diagnostic resource 388 identifies one or more possible diagnoses 382 of one or more disorders.

For another embodiment for the ninth step, the system logic 118 includes an artificial intelligence (AI) module 396, which includes one or more AI or machine learning algorithms. The system data 125 includes an AI data pool 398 and a medical outcome pool 401 as shown in FIG. 56. In this embodiment, the AI data pool 398 is operatively coupled to a plurality of units of 3D medical headsets 284 used by a plurality of different subjects. Each time the medical assembly 110 identifies any possible diagnoses 382 based on the 3D medical headsets 284, the medical assembly 110 stores the sensed parameters 366 and associated possible diagnoses 382 in the AI data pool 398. The medical outcome pool 401 is configured to store, for each subject 112, the actual, clinical diagnoses completed by the health care provider with respect to the sensed parameters 366 and any other health considerations. By executing the AI module 396, shown in FIG. 29, the medical assembly 110 automatically searches within the system data 125 to determine, identify or recognize data patterns. Each such pattern is associated with one or more of the possible diagnoses 382, shown in FIG. 58, or one or more of the actual, clinical diagnoses described above. The medical assembly 110 is configured to generate a diagnostic resources 388 (including possible diagnoses 382) depending on the recognized patterns. The medical assembly 110 outputs an examination output 127, which includes such diagnostic resource 388 that identifies one or more possible diagnoses 382 of one or more disorders.

The diagnostic accuracy of the medical assembly 110 gradually improves based on increases in the amount of data in the AI data pool 398 and medical outcome pool 401. It should be appreciated that the medical assembly 110 can generate such patterns without relying on actual, clinical diagnoses or data from the medical outcome pool 401. For example, the AI module 396 can be configured to self-improve or auto-improve the diagnostic accuracy of the medical assembly 110 by analyzing and processing the data in the AI data pool 398. Depending on the embodiment, the AI module 396 can include or be operatively coupled to a trained, artificial neural network (ANN) or a statistical model, such as a linear regression model. It should be appreciated that ANNs can include a combination of data and AI software, including artificial neurons or logical functions, connections and propagation functions.

In a tenth step, the medical assembly 110 displays the examination output 127 (including the generated list of possible diagnoses 382) on the display unit 198 of the 3D medical headset 284 or on the monitor 126. Also, the medical assembly 110 enables users to email and print the examination output 127.

As described above, in an embodiment, the medical assembly 110 processes the parameter deviation thresholds 377 to automatically produce an examination output 127. In such embodiment, the parameter deviation thresholds 377 are stored in diagnostic files or medical analysis files 379. To enable the medical assembly 110 to assess a possible diagnoses 382 for a particular disorder not previously handled by the medical assembly 110, a user can prepare or obtain a diagnostic file or medical analysis file 379 that contains medical analysis factors 384 and the parameter deviation threshold 377 related to such disorder. The user can then input such medical analysis file 379 into the secondary data storage device 122.

11. Artificial Intelligence

As described above, in an embodiment, the medical assembly 110 stores a timestamp value in association with each of the sensed parameters 366. In an embodiment, the medical assembly 110 captures or arranges the timestamp values in the form of time series data. The time series data, storable in time series files 403, is associated with all or a plurality of the eye and head images captured by the sensors 172. The process of generating and processing of such time series data can be relatively complex, causing the medical assembly 110 to undergo relatively high demands for processing power and power consumption. In an embodiment, the AI module 396 includes machine learning algorithms, such as deep learning algorithms, to efficiently and accurately analyze such time series data. Such analysis includes data classification, data clustering, data anomaly detection, or any suitable combination of such tasks. This provides an improvement to computer functionality, which provides the medical assembly 110 with improved efficiency, accuracy, speed and performance, as well as a decreased need for the consumption of processing power.

Such time series data poses a multiple input, multiple output problem or challenge. Consequently, traditional feed forward ANNs can fall short of accurately analyzing time series data. To overcome or lessen the effects of such shortcoming, the AI module 396, in an embodiment, has one or more recurrent neural networks (RNNs). RNNs are ANNs having special units, such as gated recurrent units (GRUs) or long short term memory units (LSTMs). These kinds of units help the medical assembly 110 learn information from a current or present time data point in addition to all the previous time data points. In another embodiment, the AI module 396 has one or more bi-directional RNNs, which learn from previous and future time data points. In yet another embodiment, the AI module 396 has one or more convolutional neural networks (CNNs) for analyzing the time series data. CNNs, a type of ANN, are operable or executable to train deep ANNs to learn about images. CNNs have a relatively high effectiveness for grouping data points together to form or recognize data patterns associated with disorders. CNNs, used together with RNNs like LSTMs, have a relatively high effectiveness for analyzing time series data. LSTMs and CNNs are connected together in a hybrid neural network to process and analyze sensed parameters 366 that include a plurality of different angular pupil positions. Such hybrid neural network also processes and analyzes the time series data associated with the image capturing of such pupil positions.

Depending on the embodiment, the medical assembly 110 applies or executes various kinds of machine learning algorithms to identify or recognize data patterns derived from the sensed parameters 366 to produce examination outputs 127. Such examination outputs 127 can include abnormality resources 380 and diagnostic resources 388, as described above.

Figure 67:
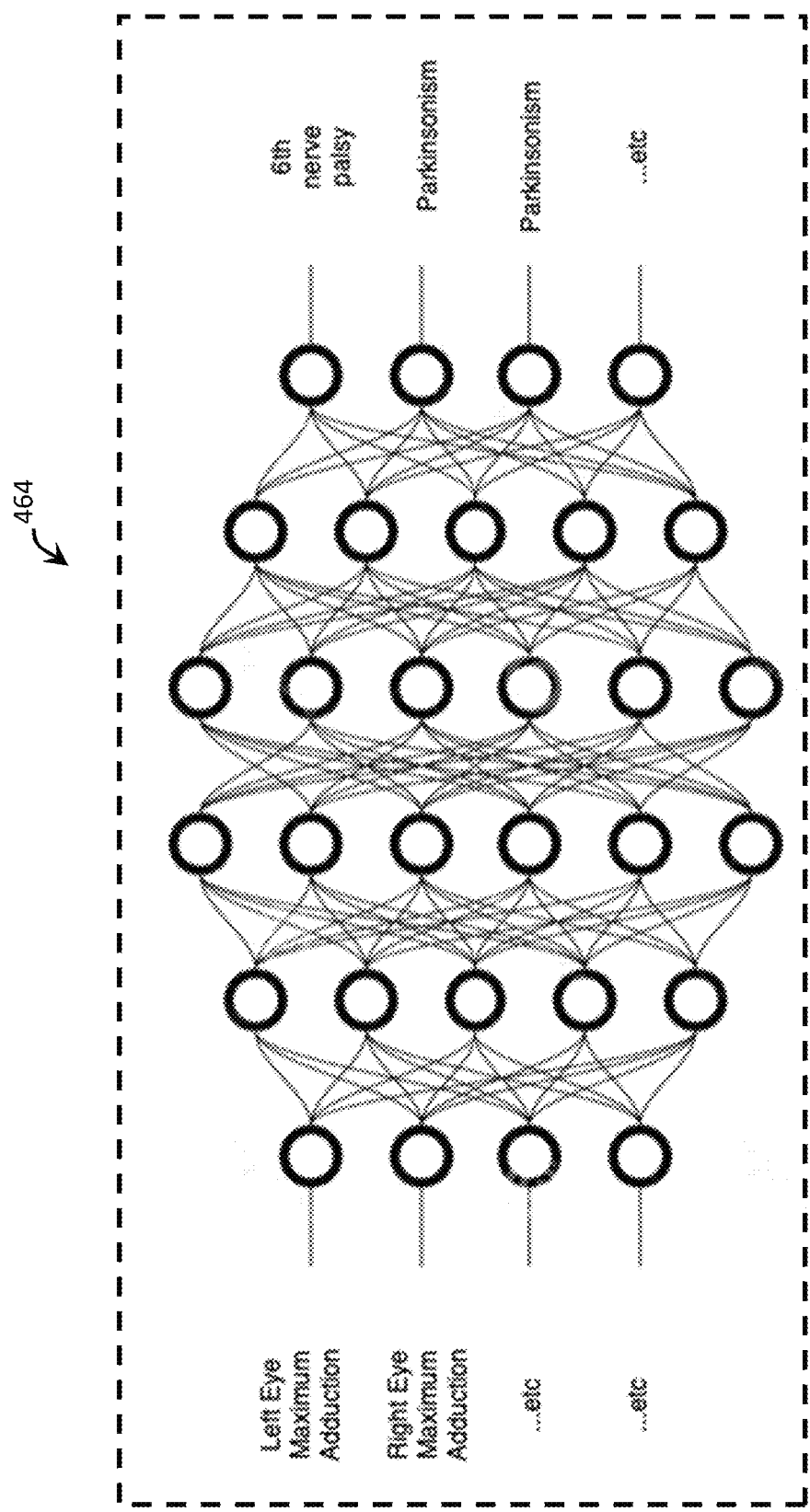
FIG. 67 is schematic diagram illustrating an example of an embodiment of a multilayer perceptron network that is executable by the medical assembly of FIG. 1.

Referring to FIG. 67, in another embodiment, the AI module 396 includes a deep ANN configured to avoid processing the entire time series data. Such ANN performs self-training based on data patterns recognized within the AI data pool 398. Such ANN is operable by the medical assembly 110 to identify a data pattern, such as left eye maximum adduction movement in degrees, right eye maximum adduction in degrees, or position of eyes when they fixated on a target at the center of the scene. In applying such ANN, the medical assembly 110 feeds these patterns as the input data to a multilayer perceptron network 464, as shown in FIG. 67. At the output, the medical assembly 110 identifies possible diagnoses of disorders related to such patterns, such as $6^{th}$ nerve palsy and Parkinsonism.

12. Examination Outputs

As described above, the examination outputs 127 provide health care providers with an aid for identifying a plurality of abnormalities, including the following: (a) abnormalities of diplopia and strabismus; (b) abnormalities of eye motility, such as nystagmus and saccadic intrusions; (c) abnormalities of pupillary functions; and (d) abnormalities of supranuclear eye movements, such as abnormalities of eye movements due to brain disorders, including multiple sclerosis.

In addition, the examination outputs 127 provide health care providers with an aid for clinically diagnosing a plurality of disorders, including disorders of balance and vertigo, such as inner ear infections and cerebrovascular diseases (e.g., stroke).

The medical assembly 110 enables health care providers to perform eye examinations (including ophthalmological examinations) with greater speed, accuracy and effectiveness than conventional eye examination methods. Furthermore, the medical assembly 110 enables health care providers to rapidly receive examination outputs 127 based on the examinations. Depending on the type of examination and configurable settings, the examination outputs 127 can include: (a) indicators of sensed eye parameters; (b) an abnormality resource depending on whether any sensed eye parameter 362 deviates from the related benchmark eye parameter 372 by more than a parameter deviation threshold 377; and (c) a diagnostic resource 388.

Depending on the type of abnormality, the abnormality resource 380 can indicate a severity level or severity indicator 378 related to one or more abnormalities identified in the examination output 127. It should be understood that not all abnormalities are indictable by severity level. For example, the presence of nystagmus is an abnormality without a relationship to severity. In such example, the abnormality resource 380 indicates or provides an abnormality indicator that indicates the presence of nystagmus.

The diagnostic resource 388 can indicate a plurality of possible diagnoses indicative of a plurality of disorders associated with one or more of the eye characteristic categories. The diagnostic resource 388 includes diagnostic certainty information at least partially based on one or more of the deviations. The diagnostic certainty information describes or specifies an estimation or assessment of the certainty of each such diagnosis. Accordingly, the medical assembly 110 and examination outputs 127 empower health care provider to identify abnormalities, perform diagnoses and render health care services to subjects with greater efficiency and effectiveness.

13. Hardware, Networks and Programming Languages

Depending on the embodiment, the programmed processor 151 can each include a CPU, GPU, microprocessor, application-specific circuit or other type of circuit, circuitry, controller or other data processing device. The medical system 114 (including the system logic 118) includes a plurality of computer-readable instructions, software, computer code, computer programs, logic, data, data libraries, data files, graphical data and commands that are executable by the programmed processor 151.

As described above, the medical system 114 can be stored in the primary data storage device 116, and the system data 125 can be stored in the secondary data storage device 122. However, in another embodiment, the medical system 114 and the system data 125 are stored in the same data storage device. In either case, each of such data storage devices can include one or more databases, data storage mediums, memory devices, hard drives having spinning magnetic disks, Solid-State Drives (SSDs), memory chips, semiconductor cells, floppy disks, optical disks (including a CD or DVD), Random Access Memory (RAM) devices, Read-Only Memory (ROM) devices (including programmable read-only memory (PROM) devices, electrically erasable programmable read-only memory (EPROM) devices, electrically erasable programmable read-only memory (EEPROM) devices, magnetic cards, optical cards, flash memory devices (including a USB key with non-volatile memory, any types of media suitable for storing electronic instructions or any other suitable type of computer-readable storage medium.

Figure 5:
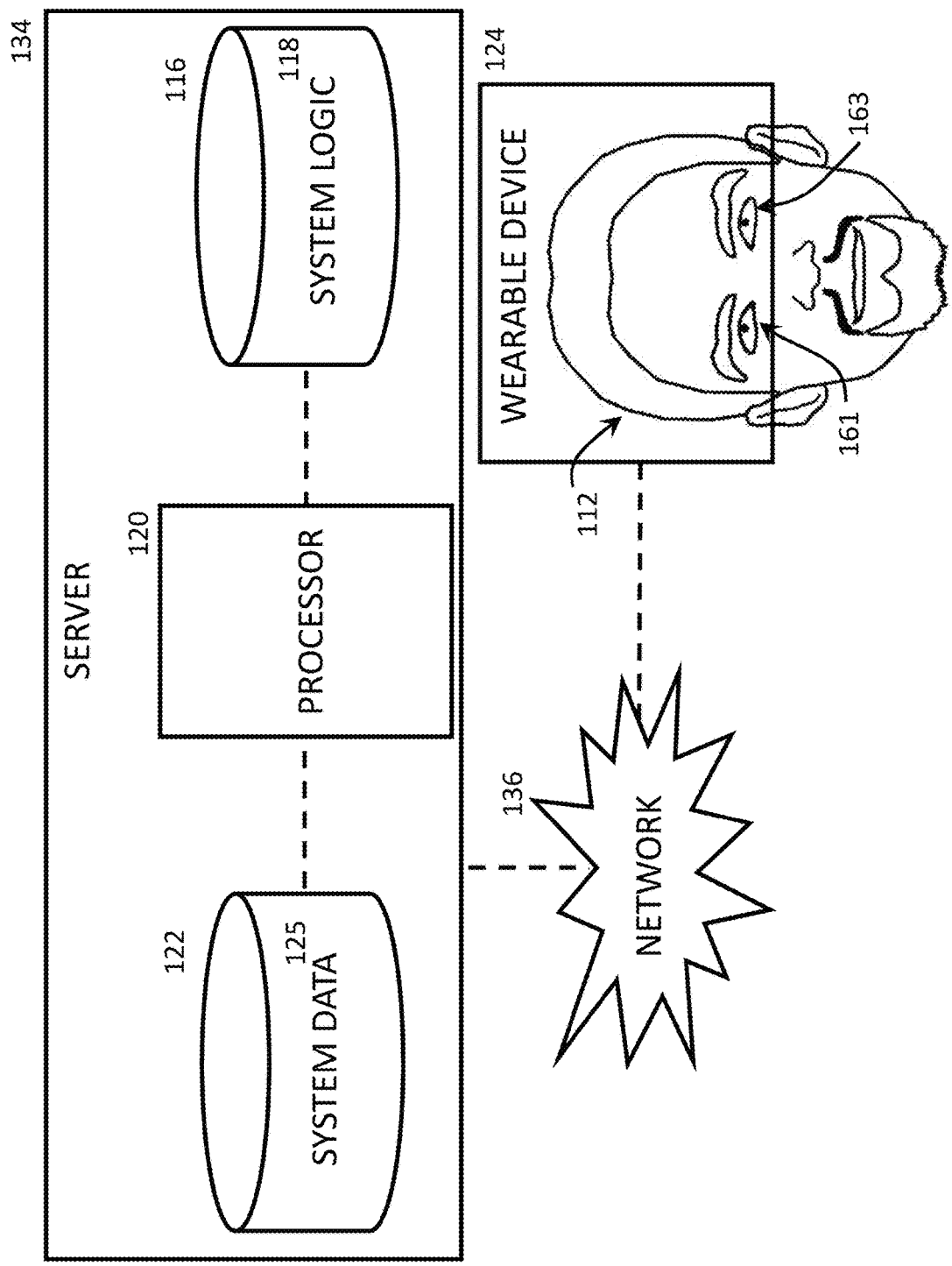
FIG. 5 is a schematic diagram illustrating a server-centric architecture of the medical assembly of FIG. 1.

The programmed processor 151 is operable to access the foregoing data storage devices over or through one or more networks, including the network 136 shown in FIG. 5. However, the programmed processor 151 is operable to directly access such data storage devices, without relying on a network, if such devices and the programmed processor 151 are parts of a single server unit. In addition, network access devices operated by users can access such data storage devices over any suitable type of network. Depending on the embodiment, the networks operable with such data storage device and processors can include one or more of the following: a wired network, a wireless network, a local area network (LAN), an extranet, an intranet, a wide area network (WAN) (including the Internet), a virtual private network (VPN), an interconnected data path across which multiple devices may communicate, a peer-to-peer network, a telephone network, portions of a telecommunications network for sending data through a variety of different communication protocols, a Bluetooth® communication network, a radio frequency (RF) data communication network, an RF pathway within a near field communication (NFC) level or range (including 13.56 MHz frequency), an infrared (IR) data communication network, a satellite communication network or a cellular communication network for sending and receiving data through short messaging service (SMS), multimedia messaging service (MMS), hypertext transfer protocol (HTTP), direct data connection, Wireless Application Protocol (WAP), email or any other suitable message transfer service or format.

To transmit communications through the foregoing networks and pathways, the programmed processor 151 is operatively coupled to one or more communication devices or wireless signal radiators, including an electromagnetic induction device, antenna, RF transmitter, RF receiver, RF transceiver, IR transmitter, IR receiver, IR transceiver or any combination of the foregoing. In an embodiment, one or more of such signal radiators is operable to wirelessly charge any battery that is coupled to the programmed processor 151.

The users (including health care providers and subjects) can use or operate any suitable input/output (I/O) device to transmit inputs to the medical assembly 110 and to receive outputs from the medical assembly 110, including a personal computer (PC) (including a desktop PC, a laptop or a tablet), smart television, Internet-enabled TV, person digital assistant, smartphone, cellular phone or mobile communication device. In an embodiment, such I/O device has at least one input device (including a touchscreen, a keyboard, a microphone, a sound sensor or a speech recognition device) and at least one output device (including a speaker, a display screen, a monitor or an LCD).

In an embodiment, the computer-readable instructions, algorithms and logic of the medical system 114 are implemented with any suitable programming or scripting language, including C, C++, Java, COBOL, assembler, PERL, Visual Basic, SQL Stored Procedures, Extensible Markup Language (XML), Hadoop, "R," json, mapreduce, python, IBM SPSS, IBM Watson Analytics, IBM Watson and Tradeoff Analytics. The medical system 114 can be implemented with any suitable combination of data structures, objects, processes, routines or other programming elements.

In an embodiment, the interfaces generated by the medical assembly 110 can be Graphical User Interfaces (GUIs) structured based on any suitable programming language. Each GUI can include, in an embodiment, multiple windows, pull-down menus, buttons, scroll bars, iconic images, popups, wizards, mouse symbols or pointers, and other suitable graphical elements. In an embodiment, the GUI incorporates multimedia, including sound, voice, motion video and virtual reality interfaces to generate outputs of the medical assembly 110.

In an embodiment, the data storage devices described above can be non-transitory mediums that store or participate in providing instructions or data to a processor for execution or processing. In such embodiment, any or all of such data storage devices can be a non-transitory data storage device. Such non-transitory devices or mediums can take different forms, including non-volatile media and volatile media. Non-volatile media can include, for example, optical or magnetic disks, flash drives, memory chips, semiconductor cells, and any of the storage devices in any computer or server. Volatile media can include dynamic memory, such as the main memory of a computer. Forms of non-transitory computer-readable media therefore include, for example, a floppy disk, flexible disk, hard disk, optical disk, magnetic disk, flash drive, memory chip, semiconductor cell, magnetic tape, magnetic medium, CD-ROM, DVD, optical medium, punch card, paper tape, any other physical medium with patterns of holes, RAM, PROM, EPROM, FLASH-EPROM, any other memory chip or cartridge, or any other medium from which a computer can read programming code and/or data. Many of these forms of computer readable media may be involved in carrying one or more sequences of one or more instructions to a processor for execution.

In contrast with non-transitory media and non-transitory data storage devices, transitory physical transmission media can include coaxial cables, copper wire and fiber optics, including the wires that comprise a bus within a computer system, a carrier wave transporting data or instructions, and cables or links transporting such a carrier wave. Carrier-wave transmission media can take the form of electric or electromagnetic signals, or acoustic or light waves, such as those generated during RF and IR data communications.

It should be appreciated that at least some of the subject matter disclosed herein includes or involves a plurality of steps or procedures. In an embodiment, some of the steps or procedures occur automatically as controlled by a processor or electrical controller. In another embodiment, some of the steps or procedures occur manually under the control of a human. In yet another embodiment, some of the steps or procedures occur semi-automatically as partially controlled by a processor or electrical controller and as partially controlled by a human.

As will be appreciated, aspects of the disclosed subject matter may be embodied as a system, method, or computer program product. Accordingly, aspects of the disclosed subject matter may take the form of an entirely hardware embodiment, an entirely software embodiment (including firmware, resident software, micro-code, etc.), or an embodiment combining software and hardware aspects that may all generally be referred to herein as a "service," "circuit," "circuitry," "module," and/or "system." Furthermore, aspects of the disclosed subject matter may take the form of a computer program product embodied in one or more computer readable mediums having computer readable program code embodied thereon.

Aspects of the disclosed subject matter are described herein in terms of steps and functions with reference to flowchart illustrations and block diagrams of methods, apparatuses, systems and computer program products. It should be understood that each such step, function block of the flowchart illustrations and block diagrams, and combinations thereof, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create results and output for implementing the functions described herein.

These computer program instructions may also be stored in a computer readable medium that can direct a computer, other programmable data processing apparatus, or other devices to function in a particular manner, such that the instructions stored in the computer readable medium produce an article of manufacture including instructions which implement the functions described herein.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions described herein.

Additional embodiments include any one of the embodiments described above and described in any and all exhibits and other materials submitted herewith, where one or more of its components, functionalities or structures is interchanged with, replaced by or augmented by one or more of the components, functionalities or structures of a different embodiment described above.

The parts, components, and structural elements of each of the wearable devices 124, 162 and 284 can be combined into an integral or unitary, one-piece object through welding, soldering, plastic molding other methods, or such parts, components, and structural elements can be distinct, removable items that are attachable to each other through screws, bolts, pins and other suitable fasteners.

In the foregoing description, certain components or elements may have been described as being configured to mate with each other. For example, an embodiment may be described as a first element (functioning as a male) configured to be inserted into a second element (functioning as a female). It should be appreciated that an alternate embodiment includes the first element (functioning as a female) configured to receive the second element (functioning as a male). In either such embodiment, the first and second elements are configured to mate with, fit with or otherwise interlock with each other.

It should be understood that various changes and modifications to the embodiments described herein will be apparent to those skilled in the art. Such changes and modifications can be made without departing from the spirit and scope of the present disclosure and without diminishing its intended advantages. It is therefore intended that such changes and modifications be covered by the appended claims.

Although several embodiments of the disclosure have been disclosed in the foregoing specification, it is understood by those skilled in the art that many modifications and other embodiments of the disclosure will come to mind to which the disclosure pertains, having the benefit of the teaching presented in the foregoing description and associated drawings. It is thus understood that the disclosure is not limited to the specific embodiments disclosed herein above, and that many modifications and other embodiments are intended to be included within the scope of the appended claims. Moreover, although specific terms are employed herein, as well as in the claims which follow, they are used only in a generic and descriptive sense, and not for the purposes of limiting the present disclosure, nor the claims which follow.

The following is claimed:

1. A medical system comprising:
one or more data storage devices storing a plurality of computer-readable instructions,
wherein the instructions are executable by one or more processors operatively coupled to a wearable device that is configured to be worn on a head of a subject during an ophthalmological examination,
wherein the wearable device comprises at least one display device and at least one sensor,
wherein the wearable device is operable to cause a 3D visual effect,
wherein the instructions are configured to cause the one or more processors and the wearable device to cooperate to:
cause the at least one display device to generate a plurality of different graphics configured to stimulate a voluntary eye function of at least one eye of the subject, to stimulate an involuntary eye function of the at least one eye, and to block a vision of the at least one eye, wherein each of the graphics is generated within a viewing space in front of the at least one eye;
cause the at least one sensor to sense a plurality of eye positions of the at least one eye relative to an environment in which the ophthalmological examination occurs, wherein the eye positions vary during an eye movement occurring while at least one of the graphics is generated during the ophthalmological examination;
cause the at least one sensor to sense a plurality of head positions of the head relative to the environment, wherein the head positions vary during any head movement that occurs during the ophthalmological examination; and
cause the at least one sensor to sense a plurality of pupil sizes of a pupil of the at least one eye, wherein the pupil sizes vary during a pupillary resizing that occurs during the ophthalmological examination,
wherein the instructions are executable by the one or more processors to:
process a plurality of sensed eye parameters, wherein the sensed eye parameters comprise:
at least one sensed eye movement parameter related to the eye movement; and
at least one sensed pupil size parameter related to the pupillary resizing;
process at least one sensed head movement parameter related to the head movement, if any; and
process medical analysis data, wherein the medical analysis data comprises:
a plurality of benchmark parameters associated with a plurality of eye characteristic categories, wherein each of the eye characteristic categories is associated with a parameter set comprising one of the sensed eye parameters and a related one of the benchmark parameters; and
a plurality of parameter deviation thresholds associated with a plurality of the eye characteristic categories; and
with respect to each of the parameter sets, determine a deviation of the sensed eye parameter of the parameter set relative to the benchmark parameter of the parameter set;
determine whether any of the deviations associated with one of the eye characteristic categories is greater than the parameter deviation threshold associated with the eye characteristic category; and
generate an examination output that indicates:
a plurality of the sensed eye parameters;
an abnormality resource as a result of at least one of deviations associated with one of the eye characteristic categories being greater than the parameter deviation threshold associated with the eye characteristic category; and a diagnostic resource comprising a plurality of possible diagnoses indicative of a plurality of disorders associated with one or more of the eye characteristic categories.

2. The medical system of claim 1, wherein:
the wearable device comprises a 3D medical headset; and
the wearable device comprises a view splitter.

3. The medical system of claim 1, wherein the ophthalmological examination comprises one or more tests for any signs of diplopia and vertigo.

4. The medical system of claim 3, wherein:
the sensed eye parameters comprise a plurality of sensed eye movement parameters related to the eye movement; and
the ophthalmological examination comprises at least two of a plurality of tests, wherein the tests comprise:
a pursuit movements test, wherein at least one of the sensed eye movement parameters is based on the at least one eye moving during the pursuit movements test;
a saccadic movements test, wherein at least one of the sensed eye movement parameters is based on the at least one eye moving during the saccadic movements test;
a vergence test, wherein at least one of the sensed eye movement parameters is based on the at least one eye moving during the vergence test;
a spontaneous eye movements test, wherein at least one of the sensed eye movement parameters is based on the at least one eye moving during the spontaneous eye movements test;
a phoria-tropia test, wherein at least one of the sensed eye movement parameters is based on the at least one eye moving during the phoria-tropia test;
a pupillary function test, wherein the at least one sensed pupil size parameter is based on the pupillary resizing occurring during the pupillary function test; and
a vestibulo-ocular functions test, wherein at least one of the sensed eye movement parameters is based on the at least one eye moving during the vestibulo-ocular functions test.

5. The medical system of claim 1, wherein each of the eye characteristic categories is associated with a type of eye abnormality, wherein the types of eye abnormalities comprise one of an eye movement abnormality and a pupil abnormality.

6. The medical system of claim 1, wherein each of the disorders is associated with a symptom, wherein the symptom comprise at least one of vertigo, double vision, and oscillopsia.

7. The medical system of claim 1, wherein:
the at least one eye comprises a first eye associated with a first one of the sensed eye parameters;
the subject comprises a second eye associated with a second one of the sensed eye parameters;
the causing and processing steps are performed with respect to the second eye; and
an additional one of the sensed eye parameters is determined depending on a comparison of the first sensed eye parameter to the second sensed eye parameter.

8. The medical system of claim 1, wherein the abnormality resource comprises a severity indicator that indicates a level of severity of an abnormality of the at least one eye.

9. The medical system of claim 1, wherein the abnormality resource comprises one of: (a) a percentile representing a value relative to a plurality of other values associated with a population; and (b) and a severity level relative to a plurality of levels of severity.

10. The medical system of claim 1, wherein:
the instructions are executable by the one or more processors to generate a probability factor that is associated with at least one of the possible diagnoses;
the probability factor represents a probability that the possible diagnosis is correct, wherein the probability factor is based, at least in part, on one or more of the deviations;
a diagnostic certainty indicator indicates the probability factor; and
the diagnostic resource comprises the diagnostic certainty indicator.

11. The medical system of claim 1, wherein the instructions comprise a plurality of instructions configured to be executed by the one or more processors to:
activate a graphic change mode during which the at least one display device displays a change in the one or more of the graphics depending on the head movement; and
deactivate the graphic change mode during an eye test conducted during operation of the wearable device.

12. A medical system comprising:
one or more data storage devices storing a plurality of computer-readable instructions,
wherein the instructions are configured to be executed by one or more processors to:
cause at least one display device of a wearable device to generate a plurality of graphics configured to stimulate a voluntary eye function of at least one eye of a subject, to stimulate an involuntary eye function of the at least one eye, and to block a vision of the at least one eye;
cause at least one sensor of the wearable device to sense an eye movement of the at least one eye relative to an environment, to sense any head movement of a head of the subject relative to the environment; and to sense a pupillary resizing of the at least on eye;
process a plurality of sensed eye parameters related to the eye movement and the pupillary resizing;
process at least one sensed head movement parameter related to the head movement, if any;
generate an examination output that indicates a plurality of the sensed eye parameters;
activate a graphic change mode during which the at least one display device displays a change in the one or more of the graphics depending on the head movement; and
deactivate the graphic change mode during a pursuit movements test conducted through use of the wearable device.

13. The medical system of claim 12, wherein:
the sensed eye parameters comprise a plurality of sensed eye movement parameters related to the eye movement;
the sensed eye parameters comprise at least one sensed pupil size parameter related to the pupillary resizing; and
the instructions are executable during an ophthalmological examination that comprises at least two of a plurality of tests, wherein the tests comprise:
a pursuit movements test, wherein at least one of the sensed eye movement parameters is based on the at least one eye moving during the pursuit movements test;
a saccadic movements test, wherein at least one of the sensed eye movement parameters is based on the at least one eye moving during the saccadic movements test;

a vergence test, wherein at least one of the sensed eye movement parameters is based on the at least one eye moving during the vergence test;

a spontaneous eye movements test, wherein at least one of the sensed eye movement parameters is based on the at least one eye moving during the spontaneous eye movements test;

a phoria-tropia test, wherein at least one of the sensed eye movement parameters is based on the at least one eye moving during the phoria-tropia test;

a pupillary function test, wherein the at least one sensed pupil size parameter is based on the pupillary resizing occurring during the pupillary function test; and a vestibulo-ocular functions test, wherein at least one of the sensed eye movement parameters is based on the at least one eye moving during the vestibulo-ocular functions test.

14. The medical system of claim 12, wherein:

the wearable device comprises a 3D medical headset; and the instructions comprise a plurality of instructions configured to be executed by the one or more processors to:

process medical analysis data, wherein the medical analysis data comprises:

a plurality of benchmark parameters associated with a plurality of eye characteristic categories, wherein each of the eye characteristic categories is associated with a parameter set comprising one of the sensed eye parameters and a related one of the benchmark parameters; and a plurality of parameter deviation thresholds associated with a plurality of the eye characteristic categories; and with respect to each of the parameter sets, determine a deviation of the sensed eye parameter of the parameter set relative to the benchmark parameter of the parameter set;

determine whether any of the deviations associated with one of the eye characteristic categories is greater than the parameter deviation threshold associated with the eye characteristic category; and generate an examination output that indicates at least one possible diagnosis indicative of at least one disorder associated with one or more of the eye characteristic categories, wherein the indicated diagnosis at least partially depends on one or more of the deviations.

15. The medical system of claim 14, wherein the examination output comprises a diagnostic certainty indicator associated with the indicated diagnosis.

16. The medical system of claim 12, wherein:

the instructions are executable by the one or more processors operatively coupled to the wearable device that is configured to be worn on a head of a subject during an ophthalmological examination; and the ophthalmological examination comprises one or more tests for a sign of a disorder that is associated with a symptom, wherein the symptom comprises diplopia or vertigo.

17. A medical method comprising:

executing a plurality of computer-readable instructions that are stored in one or more data storage devices, wherein the execution causes:

at least one display device of a wearable device to generate a plurality of graphics configured to stimulate a voluntary eye function of at least one eye of a subject, to stimulate an involuntary eye function of the at least one eye, and to block a vision of the at least one eye;

at least one sensor of the wearable device to sense an eye movement of the at least one eye relative to an environment, to sense any head movement of a head of the subject relative to the environment; and to sense a pupillary resizing of the at least on eye;

processing of a plurality of sensed eye parameters related to the eye movement and the pupillary resizing;

processing of at least one sensed head movement parameter related to the head movement, if any;

generating of an examination output that indicates a plurality of the sensed eye parameters;

an activation of a graphic change mode during which the at least one display device displays a change in the one or more of the graphics depending on the head movement; and a deactivation of the graphic change mode during a pursuit movements test conducted through use of the wearable device.

18. The medical method of claim 17, wherein:

the wearable device comprises a 3D medical headset; and the executing of the instructions comprises executing a plurality of instructions configured to cause:

processing of medical analysis data, wherein the medical analysis data comprises:

a plurality of benchmark parameters associated with a plurality of eye characteristic categories, wherein each of the eye characteristic categories is associated with a parameter set comprising one of the sensed eye parameters and a related one of the benchmark parameters; and a plurality of parameter deviation thresholds associated with a plurality of the eye characteristic categories; and with respect to each of the parameter sets, determining a deviation of the sensed eye parameter of the parameter set relative to the benchmark parameter of the parameter set;

determining of whether any of the deviations associated with one of the eye characteristic categories is greater than the parameter deviation threshold associated with the eye characteristic category; and generating of an examination output that indicates at least one possible diagnosis indicative of at least one disorder associated with one or more of the eye characteristic categories, wherein the indicated diagnosis at least partially depends on one or more of the deviations.

19. The medical method of claim 17, wherein:

the sensed eye parameters comprise a plurality of sensed eye movement parameters related to the eye movement;

the sensed eye parameters comprise at least one sensed pupil size parameter related to the pupillary resizing; and the wearable device is usable to perform at least two of a plurality of tests, wherein the tests comprise:

a pursuit movements test, wherein at least one of the sensed eye movement parameters is based on the at least one eye moving during the pursuit movements test;

a saccadic movements test, wherein at least one of the sensed eye movement parameters is based on the at least one eye moving during the saccadic movements test;

a vergence test, wherein at least one of the sensed eye movement parameters is based on the at least one eye moving during the vergence test;

a spontaneous eye movements test, wherein at least one of the sensed eye movement parameters is based on the at least one eye moving during the spontaneous eye movements test;

a phoria-tropia test, wherein at least one of the sensed eye movement parameters is based on the at least one eye moving during the phoria-tropia test;

a pupillary function test, wherein the at least one sensed pupil size parameter is based on the pupillary resizing occurring during the pupillary function test; and a vestibulo-ocular functions test, wherein at least one of the sensed eye movement parameters is based on the at least one eye moving during the vestibulo-ocular functions test.

20. The medical method of claim 17, wherein:

the examination output is related to an ophthalmological examination that occurs while the wearable device is worn on a head of a subject; and the ophthalmological examination comprises one or more tests for a sign of a disorder that is associated with a symptom, wherein the symptom comprises diplopia or vertigo.

* * * * *

UNITED STATES PATENT AND TRADEMARK OFFICE
CERTIFICATE OF CORRECTION

PATENT NO. : 11,612,316 B2
APPLICATION NO. : 16/907906
DATED : March 28, 2023
INVENTOR(S) : Awss Zidan and Ayham Boucher It is certified that error appears in the above-identified patent and that said Letters Patent is hereby corrected as shown below:

In the Claims

Claim 12: Column 48 Line 38:
Change "on eye" to --one eye--

Claim 17: Column 50 Line 8:
Change "on eye" to --one eye--

Signed and Sealed this
Eighteenth Day of July, 2023

Katherine Kelly Vidal
*Director of the United States Patent and Trademark Office*